US009526776B2

(12) United States Patent
Baudner et al.

(10) Patent No.: US 9,526,776 B2
(45) Date of Patent: Dec. 27, 2016

(54) COMBINATION VACCINES WITH SEROGROUP B MENINGOCOCCUS AND D/T/P

(71) Applicant: GlaxoSmithKline Biologicals SA, Rixensart (BE)

(72) Inventors: Barbara Baudner, Siena (IT); Derek O'Hagan, Winchester, MA (US); Manmohan Singh, Cary, NC (US); Simone Bufali, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 14/420,238

(22) PCT Filed: Sep. 6, 2013

(86) PCT No.: PCT/EP2013/068414
§ 371 (c)(1),
(2) Date: Feb. 6, 2015

(87) PCT Pub. No.: WO2014/037472
PCT Pub. Date: Mar. 13, 2014

(65) Prior Publication Data
US 2015/0190493 A1    Jul. 9, 2015

Related U.S. Application Data

(60) Provisional application No. 61/697,756, filed on Sep. 6, 2012.

(51) Int. Cl.
*A61K 39/095* (2006.01)
*A61K 39/39* (2006.01)
*A61K 39/00* (2006.01)

(52) U.S. Cl.
CPC ............. *A61K 39/095* (2013.01); *A61K 39/39* (2013.01); *A61K 2039/6037* (2013.01)

(58) Field of Classification Search
CPC ................. A61K 2300/00; A61K 2039/55505; A61K 2039/70; A61K 33/06; A61K 39/12; A61K 39/295; A61K 39/39; A61K 39/395; A61K 2039/545; A61K 39/0018; A61K 39/095; A61K 39/102; A61K 39/116; A61K 39/13; A61K 2039/05
See application file for complete search history.

(56) References Cited

U.S. PATENT DOCUMENTS

| | | |
|---|---|---|
| 4,057,685 A | 11/1977 | McIntire |
| 4,459,286 A | 7/1984 | Hilleman et al. |
| 4,663,160 A | 5/1987 | Tsay et al. |
| 4,666,886 A | 5/1987 | Baschang et al. |
| 4,673,574 A | 6/1987 | Anderson |
| 4,761,283 A | 8/1988 | Anderson |
| 4,808,700 A | 2/1989 | Anderson et al. |
| 4,965,338 A | 10/1990 | Tabankia et al. |
| 5,204,098 A | 4/1993 | Szu et al. |
| 5,306,492 A | 4/1994 | Porro |
| 5,425,946 A | 6/1995 | Tai et al. |
| 5,698,438 A | 12/1997 | Stojiljkovic et al. |
| 6,180,111 B1 | 1/2001 | Stein et al. |
| 6,531,131 B1 | 3/2003 | Gu et al. |
| 6,630,161 B1 | 10/2003 | Leesman |
| 6,645,503 B1 | 11/2003 | Arumugham et al. |
| 8,092,813 B1 | 1/2012 | Novicki |
| 8,466,167 B2 * | 6/2013 | Wu ................... C07D 221/12 514/292 |
| 9,168,313 B2 * | 10/2015 | Capiau ................ A61K 39/092 |
| 2005/0215517 A1 | 9/2005 | Rossignol et al. |
| 2006/0228380 A1 | 10/2006 | Hausdorff et al. |
| 2006/0228381 A1 | 10/2006 | Bahler et al. |
| 2007/0014805 A1 | 1/2007 | Dalencon et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2008/0102498 A1 | 5/2008 | Bahler et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0143400 A1 | 6/2009 | McInally et al. |

(Continued)

FOREIGN PATENT DOCUMENTS

| AU | 5268279 A | 5/1980 |
|---|---|---|
| CN | 101559223 A | 10/2009 |

(Continued)

OTHER PUBLICATIONS

Vaccine 23:5450-5456, 2005.*
Fransen, et al. (2007), "Agonists of Toll-like receptors 3, 4, 7, and 9 are candidates for use as adjuvants in an outer membrane vaccine against Neisseria meningitidis serogroup B.," Infection and Immunity, 75(12): 5939-46.
Gorringe, et al. (2012) "Bexsero: a multicomponent vaccine for prevention of meningococcal disease." Hum Vaccin Immunother. 8(2):174-83.
Gossger, et al. (2012), "Immunogenicity and tolerability of recombinant serogroup B meningococcal vaccine administered with or without routine infant vaccinations according to different immunization schedules: a randomized controlled trial," JAMA 307(6):573-82.

(Continued)

*Primary Examiner* — Padma V Baskar
(74) *Attorney, Agent, or Firm* — Morrison & Foerster LLP

(57) ABSTRACT

Serogroup B meningococcus antigens can successfully be combined with diphtheria, tetanus and pertussis toxoids ("DTP") to provide effective combination vaccines for protecting against multiple pathogens. These combinations are effective with a range of different adjuvants, and with both pediatric-type and booster-type DTP ratios. The adjuvant can improve the immune response which the composition elicits; alternatively, by including an adjuvant it is possible for the compositions to have a relatively lower amount of antigen while nevertheless having immunogenicity which is comparable to unadjuvanted combination vaccines.

11 Claims, 4 Drawing Sheets

(56) References Cited

U.S. PATENT DOCUMENTS

| | | |
|---|---|---|
| 2009/0192153 A1 | 7/2009 | Hashimoto et al. |
| 2009/0202484 A1 | 8/2009 | Chong et al. |
| 2009/0221631 A1 | 9/2009 | Jones et al. |
| 2010/0143301 A1 | 6/2010 | Desai et al. |

FOREIGN PATENT DOCUMENTS

| | | |
|---|---|---|
| EP | 0011243 A1 | 5/1980 |
| EP | 0208375 A2 | 1/1987 |
| EP | 0378881 A1 | 7/1990 |
| EP | 0427347 A1 | 5/1991 |
| EP | 0471177 A2 | 2/1992 |
| EP | 0477508 A1 | 4/1992 |
| EP | 0594610 A1 | 5/1994 |
| EP | WO 2007/109813 * | 9/2007 |
| EP | WO 2008/028957 * | 3/2008 |
| GB | 2220211 A | 1/1990 |
| WO | WO-9014837 A1 | 12/1990 |
| WO | WO-9101146 A1 | 2/1991 |
| WO | WO-9317712 A2 | 9/1993 |
| WO | WO-9403208 A1 | 2/1994 |
| WO | WO-9405325 A1 | 3/1994 |
| WO | WO-9421292 A1 | 9/1994 |
| WO | WO-9511700 A1 | 5/1995 |
| WO | WO-9629412 A1 | 9/1996 |
| WO | WO-9640242 A1 | 12/1996 |
| WO | WO-9842721 A1 | 10/1998 |
| WO | WO-9858668 A2 | 12/1998 |
| WO | WO-9910497 A1 | 3/1999 |
| WO | WO-9957280 A2 | 11/1999 |
| WO | WO-9961053 A1 | 12/1999 |
| WO | WO-0010599 A2 | 3/2000 |
| WO | WO-0023595 A1 | 4/2000 |
| WO | WO-0025811 A2 | 5/2000 |
| WO | WO-0026384 A1 | 5/2000 |
| WO | WO-0033882 A1 | 6/2000 |
| WO | WO-0056360 A2 | 9/2000 |
| WO | WO-0061761 A2 | 10/2000 |
| WO | WO-0066741 A2 | 11/2000 |
| WO | WO-0109350 A2 | 2/2001 |
| WO | WO-0134642 A2 | 5/2001 |
| WO | WO-0137863 A2 | 5/2001 |
| WO | WO-0138350 A2 | 5/2001 |
| WO | WO-0141800 A2 | 6/2001 |
| WO | WO-0155182 A1 | 8/2001 |
| WO | WO-0172337 A1 | 10/2001 |
| WO | WO-0191788 A1 | 12/2001 |
| WO | WO-0209643 A2 | 2/2002 |
| WO | WO-0209746 A2 | 2/2002 |
| WO | WO-02058737 A2 | 8/2002 |
| WO | WO-02062378 A2 | 8/2002 |
| WO | WO-02091998 A2 | 11/2002 |
| WO | WO-03007985 A2 | 1/2003 |
| WO | WO-03011223 A2 | 2/2003 |
| WO | WO-03063766 A2 | 8/2003 |
| WO | WO-03066094 A2 | 8/2003 |
| WO | WO-03080678 A1 | 10/2003 |
| WO | WO-03105890 A2 | 12/2003 |
| WO | WO-2004014417 A2 | 2/2004 |
| WO | WO-2004014418 A2 | 2/2004 |
| WO | WO-2004015099 A2 | 2/2004 |
| WO | WO-2004019977 A2 | 3/2004 |
| WO | WO-2004032958 A1 | 4/2004 |
| WO | WO-2004048404 A2 | 6/2004 |
| WO | WO-2005000347 A1 | 1/2005 |
| WO | WO-2005004908 A1 | 1/2005 |
| WO | WO-2005033148 A1 | 4/2005 |
| WO | WO-2005097181 A1 | 10/2005 |
| WO | WO-2006024946 A2 | 3/2006 |
| WO | WO-2006046143 A2 | 5/2006 |
| WO | WO-2006081259 A2 | 8/2006 |
| WO | WO-2007000314 A2 | 1/2007 |
| WO | WO-2007000322 A1 | 1/2007 |
| WO | WO-2007000343 A2 | 1/2007 |
| WO | WO-2007034173 A1 | 3/2007 |
| WO | WO-2007034917 A1 | 3/2007 |
| WO | WO-2007040840 A2 | 4/2007 |
| WO | WO-2007053455 A2 | 5/2007 |
| WO | WO-2007054820 A2 | 5/2007 |
| WO | WO-2007071707 A2 | 6/2007 |
| WO | WO-2007080308 A2 | 7/2007 |
| WO | WO-2007093901 A1 | 8/2007 |
| WO | WO-2008004948 A1 | 1/2008 |
| WO | WO-2008005555 A1 | 1/2008 |
| WO | WO-2008043774 A1 | 4/2008 |
| WO | WO-2008056263 A2 | 5/2008 |
| WO | WO-2008101867 A1 | 8/2008 |
| WO | WO-2008114817 A1 | 9/2008 |
| WO | WO-2008135791 A1 | 11/2008 |
| WO | WO-2008143709 A2 | 11/2008 |
| WO | WO-2009019553 A2 | 2/2009 |
| WO | WO-2009038889 A1 | 3/2009 |
| WO | WO-2009067081 A1 | 5/2009 |
| WO | WO-2009104097 A2 | 8/2009 |
| WO | WO-2009111337 A1 | 9/2009 |
| WO | WO-2009118296 A2 | 10/2009 |
| WO | WO-2010014913 A1 | 2/2010 |
| WO | WO-2010023551 A2 | 3/2010 |
| WO | WO-2010025964 A1 | 3/2010 |
| WO | WO-2010070453 A2 | 6/2010 |
| WO | WO-2010077613 A1 | 7/2010 |
| WO | WO-2011024072 A2 | 3/2011 |
| WO | WO-2011027222 A2 | 3/2011 |
| WO | WO-2011036562 A1 | 3/2011 |
| WO | WO-2011039631 A2 | 4/2011 |
| WO | WO-2011067669 A2 | 6/2011 |
| WO | WO-2011067672 A2 | 6/2011 |
| WO | WO-2011067673 A2 | 6/2011 |
| WO | WO-2011110655 A2 | 9/2011 |
| WO | WO-2011119759 A1 | 9/2011 |
| WO | WO-2011141819 A1 | 11/2011 |
| WO | WO-2011154442 A2 | 12/2011 |
| WO | WO-2011154443 A1 | 12/2011 |
| WO | WO-2011154444 A1 | 12/2011 |
| WO | WO2012/020326 A1 * | 2/2012 |
| WO | WO-2012031140 A1 | 3/2012 |
| WO | WO-2012117377 A1 | 9/2012 |

OTHER PUBLICATIONS

Podda & Del Giudice (2003) "MF59-adjuvanted vaccines: increased immunogenicity with an optimal safety profile." Expert Rev Vaccines, 2(2):197-203.

Podda (2001) "The adjuvanted influenza vaccines with novel adjuvants: experience with the MF59-adjuvanted vaccine." Vaccine, 19(17-19):2673-2680.

Giuliani, et al. (2006) "A universal vaccine for serogroup B meningococcus." Proc. Nat'l. Acad. Sci. (USA), 103:10834-10839.

* cited by examiner

COMBINATION VACCINES WITH SEROGROUP B MENINGOCOCCUS AND D/T/P

RELATED APPLICATIONS

This application is the U.S. National Phase of International Application No. PCT/EP2013/068414, entitled "COMBINATION VACCINES WITH SEROGROUP B MENINGOCOCCUS AND D/T/P," filed Sep. 6, 2013 and published in English, which claims the benefit of U.S. provisional application 61/697,756 filed 6 Sep. 2012, the complete contents of all of which are hereby incorporated herein by reference for all purposes.

SEQUENCE LISTING

The instant application contains a Sequence Listing which was submitted in ASCII format in PCT application PCT/EP2013/068414 and is hereby incorporated by reference in its entirety. Said ASCII copy, created on, Sep. 5, 2013 is named st25 sequence listing and is 124,594 bytes in size.

TECHNICAL FIELD

This invention is in the field of combination vaccines i.e. vaccines containing mixed immunogens from more than one pathogen, such that administration of the vaccine can simultaneously immunize a subject against more than one pathogen.

BACKGROUND ART

Vaccines containing antigens from more than one pathogenic organism within a single dose are known as "multivalent" or "combination" vaccines. Various combination vaccines have been approved for human use, including trivalent vaccines for protecting against diphtheria, tetanus and pertussis or against measles, mumps and rubella. These vaccines offer patients the advantage of receiving a reduced number of injections, which can lead to the clinical advantage of increased compliance (e.g. see chapter 29 of ref. 1), particularly in pediatric patients.

One difficulty when providing new combination vaccines is the potential for adverse vaccine-vaccine interactions between the mixed components, which may be due to physical or chemical factors. For instance, reference 2 discusses potential alterations in immunogenicity when antigens are combined, and reference 3 reports that the development of combination vaccines involves much more than the simple mixing of existing antigens. Similarly, reference 4 reviews a variety of clinically-relevant interactions (see also reference 5), and reference 6 reviews the technical challenges faced when making a combination vaccine.

It is an object of the invention to provide further and improved combination vaccines, and in particular those which can protect against serogroup B meningococcus and other pathogens.

SUMMARY OF THE INVENTION

The inventors have shown that serogroup B meningococcus antigens can successfully be combined with diphtheria, tetanus and pertussis toxoids ("DTP") to provide effective combination vaccines for protecting against multiple pathogens. These combinations are effective with a range of different adjuvants, and with both pediatric-type and booster-type DTP ratios. The adjuvant can improve the immune response which the composition elicits; alternatively, by including an adjuvant it is possible for the compositions to have a relatively lower amount of antigen while nevertheless having immunogenicity which is comparable to unadjuvanted combination vaccines.

In general, therefore, the invention provides an immunogenic composition comprising (a) a serogroup B meningococcus immunogen and (b) at least one of a diphtheria toxoid, a tetanus toxoid, and/or a pertussis toxoid. The composition will usually also include an adjuvant, such as an aluminium salt or an oil-in-water emulsion. Preferably component (b) includes all three of a diphtheria toxoid, a tetanus toxoid, and a pertussis toxoid. In some embodiments component (b) includes more diphtheria toxoid than tetanus toxoid (measured in Lf units), but in other embodiments it includes more tetanus toxoid than diphtheria toxoid.

In a first embodiment the invention provides an immunogenic composition comprising: (a) a serogroup B meningococcus immunogen; (b) a diphtheria toxoid, a tetanus toxoid, and a pertussis toxoid; and (c) an adjuvant. The adjuvant can comprise one or more of an aluminium salt adjuvant, a TLR agonist, or an oil-in-water emulsion.

In a second embodiment the invention provides an immunogenic composition comprising: (a) a serogroup B meningococcus immunogen; and (b) a diphtheria toxoid, a tetanus toxoid, and a pertussis toxoid, wherein the diphtheria toxoid is present in an excess relative to tetanus toxoid as measured in Lf units. This composition can also include an adjuvant, and this can comprise one or more of an aluminium salt adjuvant, a TLR agonist, or an oil-in-water emulsion.

In a third embodiment the invention provides an immunogenic composition comprising: (a) a serogroup B meningococcus immunogen; and (b) a diphtheria toxoid, a tetanus toxoid, and a pertussis toxoid, wherein the tetanus toxoid is present in an excess relative to diphtheria toxoid as measured in Lf units. This composition can also include an adjuvant, and this can comprise one or more of an aluminium salt adjuvant, a TLR agonist, or an oil-in-water emulsion.

Compositions of the invention can include antigens in addition to diphtheria toxoid, tetanus toxoid, and pertussis toxoid e.g. they can include Hib capsular saccharide (ideally conjugated), HBsAg, IPV, meningococcal capsular saccharide (ideally conjugated), etc.

Serogroup B Meningococcus Immunogens

Immunogenic compositions of the invention include a serogroup B meningococcus immunogen. When administered to human beings (or to a suitable animal model) the immunogen can elicit a bactericidal immune response. These immunogens can be proteins, liposaccharides, or vesicles.

Various serogroup B meningococcus protein immunogens are known in the art, including but not limited to NHBA, fHbp and NadA as found in the BEXSERO™ product [7,8]. Further protein immunogens which can be included in compositions of the invention are HmbR, NspA, NhhA, App, Omp85, TbpA, TbpB, Cu,Zn-superoxide dismutase, and ZnuD. Further details of these immunogens are discussed below.

A vaccine may include one or more of these various immunogens e.g. it can include each of NHBA, fHbp and NadA. It can also include variant forms of a single immunogen e.g. it can include more than one variant of meningococcal fHbp (i.e. two fHbp proteins with different sequences [191, 9]).

The serogroup B meningococcus protein immunogens can be present as fusion proteins. For instance, the BEX-SERO™ product includes two fusion proteins: SEQ ID NO: 4 is a fusion of NMB2091 and a fHbp; and SEQ ID NO: 5 is a fusion of a NHBA and NMB1030. One useful fusion protein is SEQ ID NO: 19, which includes NMB2091 and two copies of a fHbp.

Two useful combinations of serogroup B immunogens include: a NHBA e.g. SEQ ID NO: 5; a fHbp e.g. either SEQ ID NO: 4 or SEQ ID NO: 19; and a NadA e.g. SEQ ID NO: 6. Other useful combinations include proteins which differ from SEQ ID NOs: 5, 4, 19 & 6 by up to 5 amino acids each but which retain the ability to elicit antibodies which recognise SEQ ID NOs: 5, 4, 19 & 6.

Compositions which include at least one fHbp immunogen are preferred e.g. those containing two different fHbp sequences. Details of suitable fHbp combinations are discussed below.

Thus compositions of the invention can usefully include (a) the mixture of three serogroup B meningococcus protein immunogens disclosed as '5CVMB' in reference 8 or (b) the mixture of serogroup B meningococcus protein immunogens disclosed as 'rLP2086' in reference 10.

Usually, the serogroup B meningococcus immunogens are purified soluble recombinant proteins. In some embodiments, however, they can be present in meningococcal vesicles. Thus the composition can include meningococcal vesicles i.e. any proteoliposomic vesicle obtained by disruption of or blebbing from a meningococcal outer membrane to form vesicles therefrom that retain antigens from the outer membrane. Thus this term includes, for instance, OMVs (sometimes referred to as 'blebs'), microvesicles (MVs) and 'native OMVs' ('NOMVs'). Various such vesicles are known in the art (e.g. see references 11 to 25) and any of these can be included within a composition of the invention. Further details of these vesicles are given below. In some embodiments, however, the composition is vesicle-free.

A composition of the invention can preferably elicit a serum bactericidal assay after being administered. These responses are conveniently measured in mice and are a standard indicator of vaccine efficacy. Serum bactericidal activity (SBA) measures bacterial killing mediated by complement, and can be assayed using human or baby rabbit complement. For instance, a composition may induce at least a 4-fold rise in SBA in more than 90% of recipients.

A composition of the invention can preferably elicit an immune response in human beings which is protective against serogroup B meningococcus. For instance, the vaccine may elicit an immune response which is protective at least against a prototype serogroup B strain such as MC58, which is widely available (e.g. ATCC BAA-335) and was the strain sequenced in reference 26. Other strains can also be used, but a response against MC58 is easily tested.

Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

A composition should include enough diphtheria toxoid to elicit circulating diphtheria antitoxin levels of at least 0.01 IU/ml. Quantities of diphtheria toxoid are generally measured in the 'Lf' unit ("flocculating units", or the "limes flocculating dose", or the "limit of flocculation"), defined as the amount of toxin/toxoid which, when mixed with one International Unit of antitoxin, produces an optimally flocculating mixture [27,28]. For example, the NIBSC supplies 'Diphtheria Toxoid, Plain' [29], which contains 300 LF per ampoule, and also supplies 'The 1st International Reference Reagent For Diphtheria Toxoid For Flocculation Test' [30] which contains 900 Lf per ampoule. The concentration of diphtheria toxoid in a composition can readily be determined using a flocculation assay by comparison with a reference material calibrated against such reference reagents.

The immunizing potency of diphtheria toxoid in a composition is generally expressed in international units (IU). The potency can be assessed by comparing the protection afforded by a composition in laboratory animals (typically guinea pigs) with a reference vaccine that has been calibrated in IUs. NIBSC supplies the 'Diphtheria Toxoid Adsorbed Third International Standard 1999' [31,32], which contains 160 IU per ampoule, and is suitable for calibrating such assays.

The conversion between IU and Lf systems depends on the particular toxoid preparation.

Compositions of the invention typically include, per unit dose, between 1-40 Lf diphtheria toxoid. In a pediatric-type composition, where the diphtheria toxoid is present in an excess relative to tetanus toxoid (in Lf units), the composition will generally include between 10-35 Lf diphtheria toxoid per unit dose e.g. between 15-30 Lf, such as 15, 25 or 30 Lf. In a booster-type composition, where tetanus toxoid is present in an excess relative to the diphtheria toxoid (in Lf units), the composition will generally include between 1-4 Lf diphtheria toxoid per unit dose e.g. between 1.5-3 Lf, such as 2 or 2.5 Lf. If a composition includes saccharide antigen(s) conjugated to diphtheria toxoid then these amounts exclude the amount of carrier protein in those conjugate(s).

By IU measurements, pediatric-type compositions will generally include ≥25 IU diphtheria toxoid per unit dose, whereas booster-type compositions will generally include 1-3 IU per unit dose.

If a composition includes an aluminium salt adjuvant then diphtheria toxoid in the composition is preferably adsorbed (more preferably totally adsorbed) onto it, and preferably onto an aluminium hydroxide adjuvant.

Tetanus Toxoid

Tetanus is caused by *Clostridium tetani*, a Gram-positive, spore-forming *bacillus*. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

A composition should include enough tetanus toxoid to elicit circulating tetanus antitoxin levels of at least 0.01 IU/ml. Quantities of tetanus toxoid are generally expressed in 'Lf' units (see above), defined as the amount of toxoid which, when mixed with one International Unit of antitoxin, produces an optimally flocculating mixture [27]. The NIBSC supplies 'The 1st International Reference Reagent for Tetanus Toxoid For Flocculation Test' [33] which contains 1000 LF per ampoule, by which measurements can be calibrated.

The immunizing potency of tetanus toxoid is measured in international units (IU), assessed by comparing the protection afforded by a composition in laboratory animals (typically guinea pigs) with a reference vaccine e.g. using NIBSC's 'Tetanus Toxoid Adsorbed Third International Standard 2000' [34,35], which contains 469 IU per ampoule.

The conversion between IU and Lf systems depends on the particular toxoid preparation.

Compositions of the invention typically include between 2.5-25 Lf of tetanus toxoid per unit dose. In a pediatric-type composition, where diphtheria toxoid is present in an excess relative to the tetanus toxoid (in Lf units), the composition will generally include between 4-15 Lf tetanus toxoid per unit dose e.g. between 5-10 Lf, such as 5 or 10 Lf. In a booster-type composition, where the tetanus toxoid is present in an excess relative to diphtheria toxoid (in Lf units), the composition will generally include between 4-6 Lf tetanus toxoid per unit dose e.g. 5 Lf. If a composition includes saccharide antigen(s) conjugated to tetanus toxoid then these amounts exclude the amount of carrier protein in those conjugate(s).

By IU measurements, pediatric-type compositions will generally include ≥40 IU tetanus toxoid per unit dose, whereas booster-type compositions will generally include 15-25 IU per unit dose.

If a composition includes an aluminium salt adjuvant then tetanus toxoid in the composition is preferably adsorbed (sometimes totally adsorbed) onto an aluminium salt, preferably onto an aluminium hydroxide adjuvant.

Pertussis Toxoid

*Bordetella pertussis* causes whooping cough. Compositions of the invention include pertussis toxoid ('PT') i.e. a detoxified form of pertussis toxin. The invention can use a PT-containing whole-cell pertussis antigen ("wP") but preferably a composition is free from wP and instead includes an acellular ("aP") PT-containing antigen i.e. a defined mixture of purified pertussis antigens. When using an aP antigen a composition of the invention will typically include, in addition to the PT, filamentous hemagglutinin (FHA) and/or pertactin (also known as the '69 kiloDalton outer membrane protein'). It can also optionally include fimbriae types 2 and 3. Preparation of these various Pa antigens is well known in the art.

PT can be detoxified by treatment with formaldehyde and/or glutaraldehyde, and FHA and pertactin can also be treated in the same way. As an alternative to chemical detoxification of PT, the invention can use a mutant PT in which wild-type enzymatic activity has been reduced by mutagenesis [36] e.g. the 9K/129G double mutant [37]. The use of such genetically-detoxified PT is preferred, Quantities of acellular pertussis antigens are usually expressed in micrograms. Compositions of the invention typically include between 2-30 μg PT per unit dose. In a pediatric-type composition, PT can be present at between 5-30 μg per unit dose (e.g. 5, 7.5, 20 or 25 μg), whereas in a booster-type composition the composition will generally include between 2-10 μg PT per unit dose (e.g. 2.5 μg or 8 μg). Where a composition includes FHA, it is typically present between 2-30 μg per unit dose. In a pediatric-type composition, FHA can be present at between 2.5-25 μg per unit dose (e.g. 2.5, 5, 10, 20 or 25 μg), whereas in a booster-type composition FHA can be present at between 4-10 μg per unit dose (e.g. 5 μg or 8 μg). Where a composition includes pertactin, this is typically present between 2-10 μg per unit dose. In a pediatric-type composition, pertactin can be present at between 2.5-10 μg per unit dose (e.g. 2.5, 3, 8 or 10 μg), whereas in a booster-type composition pertactin can be present at between 2-3 μg per unit dose (e.g. 2.5 μg or 3 μg)

A composition normally contains ≤80 μg per unit dose of total acellular pertussis antigens. Each individual antigen will usually be present at ≤30 μg per unit dose.

It is usual that each of PT, FHA and pertactin are present in a composition of the invention. These may be present at various ratios (by mass), such as PT:FHA:p69 ratios of 20:20:3, 25:25:8, 16:16:5, 5:10:6, or 10:5:3. It is usual to have a mass excess of FHA relative to pertactin if both are present.

If a composition includes an aluminium salt adjuvant then PT in the composition is preferably adsorbed (sometimes totally adsorbed) onto an aluminium salt, preferably onto an aluminium hydroxide adjuvant. Any FHA can also be adsorbed to the aluminium salt. Any pertactin can be adsorbed to the aluminium salt adjuvant, but the presence of pertactin normally means that the composition requires the presence of aluminium hydroxide to ensure stable adsorption [38].

Hib Conjugates

*Haemophilus influenzae* type b ('Hib') causes bacterial meningitis. Hib vaccines are typically based on the capsular saccharide antigen (e.g. chapter 14 of ref. 1), the preparation of which is well documented (e.g. references 39 to 48). The Hib saccharide is conjugated to a carrier protein in order to enhance its immunogenicity, especially in children. Typical carrier proteins are tetanus toxoid, diphtheria toxoid, the CRM197 derivative of diphtheria toxoid, or the outer membrane protein complex from serogroup B meningococcus. Tetanus toxoid is a useful carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl) carbodiimide), typically the hydrochloride salt), and then reacting the linker-saccharide entity with a tetanus toxoid carrier protein. CRM197 is another useful carrier for Hib conjugate in compositions of the invention.

The saccharide moiety of the conjugate may comprise full-length polyribosylribitol phosphate (PRP) as prepared from Hib bacteria, and/or fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2.5 and 1:3.5. In vaccines where tetanus toxoid is present both as an antigen and as a carrier protein then the weight ratio of saccharide to carrier protein in the conjugate may be between 1:0.3 and 1:2 [49]. Administration of the Hib conjugate preferably results in an anti-PRP antibody concentration of ≥0.15 μg/ml, and more preferably ≥1 μg/ml, and these are the standard response thresholds.

Quantities of Hib antigens are typically expressed in micrograms of saccharide. If a composition of the invention includes a Hib antigen then a normal quantity per unit dose is between 5-15 µg e.g. 10 µg or 12 µg.

If a composition includes an aluminium salt adjuvant then Hib antigen can be adsorbed onto it or can be unadsorbed.
Hepatitis B Virus Surface Antigen Hepatitis B virus (HBV) is one of the known agents which causes viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention is recombinantly expressed e.g. in yeast or CHO cells. Suitable yeasts include *Saccharomyces* (such as *S. cerevisiae*) or *Hanensula* (such as *H. polymorpha*) hosts.

Unlike native HBsAg (i.e. as in the plasma-purified product), yeast-expressed HBsAg is generally non-glycosylated, and this is the most preferred form of HBsAg for use with the invention. Yeast-expressed HBsAg is highly immunogenic and can be prepared without the risk of blood product contamination.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [50]. The particles may retain non-ionic surfactant (e.g. polysorbate 20) if this was used during disruption of yeast [51].

A preferred method for HBsAg purification involves, after cell disruption: ultrafiltration; size exclusion chromatography; anion exchange chromatography; ultracentrifugation; desalting; and sterile filtration. Lysates may be precipitated after cell disruption (e.g. using a polyethylene glycol), leaving HBsAg in solution, ready for ultrafiltration.

After purification HBsAg may be subjected to dialysis (e.g. with cysteine), which can be used to remove any mercurial preservatives such as thimerosal that may have been used during HBsAg preparation [52]. Thimerosal-free preparation is preferred.

The HBsAg is preferably from HBV subtype adw2.

Quantities of HBsAg are typically expressed in micrograms. If a composition of the invention includes HBsAg then a normal quantity per unit dose is between 5-25 µg e.g. 10 µg or 20 µg.

If a composition includes an aluminium salt adjuvant then HBsAg can be adsorbed onto it (preferably adsorbed onto an aluminium phosphate adjuvant).
Inactivated Poliovirus Antigen (IPV)

Poliomyelitis can be caused by one of three types of poliovirus. The three types are similar and cause identical symptoms, but they are antigenically very different and infection by one type does not protect against infection by others. As explained in chapter 24 of reference 1, it is therefore preferred to use three poliovirus antigens with the invention—poliovirus Type 1 (e.g. Mahoney strain), poliovirus Type 2 (e.g. MEF-1 strain), and poliovirus Type 3 (e.g. Saukett strain). As an alternative to these strains ("Salk" strains), Sabin strains of types 1 to 3 can be used e.g. as discussed in references 53 & 54. These strains can be more potent than the normal Salk strains.

Polioviruses may be grown in cell culture. A preferred culture uses a Vero cell line, which is a continuous cell line derived from monkey kidney. Vero cells can conveniently be cultured microcarriers. Culture of the Vero cells before and during viral infection may involve the use of bovine-derived material, such as calf serum, and of lactalbumin hydrolysate (e.g. obtained by enzymatic degradation of lactalbumin). Such bovine-derived material should be obtained from sources which are free from BSE or other TSEs.

After growth, virions may be purified using techniques such as ultrafiltration, diafiltration, and chromatography. Prior to administration to patients, polioviruses must be inactivated, and this can be achieved by treatment with formaldehyde before the viruses are used in the process of the invention.

The viruses are preferably grown, purified and inactivated individually, and are then combined to give a bulk mixture for use with the invention.

Quantities of IPV are typically expressed in the 'DU' unit (the "D-antigen unit" [55]). Where all three of Types 1, 2 and 3 poliovirus are present the three antigens can be present at a DU ratio of 5:1:4 respectively, or at any other suitable ratio e.g. a ratio of 15:32:45 when using Sabin strains [53]. Typical amounts of Salk IPV strains per unit dose are 40DU type 1, 8DU type 2 and 32DU type 3, although lower doses can also be used. A low amount of antigen from Sabin strains is particularly useful, with ≤15 DU type 1, ≤5 DU type 2, and ≤25 DU type 3 (per unit dose).

If a composition includes an aluminium salt adjuvant then IPV antigens are often not pre-adsorbed to any adjuvant before they are formulated, but after formulation they may become adsorbed onto the aluminium salt(s).
Further Antigens Compositions of the invention include D, T, and P antigens. As mentioned above, they may also include Hib, HBsAg, and/or poliovirus antigens. Immunogenic compositions of the invention may include antigens from further pathogens. For example, these antigens may be from *N. meningitidis* (one or more of serogroups A, B, C, W135 and/or Y) or *S. pneumoniae*.
Meningococcal Saccharides Where a composition includes a *Neisseria meningitidis* capsular saccharide conjugate there may be one or more than one such conjugate. Including 2, 3, or 4 of serogroups A, C, W135 and Y is typical e.g. A+C, A+W135, A+Y, C+W135, C+Y, W135+Y, A+C+W135, A+C+Y, A+W135+Y, A+C+W135+Y, etc. Components including saccharides from all four of serogroups A, C, W135 and Y are useful, as in the MENACTRA™ and MENVEO™ products. Where conjugates from more than one serogroup are included then they may be present at substantially equal masses e.g. the mass of each serogroup's saccharide is within ±10% of each other. A typical quantity per serogroup is between 1 µg and 20 µg e.g. between 2 and 10 µg per serogroup, or about 4 µg or about 5 µg or about 10 µg. As an alternative to a substantially equal ratio, a double mass of serogroup A saccharide may be used.

Administration of a conjugate preferably results in an increase in serum bactericidal assay (SBA) titre for the relevant serogroup of at least 4-fold, and preferably at least 8-fold. SBA titres can be measured using baby rabbit complement or human complement [56].

The capsular saccharide of serogroup A meningococcus is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [57], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc–(α2→. Most serogroup C strains have O-acetyl groups at C-7 and/or C-8 of the sialic acid residues, but about 15% of clinical isolates lack these O-acetyl groups [58,59]. The presence or absence of OAc groups generates unique epitopes, and the specificity of antibody binding to the saccharide may affect its bactericidal activity against O-acetylated (OAc–) and de-O-acetylated (OAc+) strains [60-62]. Serogroup C saccharides used with the invention may be prepared from either OAc+ or OAc– strains. Licensed MenC conjugate vaccines include both OAc– (NEISVAC-C™) and OAc+ (MENJUGATE™ & MENINGITEC™) saccharides. In some embodiments, strains for production of serogroup C conjugates are OAc+ strains, e.g. of serotype 16, serosubtype P1.7a, 1, etc. Thus C:16:P1.7a, 1 OAc+ strains may be used. OAc+ strains in serosubtype P1.1 are also useful, such as the C11 strain. Preferred MenC saccharides are taken from OAc+ strains, such as strain C11.

The serogroup W135 saccharide is a polymer of sialic acid-galactose disaccharide units. Like the serogroup C saccharide, it has variable O-acetylation, but at sialic acid 7 and 9 positions [63]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [63]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides. For example, reference 64 reports the use of serogroup Y saccharides that are more than 80% de-O-acetylated.

The saccharide moieties in meningococcal conjugates may comprise full-length saccharides as prepared from meningococci, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. One depolymerisation method involves the use of hydrogen peroxide [65]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [66]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa. In other embodiments, the average molecular weight for saccharides from each of meningococcal serogroups A, C, W135 and Y may be more than 50 kDa e.g. ≥75 kDa, ≥100 kDa, ≥110 kDa, ≥120 kDa, ≥130 kDa, etc. [67], and even up to 1500 kDa, in particular as determined by MALLS. For instance: a MenA saccharide may be in the range 50-500 kDa e.g. 60-80 kDa; a MenC saccharide may be in the range 100-210 kDa; a MenW135 saccharide may be in the range 60-190 kDa e.g. 120-140 kDa; and/or a MenY saccharide may be in the range 60-190 kDa e.g. 150-160 kDa.

If a component or composition includes both Hib and meningococcal conjugates then, in some embodiments, the mass of Hib saccharide can be substantially the same as the mass of a particular meningococcal serogroup saccharide. In some embodiments, the mass of Hib saccharide will be more than (e.g. at least 1.5×) the mass of a particular meningococcal serogroup saccharide. In some embodiments, the mass of Hib saccharide will be less than (e.g. at least 1.5× less) the mass of a particular meningococcal serogroup saccharide.

Where a composition includes saccharide from more than one meningococcal serogroup, there is an mean saccharide mass per serogroup. If substantially equal masses of each serogroup are used then the mean mass will be the same as each individual mass; where non-equal masses are used then the mean will differ e.g. with a 10:5:5:5 µg amount for a MenACWY mixture, the mean mass is 6.25 µg per serogroup. In some embodiments, the mass of Hib saccharide will be substantially the same as the mean mass of meningococcal saccharide per serogroup. In some embodiments, the mass of Hib saccharide will be more than (e.g. at least 1.5×) the mean mass of meningococcal saccharide per serogroup. In some embodiments, the mass of Hib saccharide will be less than (e.g. at least 1.5×) the mean mass of meningococcal saccharide per serogroup [68].

Pneumococcal Saccharides

*Streptococcus pneumoniae* causes bacterial meningitis and existing vaccines are based on capsular saccharides. Thus compositions of the invention can include at least one pneumococcal capsular saccharide conjugated to a carrier protein.

The invention can include capsular saccharide from one or more different pneumococcal serotypes. Where a composition includes saccharide antigens from more than one serotype, these are preferably prepared separately, conjugated separately, and then combined. Methods for purifying pneumococcal capsular saccharides are known in the art (e.g. see reference 69) and vaccines based on purified saccharides from 23 different serotypes have been known for many years. Improvements to these methods have also been described e.g. for serotype 3 as described in reference 70, or for serotypes 1, 4, 5, 6A, 6B, 7F and 19A as described in reference 71.

Pneumococcal capsular saccharide(s) will typically be selected from the following serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. Thus, in total, a composition may include a capsular saccharide from 1, 2, 3, 4, 5, 6, 7, 8, 9, 10, 11, 12, 13, 14, 15, 16, 17, 18, 19, 20, 21, 22, 23 or more different serotypes. Compositions which include at least serotype 6B saccharide are useful.

A useful combination of serotypes is a 7-valent combination e.g. including capsular saccharide from each of serotypes 4, 6B, 9V, 14, 18C, 19F, and 23F. Another useful combination is a 9-valent combination e.g. including capsular saccharide from each of serotypes 1, 4, 5, 6B, 9V, 14, 18C, 19F and 23F. Another useful combination is a 10-valent combination e.g. including capsular saccharide from each of serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; or 22F and 15B. A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F; 6A and 19A, etc.

Thus a useful 13-valent combination includes capsular saccharide from serotypes 1, 3, 4, 5, 6A, 6B, 7F, 9V, 14, 18C, 19 (or 19A), 19F and 23F e.g. prepared as disclosed in references 72 to 75. One such combination includes serotype 6B saccharide at about 8 µg/ml and the other 12 saccharides at concentrations of about 4 µg/ml each. Another such combination includes serotype 6A and 6B saccharides at about 8 µg/ml each and the other 11 saccharides at about 4 µg/ml each.

Suitable carrier proteins for conjugates include bacterial toxins, such as diphtheria or tetanus toxins, or toxoids or mutants thereof. These are commonly used in conjugate vaccines. For example, the CRM197 diphtheria toxin mutant is useful [76]. Other suitable carrier proteins include synthetic peptides [77,78], heat shock proteins [79,80], pertussis proteins [81,82], cytokines [83], lymphokines [83], hormones [83], growth factors [83], artificial proteins comprising multiple human CD4$^+$ T cell epitopes from various pathogen-derived antigens [84] such as N19 [85], protein D from *H. influenzae* [86-88], pneumolysin [89] or its non-toxic derivatives [90], pneumococcal surface protein PspA [91], iron-uptake proteins [92], toxin A or B from *C. difficile* [93], recombinant *Pseudomonas aeruginosa* exoprotein A (rEPA) [94], etc.

Particularly useful carrier proteins for pneumococcal conjugate vaccines are CRM197, tetanus toxoid, diphtheria toxoid and *H. influenzae* protein D. CRM197 is used in PREVNAR™. A 13-valent mixture may use CRM197 as the carrier protein for each of the 13 conjugates, and CRM197 may be present at about 55-60 µg/ml.

Where a composition includes conjugates from more than one pneumococcal serotype, it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates. Reference 95 describes potential advantages when using different carrier proteins in multivalent pneumococcal conjugate vaccines, but the PREVNAR™ product successfully uses the same carrier for each of seven different serotypes.

A carrier protein may be covalently conjugated to a pneumococcal saccharide directly or via a linker. Various linkers are known. For example, attachment may be via a carbonyl, which may be formed by reaction of a free hydroxyl group of a modified saccharide with CDI [96,97] followed by reaction with a protein to form a carbamate linkage. Carbodiimide condensation can be used [98]. An adipic acid linker can be used, which may be formed by coupling a free —NH$_2$ group (e.g. introduced to a saccharide by amination) with adipic acid (using, for example, diimide activation), and then coupling a protein to the resulting saccharide-adipic acid intermediate [99,100]. Other linkers include β-propionamido [101], nitrophenyl-ethylamine [102], haloacyl halides [103], glycosidic linkages [104], 6-aminocaproic acid [105], N-succinimidyl-3-(2-pyridyldithio)-propionate (SPDP) [106], adipic acid dihydrazide ADH [107], $C_4$ to $C_{12}$ moieties [108], etc.

Conjugation via reductive amination can be used. The saccharide may first be oxidised with periodate to introduce an aldehyde group which can then form a direct covalent linkage to a carrier protein by reductive amination e.g. to a lysine's ε-amino group. If the saccharide includes multiple aldehyde groups per molecule then this linkage technique can lead to a cross-linked product, where multiple aldehydes react with multiple carrier amines. This cross-linking conjugation technique is particularly useful for at least pneumococcal serotypes 4, 6B, 9V, 14, 18C, 19F and 23F.

A pneumococcal saccharide may comprise a full-length intact saccharide as prepared from pneumococcus, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. Depolymerisation can be used in order to provide an optimum chain length for immunogenicity and/or to reduce chain length for physical manageability of the saccharides. Where more than one pneumococcal serotype is used then it is possible to use intact saccharides for each serotype, fragments for each serotype, or to use intact saccharides for some serotypes and fragments for other serotypes.

Where a composition includes saccharide from any of serotypes 4, 6B, 9V, 14, 19F and 23F, these saccharides are preferably intact. In contrast, where a composition includes saccharide from serotype 18C, this saccharide is preferably depolymerised.

A serotype 3 saccharide may also be depolymerised, For instance, a serotype 3 saccharide can be subjected to acid hydrolysis for depolymerisation [72] e.g. using acetic acid. The resulting fragments may then be oxidised for activation (e.g. periodate oxidation, maybe in the presence of bivalent cations e.g. with MgCl$_2$), conjugated to a carrier (e.g. CRM197) under reducing conditions (e.g. using sodium cyanoborohydride), and then (optionally) any unreacted aldehydes in the saccharide can be capped (e.g. using sodium borohydride) [72]. Conjugation may be performed on lyophilized material e.g. after co-lyophilizing activated saccharide and carrier.

A serotype 1 saccharide may be at least partially de-O-acetylated e.g. achieved by alkaline pH buffer treatment [73] such as by using a bicarbonate/carbonate buffer. Such (partially) de-O-acetylated saccharides can be oxidised for activation (e.g. periodate oxidation), conjugated to a carrier (e.g.

CRM197) under reducing conditions (e.g. using sodium cyanoborohydride), and then (optionally) any unreacted aldehydes in the saccharide can be capped (e.g. using sodium borohydride) [73]. Conjugation may be performed on lyophilized material e.g. after co-lyophilizing activated saccharide and carrier.

A serotype 19A saccharide may be oxidised for activation (e.g. periodate oxidation), conjugated to a carrier (e.g. CRM197) in DMSO under reducing conditions, and then (optionally) any unreacted aldehydes in the saccharide can be capped (e.g. using sodium borohydride) [109]. Conjugation may be performed on lyophilized material e.g. after co-lyophilizing activated saccharide and carrier.

One or more pneumococcal capsular saccharide conjugates may be present in lyophilised form.

Pneumococcal conjugates can ideally elicit anticapsular antibodies that bind to the relevant saccharide e.g. elicit an anti-saccharide antibody level ≥0.20 μg/mL [110]. The antibodies may be evaluated by enzyme immunoassay (EIA) and/or measurement of opsonophagocytic activity (OPA). The EIA method has been extensively validated and there is a link between antibody concentration and vaccine efficacy.

Adjuvants

Compositions of the invention can include an adjuvant, such as (i) an oil-in-water emulsion (ii) at least one aluminium salt or (iii) at least one TLR agonist.

In some embodiments a composition includes a mixture of an aluminium salt and a TLR agonist, and the TLR agonist can be adsorbed to the aluminium salt to improve adjuvant effects [142]. This can lead to a better (stronger, or more quickly achieved) immune response and/or can permit a reduction in the amount of aluminium in the composition while maintaining an equivalent adjuvant effect.

Where a composition includes aluminium salt adjuvant(s) then between one and all of the immunogens in the composition can be adsorbed to the salt(s). Moreover, if the composition includes a TLR adjuvant then this can also be adsorbed to the salt(s), as discussed below.

Where a composition includes an aluminium salt adjuvant then preferably it does not also include an oil-in-water emulsion adjuvant. Conversely, where a composition includes an oil-in-water emulsion adjuvant then preferably it does not also include an aluminium salt adjuvant.

Oil-in-Water Emulsion Adjuvants

According to the invention's second aspect a vaccine is adjuvanted with an oil-in-water emulsion. Various such emulsions are known e.g. MF59 and AS03 are both authorised in Europe.

Useful emulsion adjuvants they typically include at least one oil and at least one surfactant, with the oil(s) and surfactant(s) being biodegradable (metabolisable) and biocompatible. The oil droplets in the emulsion generally have a sub-micron diameter, and these small sizes can readily be achieved with a microfluidiser to provide stable emulsions, or by alternative methods e.g. phase inversion. Emulsions in which at least 80% (by number) of droplets have a diameter of less than 220 nm are preferred, as they can be subjected to filter sterilization.

The emulsion can include oil(s) from an animal (such as fish) and/or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolisable and may therefore be used with the invention. The procedures for separation, purification, saponification and other means necessary for obtaining pure oils from animal sources are well known in the art.

Most fish contain metabolisable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred for use with the invention (see below). Squalane, the saturated analog to squalene, is also a useful oil. Fish oils, including squalene and squalane, are readily available from commercial sources or may be obtained by methods known in the art. Other preferred oils are the tocopherols (see below). Mixtures of oils can be used.

Preferred amounts of total oil (% by volume) in an adjuvant emulsion are between 1 and 20% e.g. between 2-10%. A squalene content of 5% by volume is particularly useful.

Surfactants can be classified by their 'HLB' (hydrophile/lipophile balance). Preferred surfactants of the invention have a HLB of at least 10 e.g. about 15. The invention can be used with surfactants including, but not limited to: the polyoxyethylene sorbitan esters surfactants (commonly referred to as the Tweens), especially polysorbate 20 or polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the Spans), such as sorbitan trioleate (Span 85) or sorbitan monolaurate.

Emulsions used with the invention preferably include non-ionic surfactant(s). Preferred surfactants for including in the emulsion are polysorbate 80 (polyoxyethylene sorbitan monooleate; Tween 80), Span 85 (sorbitan trioleate), lecithin or Triton X-100. Mixtures of surfactants can be used e.g. a mixture of polysorbate 80 and sorbitan trioleate. A combination of a polyoxyethylene sorbitan ester such as polysorbate 80 (Tween 80) and an octoxynol such as t-octylphenoxypolyethoxyethanol (Triton X-100) is also useful. Another useful combination comprises laureth 9 plus a polyoxyethylene sorbitan ester and/or an octoxynol. Where a mixture of surfactants is used then the HLB of the mixture is calculated according to their relative weightings (by volume) e.g. the preferred 1:1 mixture by volume of polysorbate 80 and sorbitan trioleate has a HLB of 8.4.

Preferred amounts of total surfactant (% by volume) in an adjuvant emulsion are between 0.1 and 2% e.g. between 0.25-2%. A total content of 1% by volume is particularly useful e.g. 0.5% by volume of polysorbate 80 and 0.5% by volume of sorbitan trioleate.

Useful emulsions can be prepared using known techniques e.g. see references 132 and 111-112117

Specific oil-in-water emulsion adjuvants useful with the invention include, but are not limited to:

- A submicron emulsion of squalene, polysorbate 80, and sorbitan trioleate. The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. This adjuvant is known as 'MF59' [118-120], as described in more detail in Chapter 10 of ref. 131 and chapter 12 of ref. 132. The MF59 emulsion advantageously includes citrate ions e.g. 10 mM sodium citrate buffer.
- An emulsion of squalene, a tocopherol, and polysorbate 80. The emulsion may include phosphate buffered saline. These emulsions may have from 2 to 10% squalene, from 2 to 10% tocopherol and from 0.3 to 3% polysorbate 80, and the weight ratio of squalene:tocopherol is preferably ≤1 (e.g. 0.90) as this can provide a more stable emulsion. Squalene and polysorbate 80 may be present volume ratio of about 5:2, or at a weight ratio of about 11:5. Thus the three components (squalene, tocopherol, polysorbate 80) may be present at a weight ratio of 1068:1186:485 or around 55:61:25. This adjuvant is known as 'AS03'. Another useful emulsion of this type may comprise, per human dose, 0.5-10 mg squalene, 0.5-11 mg tocopherol, and 0.1-4 mg polysorbate 80 [121] e.g. in the ratios discussed above.
- An emulsion in which a saponin (e.g. QuilA or QS21) and a sterol (e.g. a cholesterol) are associated as helical micelles [122].
- An emulsion having from 0.5-50% of an oil, 0.1-10% of a phospholipid, and 0.05-5% of a non-ionic surfactant. As described in reference 123, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [124]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [125]. Such emulsions may be lyophilized. The 'AF03' product is one such emulsion.

Preferred oil-in-water emulsions used with the invention comprise squalene and polysorbate 80.

The emulsions may be mixed with TdaP antigens during vaccine manufacture, or they may be mixed extemporaneously at the time of delivery. Thus, in some embodiments, the adjuvant and antigens may be kept separately in a packaged or distributed vaccine, ready for final formulation at the time of use. At the time of mixing (whether during bulk manufacture, or at the point of use) the antigen will generally be in an aqueous form, such that the final vaccine is prepared by mixing two liquids. The volume ratio of the two liquids for mixing can vary (e.g. between 5:1 and 1:5) but is generally about 1:1. If emulsion and antigen are stored separately in a kit then the product may be presented as a vial containing emulsion and a vial containing aqueous antigen, for mixing to give adjuvanted liquid vaccine (monodose or multi-dose).

Preferred emulsions of the invention include squalene oil. This is usually prepared from shark oil but alternative sources are known e.g. see references 126 (yeast) and 127 (olive oil). Squalene which contains less than 661 picograms of PCBs per gram of squalene (TEQ) is preferred for use with the invention, as disclosed in reference 128. The emulsions are preferably made from squalene of high purity e.g. prepared by double-distillation as disclosed in reference 129.

Where a composition includes a tocopherol, any of the α, β, γ, δ, ε or ζ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols have antioxidant properties that may help to stabilize the emulsions [130]. A preferred α-tocopherol is DL-α-tocopherol, and a preferred salt of this tocopherol is the succinate.

Aluminium Salt Adjuvants

Compositions of the invention can include an aluminium salt adjuvant. Aluminium salt adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 131, and chapter 4 of reference 132). The invention can use any of the "hydroxide" or "phosphate" salts that useful as adjuvants. Aluminium salts which include hydroxide ions are preferred if adsorption of a TLR agonist is desired as these hydroxide ions can readily undergo ligand exchange for adsorption of the TLR agonist. Thus preferred salts for adsorption of TLR agonists are aluminium hydroxide and/or aluminium hydroxyphosphate. These have surface hydroxyl moieties which can readily undergo ligand exchange with phosphorus-containing groups (e.g. phosphates, phosphonates) to provide stable adsorption. An aluminium hydroxide adjuvant is thus most preferred.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 131). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants e.g. with needle-like particles with diameters about 2 nm. The PZC of aluminium hydroxide adjuvants is typically about 11 i.e. the adjuvant itself has a positive surface charge at physiological pH. Adsorptive capacities of between 1.8-

2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate. They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 0.99. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls (chapter 9 of ref 131).

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate. Typical diameters of the particles are in the range 0.5-20 μm (e.g. about 5-10 μm) after any antigen adsorption. Adsorptive capacities of between 0.7-1.5 mg protein per mg Al$^{+++}$ at pH 7.4 have been reported for aluminium phosphate adjuvants.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

In solution both aluminium phosphate and hydroxide adjuvants tend to form stable porous aggregates 1-10 μm in diameter [133].

A composition can include a mixture of both an aluminium hydroxide and an aluminium phosphate, and components may be adsorbed to one or both of these salts.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

A composition of the invention ideally includes less than 0.85 mg Al$^{+++}$ per unit dose. In some embodiments of the invention a composition includes less than 0.5 mg Al$^{+++}$ per unit dose. The amount of Al$^{+++}$ can be lower than this e.g. <250 μg, <200 μg, <150 μg, <100 μg, <75 μg, <50 μg, <25 μg, <10 μg, etc.

Where compositions of the invention include an aluminium-based adjuvant, settling of components may occur during storage. The composition should therefore be shaken prior to administration to a patient. The shaken composition will be a turbid white suspension.

If a TLR agonist and an aluminium salt are both present, in general the weight ratio of the TLR agonist to Al$^{+++}$ will be less than 5:1 e.g. less than 4:1, less than 3:1, less than 2:1, or less than 1:1. Thus, for example, with an Al$^{+++}$ concentration of 0.5 mg/ml the maximum concentration of TLR agonist would be 2.5 mg/ml. But higher or lower levels can be used. A lower mass of TLR agonist than of Al$^{+++}$ can be most typical e.g. per dose, 100 μg of TLR agonist with 0.2 mg Al$^{+++}$, etc. For instance, the FENDRIX™ product includes 50 μg of 3d-MPL and 0.5 mg Al$^{+++}$ per dose.

TLR Agonists

In some embodiments a composition of the invention includes a TLR agonist i.e. a compound which can agonise a Toll-like receptor. Most preferably, a TLR agonist is an agonist of a human TLR. The TLR agonist can activate any of TLR1, TLR2, TLR3, TLR4, TLR5, TLR6, TLR7, TLR8, TLR9 or TLR11; preferably it can activate human TLR4 or human TLR7.

Agonist activity of a compound against any particular Toll-like receptor can be determined by standard assays. Companies such as Imgenex and Invivogen supply cell lines which are stably co-transfected with human TLR genes and NFκB, plus suitable reporter genes, for measuring TLR activation pathways. They are designed for sensitivity, broad working range dynamics and can be used for high-throughput screening. Constitutive expression of one or two specific TLRs is typical in such cell lines. See also reference 134. Many TLR agonists are known in the art e.g. reference 135 describes certain lipopeptide molecules that are TLR2 agonists, references 136 to 139 each describe classes of small molecule agonists of TLR7, and references 140 & 141 describe TLR7 and TLR8 agonists for treatment of diseases.

A TLR agonist used with the invention ideally includes at least one adsorptive moiety. The inclusion of such moieties in TLR agonists allows them to adsorb to insoluble aluminium salts (e.g. by ligand exchange or any other suitable mechanism) and improves their immunological behaviour [142]. Phosphorus-containing adsorptive moieties are particularly useful, and so an adsorptive moiety may comprise a phosphate, a phosphonate, a phosphinate, a phosphonite, a phosphinite, etc.

Preferably the TLR agonist includes at least one phosphonate group.

Thus, in preferred embodiments, a composition of the invention includes a TLR agonist (such as a TLR7 agonist) which includes a phosphonate group. This phosphonate group can allow adsorption of the agonist to an insoluble aluminium salt [142].

TLR agonists useful with the invention may include a single adsorptive moiety, or may include more than one e.g. between 2 and 15 adsorptive moieties. Typically a compound will include 1, 2 or 3 adsorptive moieties.

Phosphorus-containing TLR agonists useful with the invention can be represented by formula (A1):

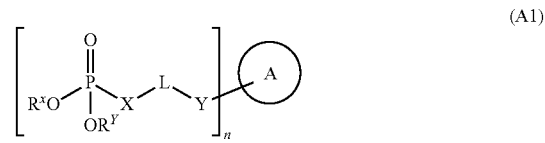

wherein:

R$^X$ and R$^Y$ are independently selected from H and C$_1$-C$_6$ alkyl;

X is selected from a covalent bond, O and NH;

Y is selected from a covalent bond, O, C(O), S and NH;

L is a linker e.g. selected from, C$_1$-C$_6$alkylene, C$_1$-C$_6$alkenylene, arylene, heteroarylene, C$_1$-C$_6$alkyleneoxy and —((CH$_2$)$_p$O)$_q$(CH$_2$)$_p$— each optionally substituted with 1 to 4 substituents independently selected from halo, OH, C$_1$-C$_4$alkyl, —OP(O)(OH)$_2$ and —P(O)(OH)$_2$;

each p is independently selected from 1, 2, 3, 4, 5 and 6;

q is selected from 1, 2, 3 and 4;

n is selected from 1, 2 and 3; and

A is a TLR agonist moiety.

In one embodiment, the TLR agonist according to formula (A1) is as follows: R$^X$ and R$^Y$ are H; X is O; L is selected from C$_1$-C$_6$ alkylene and —((CH$_2$)$_p$O)$_q$(CH$_2$)$_p$— each optionally substituted with 1 to 2 halogen atoms; p is selected from 1, 2 and 3; q is selected from 1 and 2; and n is 1. Thus in these embodiments the adsorptive moiety comprises a phosphate group.

In other embodiments, the TLR agonist according to formula (A1) is as follows: R$^X$ and R$^Y$ are H; X is a covalent bond; L is selected from C$_1$-C$_6$ alkylene and —((CH$_2$)$_p$O)$_q$(CH$_2$)$_p$— each optionally substituted with 1 to 2 halogen atoms; p is selected from 1, 2 or 3; q is selected from 1 or 2; and n is 1. Thus in these embodiments the adsorptive moiety comprises a phosphonate group.

Useful 'A' moieties for formula (A1) include, but are not limited to, radicals of any of the following compounds, defined herein or as disclosed in references 136, 137, 139, 140, 142 & 177:

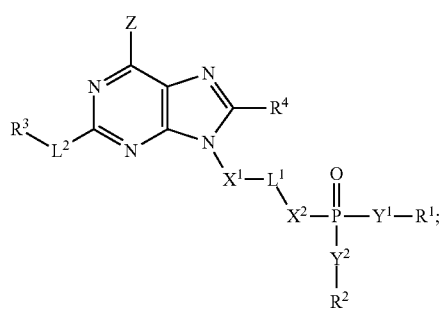

as defined on pages 2-7 of reference 137

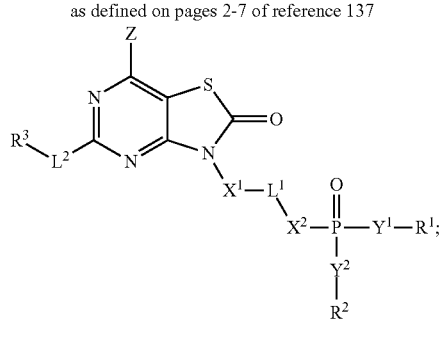

as defined on pages 2-5 & 7-8 of ref. 137

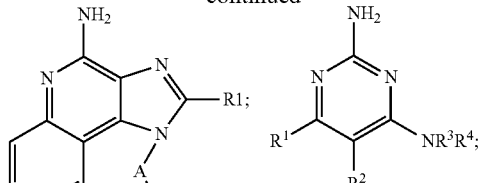

as defined on pages 6 & 7 of reference 136 as defined on pages 2 to 5 of reference 139

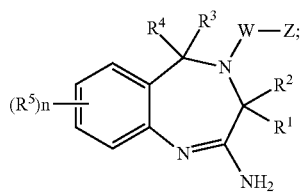

as defined on pages 5 to 6 of reference 140

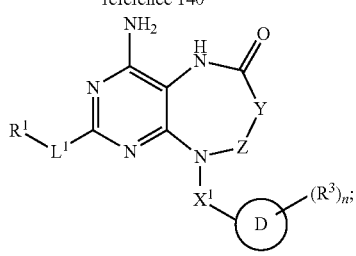

as defined on pages 2 to 3 of reference 177

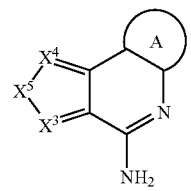

as defined on pages 2-4 of reference 138

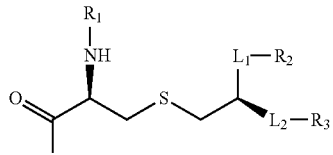

as defined in reference 143.

In some embodiments, the TLR agonist moiety 'A' has a molecular weight of less than 1000 Da. In some embodiments, the TLR agonist of formula (A1) has a molecular weight of less than 1000 Da.

Preferred TLR agonists are water-soluble. Thus they can form a homogenous solution when mixed in an aqueous buffer with water at pH 7 at 25° C. and 1 atmosphere pressure to give a solution which has a concentration of at least 50 μg/ml. The term "water-soluble" thus excludes substances that are only sparingly soluble under these conditions.

Useful TLR agonists include those having formula (C), (D), (E), (F), (G), (H), (I), (II), (J) or (K) as described in more detail below. Other useful TLR agonists are compounds 1 to 102 as defined in reference 142. Preferred TLR7 agonists have formula (K), such as compound K2 identified below. These can be used as salts e.g. the arginine salt of K2.

Preferred TLR4 agonists are analogs of monophosphoryl lipid A (MPL), as described in more detail below. For instance, a useful TLR4 agonist is a 3d-MPL.

A composition of the invention can include more than one TLR agonist. These two agonists are different from each other and they can target the same TLR or different TLRs. Both agonists can be adsorbed to an aluminium salt.

It is preferred that at least 50% (by mass) of any TLR agonist(s) in the composition is adsorbed to an aluminium salt (if present) e.g. ≥60%, ≥70%, ≥80%, ≥85%, ≥90%, ≥92%, ≥94%, ≥95%, ≥96%, ≥97%, ≥98%, ≥99%, or even 100%.

Where a composition of the invention includes a TLR agonist adsorbed to a metal salt, and also includes a buffer, it is preferred that the concentration of any phosphate ions in the buffer should be less than 50 mM (e.g. between 1-15 mM) as a high concentration of phosphate ions can cause desorption. Use of a histidine buffer is preferred.

Formulae (C), (D), (E) and (H)—TLR7 Agonists

The TLR agonist can be a compound according to any of formulae (C), (D), (E), and (H):

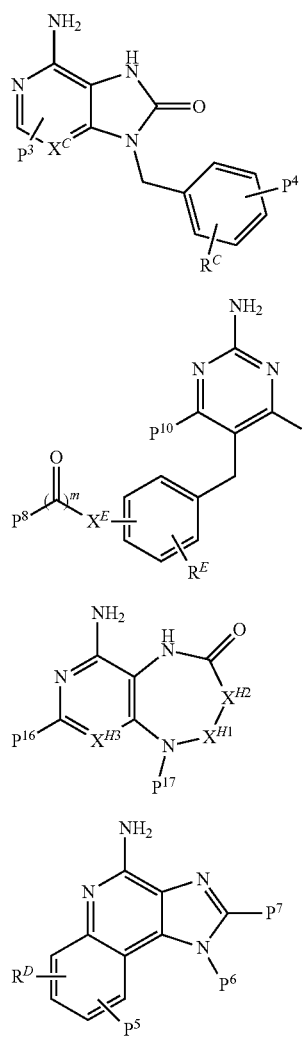

wherein:

(a) $P^3$ is selected from H, $C_1$-$C_6$alkyl, $CF_3$, and —$((CH_2)_pO)_q(CH_2)_pO_s$— and —Y-L-X—P(O)(OR$^X$)(OR$^Y$); and $P^4$ is selected from H, $C_1$-$C_6$alkyl, —$C_1$-$C_6$alkylaryl and —Y-L-X—P(O)(OR$^X$)(OR$^Y$); with the proviso that at least one of $P^3$ and $P^4$ is —Y-L-X—P(O)(OR$^X$)(OR$^Y$), (b) $P^5$ is selected from H, $C_1$-$C_6$alkyl, and —Y-L-X—P(O)(OR$^X$)(OR$^Y$); $P^6$ is selected from H, $C_1$-$C_6$alkyl each optionally substituted with 1 to 3 substituents selected from $C_1$-$C_4$alkyl and OH, and —Y-L-X—P(O)(OR$^X$)(OR$^Y$); and $P^7$ is selected from H, $C_1$-$C_6$alkyl, —$((CH_2)_pO)_q(CH_2)_pO_s$—, —NH$C_1$-$C_6$alkyl and —Y-L-X—P(O)(OR$^X$)(OR$^Y$); with the proviso that at least one of $P^5$, $P^6$ and $P^7$ is —Y-L-X—P(O)(OR$^X$)(OR$^Y$);

(c) $P^8$ is selected from H, $C_1$-$C_6$alkyl, $C_1$-$C_6$alkoxy, —NH$C_1$-$C_6$alkyl each optionally substituted with OH, and —Y-L-X—P(O)(OR$^X$)(OR$^Y$); and $P^9$ and $P^{10}$ are each independently selected from H, $C_1$-$C_6$alkyl, $C_1$-$C_6$alkoxy, —NH$C_1$-$C_6$alkyl each optionally substituted with OH and $C_1$-$C_6$alkyl, and —Y-L-X—P(O)(OR$^X$)(OR$^Y$); with the proviso that at least one of $P^8$, $P^9$ or $P^{10}$ is —Y-L-X—P(O)(OR$^X$)(OR$^Y$);

(d) $P^{16}$ and each $P^{18}$ are each independently selected from H, $C_1$-$C_6$alkyl, and —Y-L-X—P(O)(OR$^X$)(OR$^Y$); $P^{17}$ is selected from H, $C_1$-$C_6$alkyl, aryl, heteroaryl, $C_1$-$C_6$alkylaryl, $C_1$-$C_6$alkyl heteroaryl, $C_1$-$C_6$alkylaryl-Y-L-X—P(O)(OR$^X$)(OR$^Y$) and —Y-L-X—P(O)(OR$^X$)(OR$^Y$), each optionally substituted with 1 to 2 substituents selected from $C_1$-$C_6$alkyl or heterocyclyl with the proviso that at least one of $P^{16}$, $P^{17}$ or a $P^{18}$ contains a —Y-L-X—P(O)(OR$^X$)(OR$^Y$) moiety;

$R^X$ and $R^Y$ are independently selected from H and $C_1$-$C_6$alkyl;

$R^C$, $R^D$ and $R^H$ are each independently selected from H and $C_1$-$C_6$alkyl;

$X^C$ is selected from CH and N;

$R^E$ is selected from H, $C_1$-$C_6$alkyl, $C_1$-$C_6$alkoxy, $C(O)C_1$-$C_6$alkyl, halogen and —$((CH_2)_pO)_q(CH_2)_p$—;

$X^E$ is selected from a covalent bond, $CR^{E2}R^{E3}$ and $NR^{E4}$;

$R^{E2}$, $R^{E3}$ and $R^{E4}$ are independently selected from H and $C_1$-$C_6$alkyl;

$X^{H1}$-$X^{H2}$ is selected from —$CR^{H2}R^{H3}$—, —$CR^{H2}R^{H3}$—$CR^{H2}R^{H3}$—, —$C(O)CR^{H2}R^{H3}$—, —$C(O)CR^{H2}R^{H3}$—, —$CR^{H2}R^{H3}C(O)$—, —$NR^{H4}C(O)$—, $C(O)NR^{H4}$—, $CR^{H2}R^{H3}S(O)_2$ and —$CR^{H2}$=$CR^{H2}$—;

$R^{H2}$, $R^{H3}$ and $R^{H4}$ are each independently selected from H, $C_1$-$C_6$alkyl and $P^{18}$;

$X^{H3}$ is selected from N and CN;

X is selected from a covalent bond, O and NH;

Y is selected from a covalent bond, O, C(O), S and NH;

L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;

m is selected from 0 or 1;

each p is independently selected from 1, 2, 3, 4, 5 and 6;

q is selected from 1, 2, 3 and 4; and s is selected from 0 and 1.

Formula (G)—TLR8 Agonist

The TLR agonist can be a compound according to formula (G):

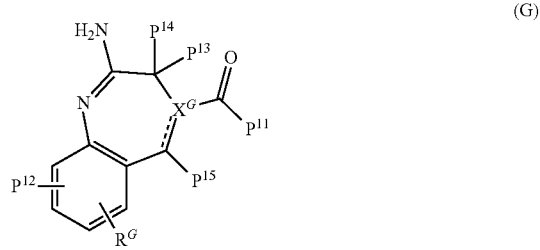

wherein:
P¹¹ is selected from H, $C_1$-$C_6$alkyl, $C_1$-$C_6$ alkoxy, $NR^V R^W$ and —Y-L-X—P(O)($OR^X$)($OR^Y$);
P¹² is selected from H, $C_1$-$C_6$alkyl, aryl optionally substituted by —C(O)$NR^V R^W$, and —Y-L-X—P(O)($OR^X$)($OR^Y$);
P¹³, P¹⁴ and P¹⁵ are independently selected from H, $C_1$-$C_6$alkyl, $C_1$-$C_6$ alkoxy and —Y-L-X—P(O)($OR^X$)($OR^Y$);
with the proviso that at least one of P¹¹, P¹², P¹³, P¹⁴ or P¹⁵ is —Y-L-X—P(O)($OR^X$)($OR^Y$);
$R^V$ and $R^W$ are independently selected from H, $C_1$-$C_6$alkyl or together with the nitrogen atom to which they are attached form a 4 to 7 remembered heterocyclic ring;
$X^G$ is selected from C, CH and N;
----- represents an optional double bond, wherein $X^G$ is C if ----- is a double bond; and
$R^G$ is selected from H and $C_1$-$C_6$alkyl;
X is selected from a covalent bond, O and NH;
Y is selected from a covalent bond, O, C(O), S and NH;
L is selected from, a covalent bond $C_1$-$C_6$alkylene, $C_1$-$C_6$alkenylene, arylene, heteroarylene, $C_1$-$C_6$alkyleneoxy and —(($CH_2$)$_p$O)$_q$($CH_2$)$_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6 and
q is selected from 1, 2, 3 and 4.

Formulae (I) and (II)—TLR7 Agonists [137]

The TLR agonist can be a compound according to formula (I) or formula (II):

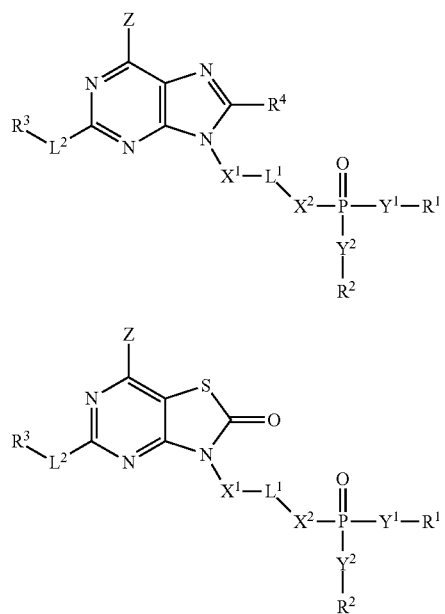

wherein:
Z is —$NH_2$ or —OH;
X¹ is alkylene, substituted alkylene, alkenylene, substituted alkenylene, alkynylene, substituted alkynylene, carbocyclylene, substituted carbocyclylene, heterocyclylene, or substituted heterocyclylene;
L¹ is a covalent bond, arylene, substituted arylene, heterocyclylene, substituted heterocyclylene, carbocyclylene, substituted carbocyclylene, —S—, —S(O)—, S(O)$_2$, —$NR^5$—, or —O—
X² is a covalent bond, alkylene, or substituted alkylene;
L² is $NR^5$—, —N($R^5$)C(O)—, —O—, —S—, —S(O)—, S(O)$_2$, or a covalent bond;
$R^3$ is H, alkyl, substituted alkyl, heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl;
Y¹ and Y² are each independently a covalent bond, —O— or —$NR^5$—; or —Y¹—$R^1$ and —Y²—$R^2$ are each independently-O—N=C($R^6 R^7$);
$R^1$ and $R^2$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^5$, -(substituted alkylene)-C(O)—O—$R^5$, -alkylene-O—C(O)—$R^5$, -(substituted alkylene)-O—C(O)—$R^5$, -alkylene-O—C(O)—O—$R^5$, or -(substituted alkylene)-O—C(O)—O—$R^5$
$R^4$ is H, halogen, —OH, —O-alkyl, —O-alkylene-O—C(O)—O—$R^5$, —O—C(O)—O—$R^5$, —SH, or —NH($R^5$);
each $R^5$, $R^6$, and $R^7$ are independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

Formula (J)—TLR2 Agonists [143]

The TLR agonist can be a compound according to formula (J):

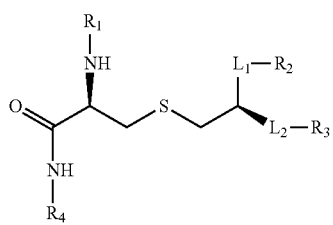

wherein:
$R^1$ is H, —C(O)—$C_7$-$C_{18}$alkyl or —C(O)—$C_1$-$C_6$alkyl;
$R^2$ is $C_7$-$C_{18}$alkyl;
$R^3$ is $C_7$-$C_{18}$alkyl;
$L_1$ is —$CH_2$OC(O)—, —$CH_2$O—, —$CH_2 NR^7$C(O)— or —$CH_2$OC(O)$NR^7$—;
$L_2$ is —OC(O)—, —O—, —$NR^7$C(O)— or —OC(O)$NR^7$—;
$R^4$ is -$L_3 R^5$ or -$L_4 R^5$;
$R^5$ is —N($R^7$)$_2$, —$OR^7$, —P(O)($OR^7$)$_2$, —C(O)$OR^7$, —$NR^7$C(O)$L_3 R^8$, —$NR^7$C(O)$L_4 R^8$, —$OL_3 R^6$, —C(O)$NR^7 L_3 R^8$, —C(O)$NR^7 L_4 R^8$, —S(O)$_2 OR^7$, —OS(O)$_2 OR^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of $R^5$ are each unsubstituted or the aryl, heteroaryl, cycloalkyl and heterocycloalkyl of $R^5$ are each substituted with 1 to 3 substituents independently selected from —$OR^9$, —$OL_3R^6$, —$OL_4R^6$, —$OR^7$, and —$C(O)OR^7$;

$L_3$ is a $C_1$-$C_{10}$alkylene, wherein the $C_1$-$C_{10}$alkylene of $L_3$ is unsubstituted, or the $C_1$-$C_{10}$alkylene of $L_3$ is substituted with 1 to 4 $R^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloakyl;

$L_4$ is —$((CR^7R^7)_pO)_q(CR^{10}R^{10})_p$— or —$(CR^{11}R^{11})((CR^7R^7)_pO)_q(CR^{10}R^{10})_p$—, wherein each $R^{11}$ is a $C_1$-$C_6$alkyl groups which together, along with the carbon atom they are attached to, form a $C_3$-$C_8$cycloakyl;

each $R^6$ is independently selected from halo, $C_1$-$C_6$alkyl, $C_1$-$C_6$alkyl substituted with 1-2 hydroxyl groups, —$OR^7$, —$N(R^7)_2$, —$C(O)OH$, —$C(O)N(R^7)_2$, —$P(O)(OR^7)_2$, a $C_6$aryl, a $C_{10}$aryl and a $C_{14}$aryl;

each $R^7$ is independently selected from H and $C_1$-$C_6$alkyl;

$R^8$ is selected from —$SR^7$, —$C(O)OH$, —$P(O)(OR^7)_2$, and a 5 to 6 ring membered heterocycloalkyl containing 1 to 3 heteroatoms selected from O and N;

$R^9$ is phenyl;

each $R^{10}$ is independently selected from H and halo;

each p is independently selected from 1, 2, 3, 4, 5 and 6, and q is 1, 2, 3 or 4.

Preferably $R^5$ is $P(O)(OR^7)_2$, —$NR^7C(O)L_3$-$P(O)(OR^7)_2$, —$NR^7C(O)L_4$-$P(O)(OR^7)_2$, —$OL_3$-$P(O)(OR^7)_2$, —$C(O)NR^7L_3$-$P(O)(OR^7)_2$, or —$C(O)NR^7L_4$-$P(O)(OR^7)_2$.

In some embodiments of (J), $R_1$ is H. In other embodiments of (J), $R_1$ is —$C(O)$—$C_{15}$alkyl;

In some embodiments of (J): (i) $L_1$ is —$CH_2OC(O)$— and $L_2$ is —$OC(O)$—, —$O$—, —$NR^7C(O)$— or —$OC(O)NR^7$—; or (ii) or $L_1$ is —$CH_2O$— and $L_2$ is —$OC(O)$—, —$O$—, —$NR^7C(O)$— or —$OC(O)NR^7$—; or (iii) $L_1$ is —$CH_2NR^7C(O)$— and $L_2$ is —$OC(O)$—, —$O$—, —$NR^7C(O)$— or —$OC(O)NR^7$—; or (iv) $L_1$ is —$CH_2OC(O)NR^7$— and $L_2$ is —$OC(O)$—, —$O$—, $NR^7C(O)$— or —$OC(O)NR^7$—.

In some embodiments of (J): (i) $L_1$ is —$CH_2OC(O)$— and $L_2$ is —$OC(O)$—; or (ii) $L_1$ is —$CH_2O$— and $L_2$ is —$O$—; or (iii) $L_1$ is —$CH_2O$— and $L_2$ is —$NHC(O)$—; or (iv) $L_1$ is —$CH_2OC(O)NH$— and $L_2$ is —$OC(O)NH$—.

In some embodiments of (J), (i) $R^2$ is —$C_{11}$ alkyl and $R^3$ is —$C_{11}$ alkyl; or (ii) $R^2$ is —$C_{16}$alkyl and $R^3$ is —$C_{16}$alkyl; or (iii) $R^2$ is —$C_{16}$alkyl and $R^3$ is —$C_{11}$ alkyl; or (iv) $R^2$ is —$C_{12}$alkyl and $R^3$ is —$C_{12}$alkyl; or (v) $R^2$ is —$C_7$alkyl and $R^3$ is —$C_7$alkyl; or (vi) $R^2$ is —$C_9$alkyl and $R^3$ is —$C_9$alkyl; or (vii) $R^2$ is —$C_8$alkyl and $R^3$ is —$C_8$alkyl; or (viii) $R^2$ is —$C_{13}$alkyl and $R^3$ is —$C_{13}$alkyl; or (ix) $R^2$ is —$C_{12}$alkyl and $R^3$ is —$C_{11}$ alkyl; or (x) $R^2$ is —$C_{12}$alkyl and $R^3$ is —$C_{12}$alkyl; or (xi) $R^2$ is —$C_{10}$alkyl and $R^3$ is —$C_{10}$alkyl; or (xii) $R^2$ is —$C_{15}$alkyl and $R^3$ is —$C_{15}$alkyl.

In some embodiments of (J), $R^2$ is —$C_{11}$ alkyl and $R^3$ is —$C_{11}$ alkyl.

In some embodiments of (J), $L_3$ is a $C_1$-$C_{10}$alkylene, wherein the $C_1$-$C_{10}$alkylene of $L_3$ is unsubstituted or is substituted with 1 to 4 $R^6$ groups.

In some embodiments of (J): $L_4$ is —$((CR^7R^7)_pO)_q(CR^{10}R^{10})_p$—; each $R^{10}$ is independently selected from H and F; and each p is independently selected from 2, 3, and 4.

In some embodiments of (J), each $R^6$ is independently selected from methyl, ethyl, i-propyl, i-butyl, —$CH_2OH$, —OH, —F, —$NH_2$, —$C(O)OH$, —$C(O)NH_2$, —$P(O)(OH)_2$ and phenyl.

In some embodiments of (J), each $R^7$ is independently selected from H, methyl and ethyl.

TLR4 Agonists

Compositions of the invention can include a TLR4 agonist, and most preferably an agonist of human TLR4. TLR4 is expressed by cells of the innate immune system, including conventional dendritic cells and macrophages [144]. Triggering via TLR4 induces a signalling cascade that utilizes both the MyD88- and TRIF-dependent pathways, leading to NF-κB and IRF3/7 activation, respectively. TLR4 activation typically induces robust IL-12p70 production and strongly enhances Th1-type cellular and humoral immune responses.

Various useful TLR4 agonists are known in the art, many of which are analogs of endotoxin or lipopolysaccharide (LPS). For instance, the TLR4 agonist can be:

(i) 3d-MPL (i.e. 3-O-deacylated monophosphoryl lipid A; also known as 3-de-O-acylated monophosphoryl lipid A or 3-O-desacyl-4'-monophosphoryl lipid A). This derivative of the monophosphoryl lipid A portion of endotoxin has a de-acylated position 3 of the reducing end of glucosamine. It has been prepared from a heptoseless mutant of *Salmonella minnesota*, and is chemically similar to lipid A but lacks an acid-labile phosphoryl group and a base-labile acyl group. Preparation of 3d-MPL was originally described in ref. 145, and the product has been manufactured and sold by Corixa Corporation. It is present in GSK's 'AS04' adjuvant. Further details can be found in references 146 to 149.

(ii) glucopyranosyl lipid A (GLA) [150] or its ammonium salt:

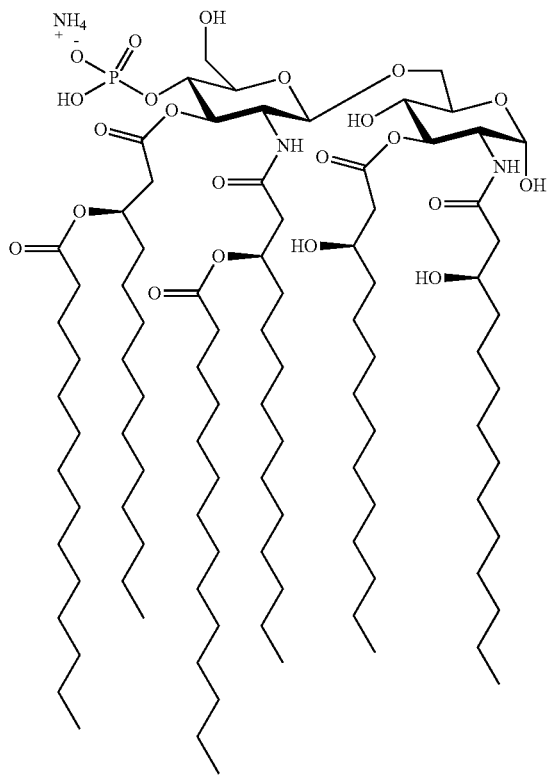

(iii) an aminoalkyl glucosaminide phosphate, such as RC-529 or CRX-524 [151-153]. RC-529 and CRX-524 have the following structure, differing by their $R_2$ groups:

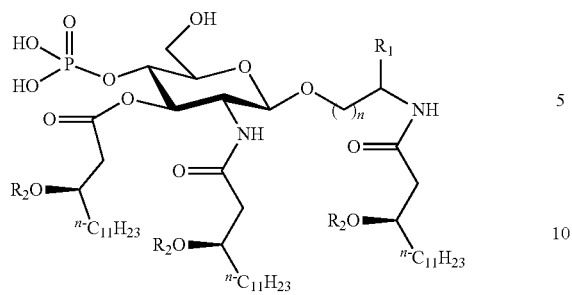
R₁ = H, R₂ = n-C₁₃H₂₇CO, n = 1 (RC-529)
R₁ = H, R₂ = n-C₉H₁₉CO, n = 1 (CRX-524)
(iv) compounds containing lipids linked to a phosphate-containing acyclic backbone, such as the TLR4 antagonist E5564 [154,155]:
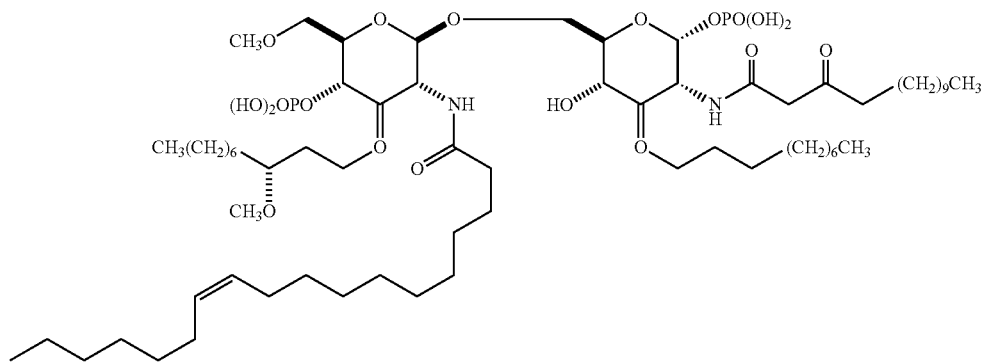
(v) A compound of formula I, II or III as defined in reference 156, or a salt thereof, such as compounds 'ER 803058', 'ER 803732', 'ER 804053', 'ER 804058', 'ER 804059', 'ER 804442', 'ER 804680', 'ER 803022', 'ER 804764' or 'ER 804057'. ER 804057 is also known as E6020 and it has the following structure:
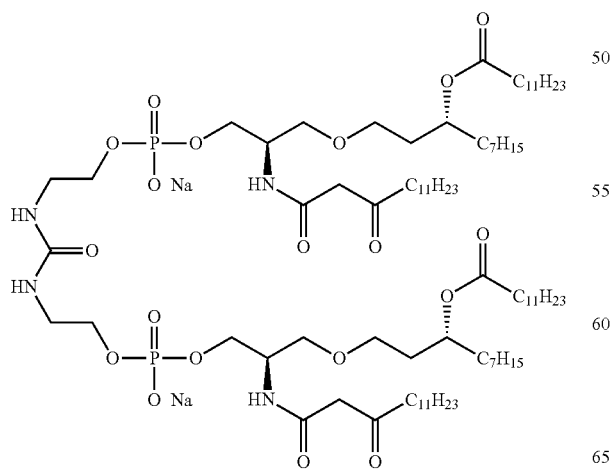

whereas ER 803022 has the following structure:

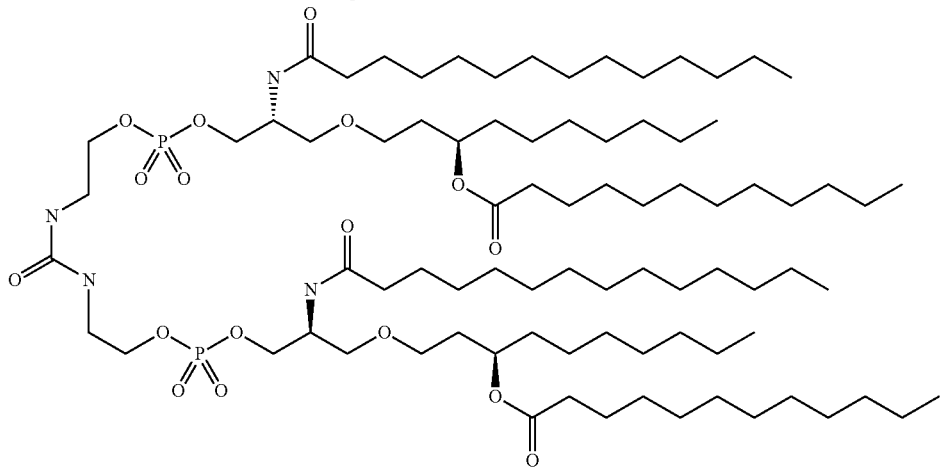

(vi) One of the polypeptide ligands disclosed in reference 157.

Any of these TLR4 agonists can be used with the invention.

A composition of the invention can include an aluminium salt to which the TLR4 agonist is adsorbed. TLR4 agonists with adsorptive properties typically include a phosphorus-containing moiety which can undergo ligand exchange with surface groups on an aluminium salt, and particularly with a salt having surface hydroxide groups. Thus a useful TLR4 agonist may include a phosphate, a phosphonate, a phosphinate, a phosphonite, a phosphinite, a phosphate, etc. Preferred TLR4 agonists include at least one phosphate group [142] e.g. the agonists (i) to (v) listed above.

The preferred TLR4 agonist for use with the invention is 3d-MPL. This can be adsorbed to an aluminium phosphate adjuvant, to an aluminium hydroxide adjuvant, or to a mixture of both [158].

3d-MPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula -O—CO—CH$_2$—CR$^3$R$^{3'}$. A representative structure is:

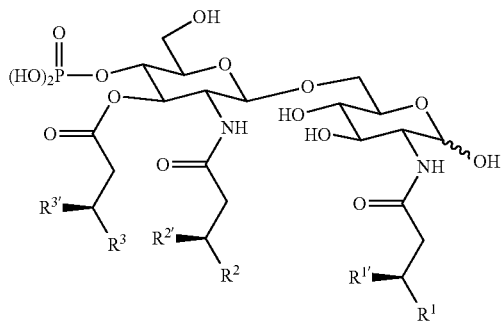

Groups $R^1$, $R^2$ and $R^3$ are each independently —(CH$_2$)$_n$—CH$_3$. The value of n is preferably between 8 and 16, more preferably between 9 and 12, and is most preferably 10.

Groups $R^{1'}$, $R^{2'}$ and $R^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14.

At the 2 position, m is preferably 14. At the 2' position, m is preferably 10. At the 3' position, m is preferably 12. Groups $R^{1'}$, $R^{2'}$ and $R^{3'}$ are thus preferably-O-acyl groups from dodecanoic acid, tetradecanoic acid or hexadecanoic acid.

When all of $R^{1'}$, $R^{2'}$ and $R^{3'}$ are —H then the 3d-MPL has only 3 acyl chains (one on each of positions 2, 2' and 3'). When only two of $R^{1'}$, $R^{2'}$ and $R^{3'}$ are —H then the 3d-MPL can have 4 acyl chains. When only one of $R^{1'}$, $R^{2'}$ and $R^{3'}$ is H then the 3d-MPL can have 5 acyl chains. When none of $R^{1'}$, $R^{2'}$ and $R^{3'}$ is —H then the 3d-MPL can have 6 acyl chains. The 3d-MPL used according to the invention can be a mixture of these forms, with from 3 to 6 acyl chains, but it is preferred to include 3d-MPL with 6 acyl chains in the mixture, and in particular to ensure that the 6 acyl chain form makes up at least 10% by weight of the total 3d-MPL e.g. ≥20%, ≥30%, ≥40%, ≥50% or more. 3d-MPL with 6 acyl chains has been found to be the most adjuvant-active form.

Thus the most preferred form of 3d-MPL for use with the invention is:

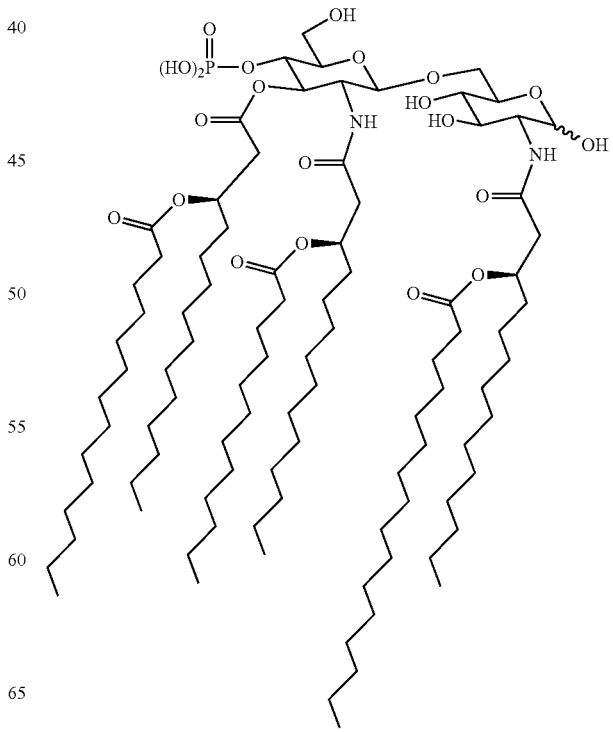

Where 3d-MPL is used in the form of a mixture then references to amounts or concentrations of 3d-MPL in compositions of the invention refer to the combined 3d-MPL species in the mixture.

Typical compositions include 3d-MPL at a concentration of between 25 µg/ml and 200 µg/ml e.g. in the range 50-150 µg/ml, 75-125 µg/ml, 90-110 µg/ml, or about 100 µg/ml. It is usual to administer between 25-75 µg of 3d-MPL per dose e.g. between 45-55 µg, or about 50 µg 3d-MPL per dose.

In aqueous conditions, 3d-MPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3d-MPL) are preferred for use according to the invention because of their superior activity [159]. Preferred particles have a mean diameter less than 150 nm, more preferably less than 120 nm, and can even have a mean diameter less than 100 nm. In most cases, however, the mean diameter will not be lower than 50 nm. Where 3d-MPL is adsorbed to an aluminum salt then it may not be possible to measure the 3D-MPL particle size directly, but particle size can be measured before adsorption takes place. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

Formula (K) [160]

The TLR agonist can be a compound according to formula (K):

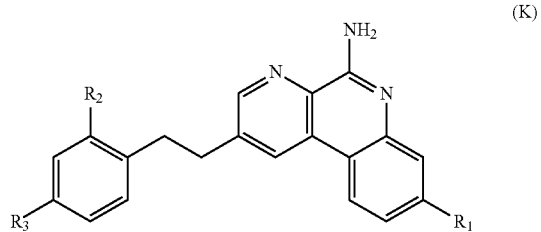

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —P(O)($OR^9$)$_2$;
$R^6$ is —$CF_2$P(O)($OR^9$)$_2$ or —C(O)$OR^{10}$;

$R^7$ is —$CF_2$P(O)($OR^9$)$_2$ or —C(O)$OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and
q is 1, 2, 3 or 4.

The compound of formula (K) is preferably of formula (K'):

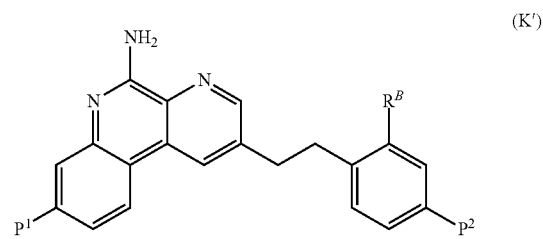

wherein:
$P^1$ is selected from H, $C_1$-$C_6$alkyl optionally substituted with COOH and —Y-L-X—P(O)($OR^X$)($OR^Y$);
$P^2$ is selected from H, $C_1$-$C_6$alkyl, $C_1$-$C_6$alkoxy and —Y-L-X—P(O)($OR^X$)($OR^Y$);
with the proviso that at least one of $P^1$ and $P^2$ is —Y-L-X—P(O)($OR^X$)($OR^Y$);
$R^B$ is selected from H and $C_1$-$C_6$alkyl;
$R^X$ and $R^Y$ are independently selected from H and $C_1$-$C_6$alkyl;
X is selected from a covalent bond, O and NH;
Y is selected from a covalent bond, O, C(O), S and NH;
L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6; and
q is selected from 1, 2, 3 and 4.

In some embodiments of formula (K'): $P^1$ is selected from $C_1$-$C_6$alkyl optionally substituted with COOH and —Y-L-X—P(O)($OR^X$)($OR^Y$); $P^2$ is selected from $C_1$-$C_6$alkoxy and —Y-L-X—P(O)($OR^X$)($OR^Y$); $R^B$ is $C_1$-$C_6$alkyl; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

A preferred TLR7 agonist of formula K is 3-(5-amino-2-(2-methyl-4-(2-(2-(2-phosphonoethoxy)ethoxy)ethoxy) phenethyl)benzo[f]-[1,7]naphthyridin-8-yl)propanoic acid, referred to herein as compound "K2":

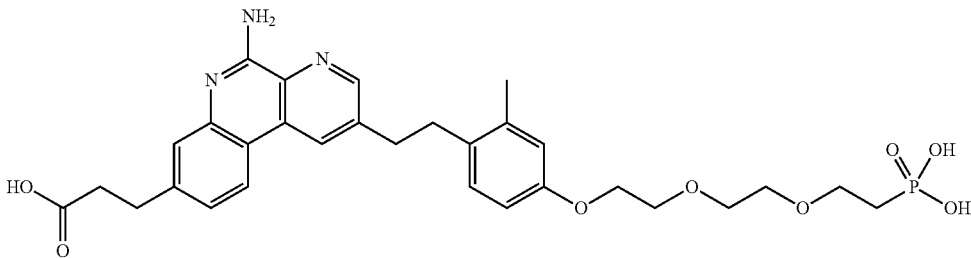 [SMILES: Cc1cc(OCCOCCOCCP(=O)(O)O)ccc1CCc1cnc2c(N)nc3cc(CCC(=O)O)ccc3c2c1]

The K2 compound can also be used as an arginine salt monohydrate.

Formula (F)—TLR7 Agonists [138]

The TLR agonist can be a compound according to formula (F):

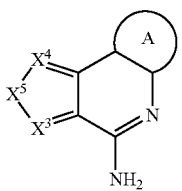

(F)

wherein:
$X^3$ is N;
$X^4$ is N or $CR^3$
$X^5$ is —$CR^4$=$CR^5$—;
$R^1$ and $R^2$ are H;
$R^3$ is H;
$R^4$ and $R^5$ are each independently selected from H, halogen, —C(O)O$R^7$, —C(O)$R^7$, —C(O)N($R^{11}R^{12}$), —N($R^{11}R^{12}$), —N($R^9$)$_2$, —NHN($R^9$)$_2$, S$R^7$, —(CH$_2$)$_n$O$R^7$, —(CH$_2$)$_n$$R^7$, -L$R^8$, -L$R^{10}$, —OL$R^8$, —OL$R^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —NO$_2$, —$R^7$, —O$R^8$, —C(O)$R^8$, —OC(O)$R^8$, —C(O)O$R^8$, —N($R^9$)$_2$, —P(O)(O$R^8$)$_2$, —OP(O)(O$R^8$)$_2$, —P(O)(O$R^{10}$)$_2$, —OP(O)(O$R^{10}$)$_2$, —C(O)N($R^9$)$_2$, —S(O)$_2$$R^8$, —S(O)$R^8$, —S(O)$_2$N($R^9$)$_2$, and —N$R^9$S(O)$_2$$R^8$;

or, $R^3$ and $R^4$, or $R^4$ and $R^5$, or $R^5$ and $R^6$, when present on adjacent ring atoms, can optionally be linked together to form a 5-6 membered ring, wherein the 5-6 membered ring is optionally substituted with $R^7$;

each L is independently selected from a bond, —O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —O$R^8$, —N($R^9$)$_2$, —P(O)(O$R^8$)$_2$, —OP(O)(O$R^8$)$_2$, —P(O)(O$R^{10}$)$_2$, and —OP(O)(O$R^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -L$R^9$, -LO$R^9$, —OL$R^9$, -L$R^{10}$, -LO$R^{10}$, —OL$R^{10}$, -L$R^8$, -LO$R^8$, —OL$R^8$, -LS$R^8$, -LS$R^{10}$, -LC(O)$R^8$, -OLC(O)$R^8$, -LC(O)O$R^8$, -LC(O)$R^{10}$, -LOC(O)O$R^8$, -LC(O)N$R^9R^{11}$, -LC(O)N$R^9R^8$, -LN($R^9$)$_2$, -LN$R^9R^8$, -LN$R^9R^{10}$, -LC(O)N($R^9$)$_2$, -LS(O)$_2R^8$, -LS(O)$R^8$, -LC(O)N$R^8$OH, -LN$R^9$C(O)$R^8$, -LN$R^9$C(O)O$R^8$, -LS(O)$_2$N($R^9$)$_2$, —OLS(O)$_2$N($R^9$)$_2$, -LN$R^9$S(O)$_2R^8$, -LC(O)N$R^9$LN($R^9$)$_2$, -LP(O)(O$R^8$)$_2$, -LOP(O)(O$R^8$)$_2$, -LP(O)(O$R^{10}$)$_2$ and —OLP(O)(O$R^{10}$)$_2$;

each $R^8$ is independently selected from H, —CH($R^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —O$R^{11}$, —S$R^{11}$, —C(O)$R^{11}$, —OC(O)$R^{11}$, —C(O)N($R^9$)$_2$, —C(O)O$R^{11}$, —N$R^9$C(O)$R^{11}$, —N$R^9R^{10}$, —N$R^{11}R^{12}$, —N($R^9$)$_2$, —O$R^9$, —O$R^{10}$, —C(O)N$R^{11}R^{12}$, —C(O)N$R^{11}$OH, —S(O)$_2R^{11}$, —S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$;

each $R^9$ is independently selected from H, —C(O)$R^8$, —C(O)O$R^8$, —C(O)$R^{10}$, —C(O)O$R^{10}$, —S(O)$_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —O$R^{11}$, —S$R^{11}$, —C(O)$R^{11}$, OC(O)$R^{11}$, —C(O)O$R^{11}$, —N$R^{11}R^{12}$, —C(O)N$R^{11}R^{12}$, —C(O)N$R^{11}$OH, —S(O)$^2R^{11}$, —S(O)$R^{11}$, —S(O)$_2$N$R^{11}R^{12}$, —N$R^{11}$S(O)$_2R^{11}$, —P(O)(O$R^{11}$)$_2$ and —OP(O)(O$R^{11}$)$_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$.—$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, $C(O)R^8$, $OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

ring A is an aryl or a heteroaryl, wherein the aryl and heteroaryl groups of Ring A are optionally substituted with 1 to 3 $R^4$ groups, wherein each $R^4$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —C(=NH)—$N(R^9)_2$, and —$(CH_2)_nNHC(O)R^8$ or two adjacent $R^4$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

Formulae (C), (D), (E), (G) and (H)

As discussed above, the TLR agonist can be of formula (C), (D), (E), (G) or (H).

The 'parent' compounds of formulae (C), (D), (E) and (H) are useful TLR7 agonists (see references 136-139 and 161-177) but are preferably modified herein by attachment of a phosphorus-containing moiety.

In some embodiments of formulae (C), (D) and (E) the compounds have structures according to formulae (C'), (D') and (E'), shown below:

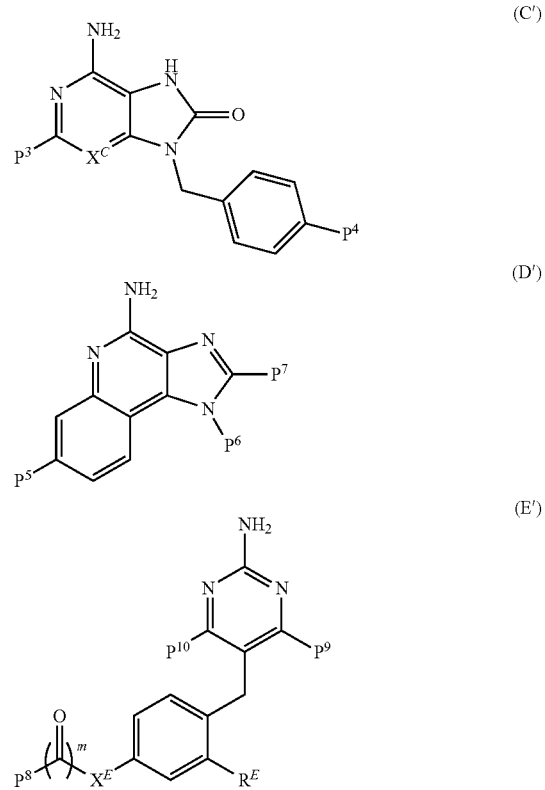

The embodiments of the invention of formulae (C), (D), (E) and (H) also apply to formulae (C'), (D'), (E') and (H').

In some embodiments of formulae (C), (D), (E), and (H): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is CH; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is 1 or 2.

In other embodiments of formulae (C), (D), (E), and (H): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is N; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

In other embodiments of formula (D): $P^5$ is selected from $C_1$-$C_6$alkyl, and —Y-L-X—P(O)(OR$^X$)(OR$^Y$).

In other embodiments of formula (D): X is O; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (D): X is a covalent bond; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): X is O; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): X is a covalent bond; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): $X^E$ is CH$_2$, $P^8$ is $C_1$-$C_6$alkoxy optionally substituted with —Y-L-X—P(O)(OR$^X$)(OR$^Y$).

In other embodiments of formula (E): $P^9$ is —NHC$_1$-C$_6$alkyl optionally substituted with OH and $C_1$-$C_6$alkyl, and —Y-L-X—P(O)(OR$^X$)(OR$^Y$).

In some embodiments, a compound of formula (C) is not a compound in which $P^4$ is —Y-L-X—P(O)(OR$^X$)(OR$^Y$).

In some embodiments, in a compound of formula (C), $P^4$ is selected from H, $C_1$-$C_6$alkyl, —$C_1$-$C_6$alkylaryl.

In some embodiments of formula (H): $X^{H1}$-$X^{H2}$ is $CR^{H2}R^{H3}$, $R^{H2}$ and $R^{H3}$ are H, $X^{H3}$ is N, X is a covalent bond; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In some embodiments of formula (H): $X^{H1}$-$X^{H2}$ is $CR^{H2}R^{H3}$, $R^{H2}$ and $R^{H3}$ are H, $X^{H3}$ is N, X is O; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

The 'parent' compounds of formula (G) are useful TLR8 agonists (see references 140 & 141) but are preferably modified herein by attachment of a phosphorus-containing moiety to permit adsorption. In some embodiments of formula (G), the compounds have structures according to formula (G');

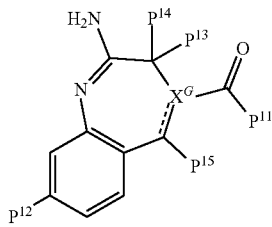

(G')

In some embodiments of formula (G) or (G'): $X^G$ is C and ---- represents a double bond.

In some embodiments of formula (G) or (G'): X is a covalent bond; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In some embodiments of formula (G) or (G'): X is O; L is selected from $C_1$-$C_6$alkylene and —((CH$_2$)$_p$O)$_q$(CH$_2$)$_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

Immunogenic Compositions

In addition to the antigen and adjuvant components discussed above, compositions of the invention may comprise further non-antigenic component(s). These can include carriers, excipients, buffers, etc. These non-antigenic components may have various sources. For example, they may be present in one of the antigen or adjuvant materials that is used during manufacture or may be added separately from those components.

Preferred compositions of the invention include one or more pharmaceutical carrier(s) and/or excipient(s).

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [178], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 6.0 and 7.5. A manufacturing process may therefore include a step of adjusting the pH of a composition prior to packaging. Aqueous compositions administered to a patient can have a pH of between 5.0 and 7.5, and more typically between 5.0 and 6.0 for optimum stability; where a diphtheria toxoid and/or tetanus toxoid is present, the pH is ideally between 6.0 and 7.0.

Compositions of the invention are preferably sterile.

Compositions of the invention are preferably non-pyrogenic e.g. containing <1 EU (endotoxin unit, a standard measure; 1 EU is equal to 0.2 ng FDA reference standard Endotoxin EC-2 'RSE') per dose, and preferably <0.1 EU per dose.

Compositions of the invention are preferably gluten free.

If a composition includes adsorbed component then it may be a suspension with a cloudy appearance. This appearance means that microbial contamination is not readily visible, and so the vaccine preferably contains an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal) during the process of the invention. Thus, between 1 and all of the components mixed in a process may be substantially free from mercurial preservative. However, the presence of trace amounts may be unavoidable if a component was treated with such a preservative before being used in the invention. For safety, however, it is preferred that the final composition contains less than about 25 ng/ml mercury. More preferably, the final vaccine product contains no detectable thimerosal. This will generally be achieved by removing the mercurial preservative from an antigen preparation prior to its addition in the process of the invention or by avoiding the use of thimerosal during the preparation of the components used to make the composition. Mercury-free compositions are preferred.

Compositions of the invention will usually be in aqueous form.

During manufacture, dilution of components to give desired final concentrations will usually be performed with WFI (water for injection), or with buffer.

The invention can provide bulk material which is suitable for packaging into individual doses, which can then be distributed for administration to patients. Concentrations discussed above are typically concentrations in final packaged dose, and so concentrations in bulk vaccine may be higher (e.g. to be reduced to final concentrations by dilution).

Compositions of the invention are administered to patients in unit doses i.e. the amount of a composition given to a single patient in a single administration (e.g. a single injection is a unit dose). Where a composition is administered as a liquid then a unit dose typically has a volume of 0.5 ml. This volume will be understood to include normal variance e.g. 0.5 ml±0.05 ml. For multidose situations, multiple dose amounts will be extracted and packaged together in a single container e.g. 5 ml for a 10-dose multidose container (or 5.5 ml with 10% overfill).

Residual material from individual antigenic components may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 µg/ml, preferably <5 µg/ml). Media or stabilizers may have been used during poliovirus preparation (e.g. Medium 199), and these may carry through to the final vaccine. Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 µg/ml, preferably <10 µg/ml, each. Other components from antigen preparations, such as neomycin (e.g. neomycin sulfate, particularly from a poliovirus component), polymyxin B (e.g. polymyxin B sulfate, particularly from a poliovirus component), etc. may also be present at sub-nanogram amounts per dose. A further possible component of the final vaccine which originates in the antigen preparations arises from less-than-total purification of antigens. Small amounts of *B. pertussis, C. diphtheriae, C. tetani* and *S. cerevisiae* proteins and/or genomic DNA may therefore be present. To minimize the amounts of these residual components, antigen preparations are preferably treated to remove them prior to the antigens being used with the invention.

Where a poliovirus component is used, it will generally have been grown on Vero cells. The final vaccine preferably contains less than 10 ng/ml, preferably ≤1 ng/ml e.g. ≤500 pg/ml or ≤50 pg/ml of Vero cell DNA e.g. less than 10 ng/ml of Vero cell DNA that is ≥50 base pairs long.

Compositions of the invention are presented for use in containers. Suitable containers include vials and disposable syringes (preferably sterile ones). Processes of the invention may comprise a step of packaging the vaccine into containers for use. Suitable containers include vials and disposable syringes (preferably sterile ones).

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Where a composition of the invention is presented in a vial, this is preferably made of a glass or plastic material. The vial is preferably sterilized before the composition is added to it. To avoid problems with latex-sensitive patients, vials may be sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

After a composition is packaged into a container, the container can then be enclosed within a box for distribution e.g. inside a cardboard box, and the box will be labeled with details of the vaccine e.g. its trade name, a list of the antigens in the vaccine (e.g. 'hepatitis B recombinant', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Adult Use Only' or 'For Pediatric Use Only'), an expiration date, an indication, a patent number, etc. Each box might contain more than one packaged vaccine e.g. five or ten packaged vaccines (particularly for vials).

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The packaged vaccine is preferably stored at between 2° C. and 8° C. It should not be frozen.

Vaccines can be provided in full-liquid form (i.e. where all antigenic components are in aqueous solution or suspension) after manufacture, or they can be prepared in a form where the vaccine can be prepared extemporaneously at the time/point of use by mixing together two components. Such two-component embodiments include liquid/liquid mixing and liquid/solid mixing e.g. by mixing aqueous material with lyophilised material. For instance, in one embodiment a vaccine can be made by mixing: (a) a first component comprising aqueous antigens and/or adjuvant; and (b) a second component comprising lyophilized antigens. In another embodiment a vaccine can be made by mixing: (a) a first component comprising aqueous antigens and/or adjuvant; and (b) a second component comprising aqueous antigens. In another embodiment a vaccine can be made by mixing: (a) a first component comprising aqueous antigens; and (b) a second component comprising aqueous adjuvant. The two components are preferably in separate containers (e.g. vials and/or syringes), and the invention provides a kit comprising components (a) and (b).

Another useful liquid/lyophilised format comprises (a) an aqueous complex of an aluminium salt and a TLR agonist and (b) a lyophilised component including one or more antigens. A vaccine composition suitable for patient administration is obtained by mixing components (a) and (b). In some embodiments component (a) is antigen-free, such that all antigenic components in the final vaccine are derived from component (b); in other embodiments component (a) includes one or more antigen(s), such that the antigenic components in the final vaccine are derived from both components (a) and (b).

Thus the invention provides a kit for preparing a combination vaccine, comprising components (a) and (b) as noted above. The kit components are typically vials or syringes, and a single kit may contain both a vial and a syringe. The invention also provides a process for preparing such a kit, comprising the following steps: (i) preparing an aqueous component vaccine as described above; (ii) packaging said aqueous combination vaccine in a first container e.g. a syringe; (iii) preparing an antigen-containing component in lyophilised form; (iv) packaging said lyophilised antigen in a second container e.g. a vial; and (v) packaging the first container and second container together in a kit. The kit can then be distributed to physicians.

A liquid/lyophilised format is particularly useful for vaccines that include a conjugate component, particularly Hib and/or meningococcal and/or pneumococcal conjugates, as these may be more stable in lyophilized form. Thus conjugates may be lyophilised prior to their use with the invention.

Where a component is lyophilised it generally includes non-active components which were added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. A final vaccine obtained by aqueous reconstitution of the lyophilised material may thus contain lactose and/or sucrose. It is preferred to use amorphous excipients and/or amorphous buffers when preparing lyophilised vaccines [179].

Most compositions of the invention include diphtheria, tetanus and pertussis toxoids. In pediatric-type compositions the composition includes an excess of diphtheria toxoid relative to tetanus toxoid (as measured in Lf units). The excess is ideally at least 1.5:1 e.g. 5 Lf of diphtheria toxoid for every 2 Lf of tetanus toxoid (i.e. a 2.5:1 ratio). These embodiments are most useful in infants and children. In booster-type compositions, which are most useful in adolescents and adults, the composition includes an excess of tetanus toxoid relative to diphtheria toxoid (as measured in Lf units). The excess is ideally at least 1.5:1 e.g. 2 Lf of tetanus toxoid for every 1 Lf of diphtheria toxoid (i.e. a 2:1 ratio). In further embodiments, equal amounts of diphtheria and tetanus toxoids are used (in Lf units). Where one of diphtheria or tetanus is present at an excess, the excess should ideally be at least 1.5-fold e.g. 2-fold or 2.5-fold, but the excess will not usually be more than 5-fold.

A composition of the invention includes a serogroup B meningococcus immunogen and at least one of a diphtheria toxoid, a tetanus toxoid, and/or a pertussis toxoid. Ideally a composition includes all four of a serogroup B meningococcus immunogen, a diphtheria toxoid, a tetanus toxoid, and a pertussis toxoid. In some embodiments a composition of the invention includes no immunogens beyond those in this list; in other embodiments a composition of the invention does include immunogens beyond those in this list. Thus, for example, some compositions include diphtheria, tetanus and pertussis toxoids, inactivated poliovirus for Types 1, 2 & 3, hepatitis B virus surface antigen and a Hib conjugate. The antigenic portion of these compositions may consist of the antigens in this list, or may further include antigens from additional pathogens (e.g. meningococcus). Thus the compositions can be used as vaccines themselves, or as components of further combination vaccines.

Specific embodiments of the invention include compositions whose immunogens consist of: (a) D-T-aP-MenB; (b) D-T-aP-MenB-IPV; (c) D-T-aP-MenB-HBsAg; (d) D-T-aP-MenB-Hib; (e) D-T-aP-MenB-HBsAg-Hib; (f) D-T-aP-MenB-HBsAg-IPV; (g) D-T-aP-MenB-IPV-Hib; (h) D-T-aP-MenB-IPV-Hib-HBsAg; (i) D-T-MenB; where "D" is diphtheria toxoid, "T" is tetanus toxoid, "aP" is an acellular pertussis antigen or mixture, MenB is a serogroup B meningococcus antigen or mixture, "IPV" is an inactivated poliovirus antigen or mixture, "HBsAg" is a hepatitis B virus surface antigen, and "Hib" is a conjugated *H. influenzae* type B capsular saccharide.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a composition of the invention for use in medicine. The composition may be administered as variously described herein e.g. in some embodiments by giving an infant no more than two doses of a combination vaccine.

The invention also provides the use of a serogroup B meningococcus immunogen, a diphtheria toxoid, a tetanus toxoid, and a pertussis toxoid (and, optionally, an adjuvant) in the manufacture of a medicament for raising an immune response in a patient. The medicament is ideally a composition as variously described elsewhere herein, and it can be administered as variously described herein.

The immune responses raised by these methods, uses and compositions are ideally protective, and immunogenic compositions of the invention are preferably vaccines, for use in the prevention of at least diphtheria, tetanus, and whooping cough. Depending on their antigen components the vaccines may also protect against bacterial meningitis, polio, hepatitis, etc.

In order to have full efficacy, a typical primary immunization schedule (particularly for a child) may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; at 2, 3 & 4 months; or at 0, 1, 2, 6 & 12 months.

Compositions can also be used as booster doses e.g. for children in the second year of life, for an adolescent, or for an adult.

Compositions of the invention can be administered by intramuscular injection e.g. into the arm or leg.

Optional Requirements and Disclaimers [180]

In some embodiments, the invention does not encompass compositions in unit dose form comprising (i) a diphtheria toxoid, a tetanus toxoid, and a pertussis toxoid, and (ii) an aluminium salt adjuvant, wherein the amount of $Al^{+++}$ in the unit dose is less than 0.2 mg. In other embodiments, if a composition is in unit dose form and comprises (i) a diphtheria toxoid, a tetanus toxoid, and a pertussis toxoid, and (ii) an aluminium salt adjuvant, but the amount of $Al^{+++}$ in the unit dose is less than 0.2 mg, then: (a) the composition includes at least a 1.5-fold excess of diphtheria toxoid to tetanus toxoid, measured in Lf units; or (b) the composition includes at least a 1.5-fold excess of tetanus toxoid to diphtheria toxoid, measured in Lf units; or (c) the composition includes an acellular PT-containing antigen pertussis antigen rather than a whole-cell pertussis antigen.

In some embodiments, the invention does not encompass compositions comprising (i) a diphtheria toxoid, a tetanus toxoid, and a pertussis toxoid, and (ii) an aluminium salt adjuvant, wherein the concentration of $Al^{+++}$ is less than 0.4 mg/ml. In other embodiments, if a composition comprises (i) a diphtheria toxoid, a tetanus toxoid, and a pertussis toxoid, and (ii) an aluminium salt adjuvant, but the concentration of $Al^{+++}$ in the unit dose is less than 0.4 mg/ml, then: (a) the composition includes at least a 1.5-fold excess of diphtheria toxoid to tetanus toxoid, measured in Lf units; or (b) the composition includes at least a 1.5-fold excess of tetanus toxoid to diphtheria toxoid, measured in Lf units; or (c) the composition includes an acellular PT-containing antigen pertussis antigen rather than a whole-cell pertussis antigen.

In some embodiments, the invention does not encompass compositions comprising (i) an aluminium salt adjuvant and (ii) ≤8 Lf/ml diphtheria toxoid, ≤3.5 Lf/ml tetanus toxoid, and ≤5 µg/ml pertussis toxoid. In other embodiments, if a composition comprises (i) an aluminium salt adjuvant and (ii) ≤8 Lf/ml diphtheria toxoid, ≤3.5 Lf/ml tetanus toxoid, and ≤5 µg/ml pertussis toxoid, then: (a) the composition includes at least a 1.5-fold excess of diphtheria toxoid to tetanus toxoid, measured in Lf units; or (b) the composition includes at least a 1.5-fold excess of tetanus toxoid to diphtheria toxoid, measured in Lf units; or (c) the composition includes an acellular PT-containing antigen pertussis antigen rather than a whole-cell pertussis antigen.

In some embodiments, the invention does not encompass compositions comprising (i) an oil-in-water emulsion adjuvant (ii) a diphtheria toxoid, a tetanus toxoid, a pertussis toxoid, and a Hib conjugate, and (iii) a hepatitis B virus surface antigen and/or an inactivated poliovirus antigen. In other embodiments, if a composition comprises (i) an oil-in-water emulsion adjuvant (ii) a diphtheria toxoid, a tetanus toxoid, a pertussis toxoid, and a Hib conjugate, then: (a) the composition does not include a hepatitis B virus surface antigen; or (b) the composition does not include an inactivated poliovirus antigen; or (c) the composition includes neither an inactivated poliovirus antigen nor a hepatitis B virus surface antigen; or (d) the composition includes at least a 1.5-fold excess of diphtheria toxoid to tetanus toxoid, measured in Lf units; or (e) the composition includes at least a 1.5-fold excess of tetanus toxoid to diphtheria toxoid, measured in Lf units; or (f) the composition includes an acellular PT-containing antigen pertussis antigen rather than a whole-cell pertussis antigen.

In some embodiments, the invention does not encompass compositions which comprise a conjugate of a *H. influenzae* type b capsular saccharide antigen and an outer membrane protein complex from serogroup B meningococcus. In other embodiments, if a composition of the invention includes a conjugate of a *H. influenzae* type b capsular saccharide antigen and an outer membrane protein complex from serogroup B meningococcus then it must also include a further immunogen from serogroup B meningococcus.

In some embodiments, the invention does not encompass compositions which include both an aluminium salt adjuvant and a TLR4 agonist.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg can be used.

Amounts of conjugates are generally given in terms of mass of saccharide (i.e. the dose of the conjugate (carrier+ saccharide) as a whole is higher than the stated dose) in order to avoid variation due to choice of carrier.

Phosphorous-containing groups employed with the invention may exist in a number of protonated and deprotonated forms depending on the pH of the surrounding environment, for example the pH of the solvent in which they are dissolved. Therefore, although a particular form may be illustrated herein, it is intended, unless otherwise mentioned, for these illustrations to merely be representative and not limiting to a specific protonated or deprotonated form. For example, in the case of a phosphate group, this has been illustrated as —OP(O)(OH)$_2$ but the definition includes the protonated forms —[OP(O)(OH$_2$)(OH)]$^+$ and —[OP(O)(OH$_2$)$_2$]$^{2+}$ that may exist in acidic conditions and the deprotonated forms —[OP(O)(OH)(O)]$^-$ and [OP(O)(O)$_2$]$^{2-}$ that may exist in basic conditions. The invention encompasses all such forms.

TLR agonists can exist as pharmaceutically acceptable salts. Thus, the compounds may be used in the form of their pharmaceutically acceptable salts i.e. physiologically or toxicologically tolerable salt (which includes, when appropriate, pharmaceutically acceptable base addition salts and pharmaceutically acceptable acid addition salts).

In the case of TLR agonists shown herein which may exist in tautomeric forms, the compound can be used in all such tautomeric forms.

Where a compound is administered to the body as part of a composition then that compound may alternatively be replaced by a suitable prodrug.

Where animal (and particularly bovine) materials are used in the culture of cells, they should be obtained from sources that are free from transmissible spongiform encephalopathies (TSEs), and in particular free from bovine spongiform encephalopathy (BSE).

Meningococcal Protein Immunogens

NHBA (Neisserial Heparin Binding Antigen)

NHBA [181] was included in the published genome sequence for meningococcal serogroup B strain MC58 [26] as gene NMB2132 (GenBank accession number GI:7227388; SEQ ID NO: 9 herein). Sequences of NHBA from many strains have been published since then. For example, allelic forms of NHBA (referred to as protein '287') can be seen in FIGS. 5 and 15 of reference 182, and in example 13 and FIG. 21 of reference 183 (SEQ IDs 3179 to 3184 therein). Various immunogenic fragments of NHBA have also been reported.

Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 9.

The most useful NHBA antigens can elicit antibodies which, after administration to a subject, can bind to a meningococcal polypeptide consisting of amino acid sequence SEQ ID NO: 9. Advantageous NHBA antigens for use with the invention can elicit bactericidal anti-meningococcal antibodies after administration to a subject.

One useful NHBA antigen comprises SEQ ID NO: 4, which is a fusion of NHBA to NMB1030, as present in the BEXSERO™ product.

NadA (Neisserial Adhesin A)

The NadA antigen was included in the published genome sequence for meningococcal serogroup B strain MC58 [26] as gene NMB1994 (GenBank accession number GI:7227256; SEQ ID NO: 10 herein). The sequences of NadA antigen from many strains have been published since then, and the protein's activity as a Neisserial adhesin has been well documented. Various immunogenic fragments of NadA have also been reported.

Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10.

NadA will usually be present in a composition in oligomeric form e.g. trimers [184].

The most useful NadA antigens can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. SEQ ID NO: 6 is one such fragment, as present in the BEXSERO™ product.

fHbp (Factor H Binding Protein)

The fHbp antigen has been characterised in detail. It has also been known as protein '741' [SEQ IDs 2535 & 2536 in ref 183], 'NMB1870', 'GNA1870' [185, 186, 207], 'P2086', 'LP2086' or 'ORF2086' [187-189]. It is naturally a lipoprotein and is expressed across all meningococcal serogroups. The structure of fHbp's C-terminal immunodominant domain ('fHbpC') has been determined by NMR [190]. This part of the protein forms an eight-stranded β-barrel, whose strands are connected by loops of variable lengths. The barrel is preceded by a short α-helix and by a flexible N-terminal tail.

The fHbp antigen falls into three distinct variants [191] and it has been found that serum raised against a given family is bactericidal within the same family, but is not active against strains which express one of the other two families i.e. there is intra-family cross-protection, but not inter-family cross-protection. The invention can use a single fHbp variant, but is will usefully include a fHbp from two or three of the variants.

Where a composition comprises a single fHBP variant, it may include one of the following:

(a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;

(b) a second polypeptide, comprising a second amino acid sequence, where the second amino acid sequence comprises an amino acid sequence (i) having at least b % sequence identity to SEQ ID NO: 2 and/or (ii) consisting of a fragment of at least y contiguous amino acids from SEQ ID NO: 2;

(c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

The value of a is at least 80 e.g. 82, 84, 86, 88, 90, 92, 94, 95, 96, 97, 98, 99 or more. The value of b is at least 80 e.g. 82, 84, 86, 88, 90, 92, 94, 95, 96, 97, 98, 99 or more. The value of c is at least 80 e.g. 82, 84, 86, 88, 90, 92, 94, 95, 96, 97, 98, 99 or more. The values of a, b and c may be the same or different. In some embodiments, a b and c are identical.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z may be the same or different. In some embodiments, x y and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof.

In some embodiments the fragment of at least x contiguous amino acids from SEQ ID NO: 1 is not also present within SEQ ID NO: 2 or within SEQ ID NO: 3. Similarly, the fragment of at least y contiguous amino acids from SEQ ID NO: 2 might not also be present within SEQ ID NO: 1 or within SEQ ID NO: 3. Similarly, the fragment of at least z contiguous amino acids from SEQ ID NO: 3 might not also be present within SEQ ID NO: 1 or within SEQ ID NO: 2. In some embodiments, when said fragment from one of SEQ ID NOs: 1 to 3 is aligned as a contiguous sequence against the other two SEQ ID NOs, the identity between the fragment and each of the other two SEQ ID NOs is less than 75% e.g. less than 70%, less than 65%, less than 60%, etc.

Where a composition comprises two different meningococcal fHBP antigens, it may include a combination of: (i) a first and second polypeptide as defined above; (ii) a first and third polypeptide as defined above; or (iii) a second and third polypeptide as defined above. A combination of a first and third polypeptide is preferred. Where a composition comprises two different meningococcal fHBP antigens, although these may share some sequences in common, the first, second and third polypeptides have different fHBP amino acid sequences.

A polypeptide comprising the first amino acid sequence will, when administered to a subject, elicit an antibody response comprising antibodies that bind to the wild-type meningococcus protein which has nascent amino acid sequence SEQ ID NO: 20 (MC58). In some embodiments some or all of these antibodies do not bind to the wild-type meningococcus protein which has nascent amino acid sequence SEQ ID NO: 21 or to the wild-type meningococcus protein which has nascent amino acid sequence SEQ ID NO: 22.

A polypeptide comprising the second amino acid sequence will, when administered to a subject, elicit an antibody response comprising antibodies that bind to the wild-type meningococcus protein which has nascent amino acid sequence SEQ ID NO: 21 (2996). In some embodiments some or all of these antibodies do not bind to the wild-type meningococcus protein which has nascent amino acid sequence SEQ ID NO: 20 or to the wild-type meningococcus protein which has nascent amino acid sequence SEQ ID NO: 22.

A polypeptide comprising the third amino acid sequence will, when administered to a subject, elicit an antibody response comprising antibodies that bind to the wild-type meningococcus protein which has nascent amino acid sequence SEQ ID NO: 22 (M1239). In some embodiments some or all of these antibodies do not bind to the wild-type meningococcus protein which has nascent amino acid sequence SEQ ID NO: 20 or to the wild-type meningococcus protein which has nascent amino acid sequence SEQ ID NO: 21.

A useful first amino acid sequence has at least 85% identity (e.g. >95% or 100%) to SEQ ID NO: 1 (strain MC58). Another useful first amino acid sequence has at least 95% identity (e.g. >98% or 100%) to SEQ ID NO: 23 (strain CDC1573).

A useful third amino acid sequence has at least 85% identity (e.g. >95% or 100%) to SEQ ID NO: 3 (strain M1239). Another useful third amino acid sequence has at least 95% identity (e.g. >98% or 100%) to SEQ ID NO: 25 (strain M98-250771).

Combinations comprising a mixture of first and third sequences based around SEQ ID NOs: 23 and 25 (or their close variants) are particularly useful. Thus a composition may comprise a polypeptide comprising amino acid sequence SEQ ID NO: 24 and a polypeptide comprising amino acid sequence SEQ ID NO: 26.

Where a composition includes two meningococcal fHBP antigens, this may be in a bivalent fHBP composition, or there may be more than two different fHBP antigens e.g. in a trivalent or tetravalent fHBP composition.

Another useful fHbp which can be used according to the invention is one of the modified forms disclosed, for example, in reference 192 e.g. comprising SEQ ID NO: 20 or 23 therefrom. These modified forms can elicit antibody responses which are broadly bactericidal against meningococci by recognising multiple fHbp variant. One such modified form is SEQ ID NO: 28 herein (SEQ ID NO: 23 in ref 192), which can be fused to non-fHbp sequences as disclosed in reference 193 e.g. to give SEQ ID NO: 19 (which contains NMB2091 and two copies of SEQ ID NO: 28), which is used in the examples below.

SEQ ID NO: 77 from ref 192 is another useful fHbp sequence which can be used in order to provide broad inter-strain reactivity.

In some embodiments fHBP polypeptide(s) are lipidated e.g. at a N-terminus cysteine. In other embodiments, however, fHBP polypeptide(s) are not lipidated. For lipidated fHBPs, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-glyceryl cysteine), etc. Examples of mature lipidated fHBP sequences are SEQ ID NO: 24 (including SEQ ID NO: 23) and SEQ ID NO: 26 (including SEQ ID NO: 25). If fHbp protein(s) are located in a vesicle then they will usually be lipidated.

Administration of a fHBP will preferably elicit antibodies which can bind to a meningococcal polypeptide consisting of amino acid sequence SEQ ID NO: 1, 2 or 3. Advantageous fHBP antigens for use with the invention can elicit bactericidal anti-meningococcal antibodies after administration to a subject.

The total amount of a fHBP polypeptide will usually be between 1 and 500 µg per unit dose e.g. between 60 and 200 µg per unit. An amount of 10, 20, 40, 50, 60, 80, 100 or 200 µg per unit dose for each fHBP polypeptide is typical in a human vaccine dose.

Where a composition comprises different meningococcal fHBP antigens, these may be present as separate polypeptides as described above (e.g. a first and second polypeptide) or they may be present as part of a single fusion polypeptide i.e. where at least two (e.g. 2, 3, 4, 5, or more) fHBP antigens are expressed as a single polypeptide chain, as disclosed for meningococcal antigens in reference 194. Most usefully, a fusion polypeptide can include each of a first, second and third sequence as discussed above e.g. SEQ ID NO: 27.

HmbR

The full-length HmbR sequence was included in the published genome sequence for meningococcal serogroup B strain MC58 [26] as gene NMB1668 (SEQ ID NO: 7 herein). Reference 195 reports a HmbR sequence from a different strain (SEQ ID NO: 8 herein), and reference 196 reports a further sequence (SEQ ID NO: 15 herein). SEQ ID NOs: 7 and 8 differ in length by 1 amino acid and have 94.2% identity. SEQ ID NO: 15 is one amino acid shorter than SEQ ID NO: 7 and they have 99% identity (one insertion, seven differences). The invention can use any such HmbR polypeptide.

The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7.

Preferred fragments of j amino acids comprise an epitope from SEQ ID NO: 7. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 197. Fragments that retain a transmembrane sequence are useful, because they can be displayed on the bacterial surface e.g. in vesicles. If soluble HmbR is used, however, sequences omitting the transmembrane sequence, but typically retaining epitope(s) from the extracellular portion, can be used.

The most useful HmbR antigens can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

NspA (Neisserial Surface Protein A)

The NspA antigen was included in the published genome sequence for meningococcal serogroup B strain MC58 [26] as gene NMB0663 (GenBank accession number GI:7225888; SEQ ID NO: 11 herein). The antigen was previously known from references 198 & 199. The sequences of NspA antigen from many strains have been published since then. Various immunogenic fragments of NspA have also been reported.

Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11.

The most useful NspA antigens can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

NhhA (Neisseria Hia Homologue)

The NhhA antigen was included in the published genome sequence for meningococcal serogroup B strain MC58 [26] as gene NMB0992 (GenBank accession number GI:7226232; SEQ ID NO: 12 herein). The sequences of NhhA antigen from many strains have been published since e.g. refs 182 & 200, and various immunogenic fragments of NhhA have been reported. It is also known as Hsf.

Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12.

The most useful NhhA antigens can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

App (Adhesion and Penetration Protein)

The App antigen was included in the published genome sequence for meningococcal serogroup B strain MC58 [26] as gene NMB1985 (GenBank accession number GI:7227246; SEQ ID NO: 13 herein). The sequences of App antigen from many strains have been published since then. It has also been known as 'ORF1' and 'Hap'. Various immunogenic fragments of App have also been reported.

Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13.

The most useful App antigens can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

Omp85 (85 kDa Outer Membrane Protein)

The Omp85 antigen was included in the published genome sequence for meningococcal serogroup B strain MC58 [26] as gene NMB0182 (GenBank accession number GI:7225401; SEQ ID NO: 14 herein). The sequences of Omp85 antigen from many strains have been published since then. Further information on Omp85 can be found in references 201 and 202. Various immunogenic fragments of Omp85 have also been reported.

Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14.

The most useful Omp85 antigens can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

TbpA

The TbpA antigen was included in the published genome sequence for meningococcal serogroup B strain MC58 [26] as gene NMB0461 (GenBank accession number GI:7225687; SEQ ID NO: 23 herein). The sequences of TbpA from many strains have been published since then. Various immunogenic fragments of TbpA have also been reported.

Preferred TbpA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 23.

The most useful TbpA antigens can elicit antibodies which, after administration to a subject, can bind to a meningococcal polypeptide consisting of amino acid sequence SEQ ID NO: 23. Advantageous TbpA antigens for use with the invention can elicit bactericidal anti-meningococcal antibodies after administration to a subject.

TbpB

The TbpB antigen was included in the published genome sequence for meningococcal serogroup B strain MC58 [26] as gene NMB0460 (GenBank accession number GI:7225686; SEQ ID NO: 24 herein). The sequences of TbpB from many strains have been published since then. Various immunogenic fragments of TbpB have also been reported.

Preferred TbpB antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 24.

The most useful TbpB antigens can elicit antibodies which, after administration to a subject, can bind to a meningococcal polypeptide consisting of amino acid sequence SEQ ID NO: 24. Advantageous TbpB antigens for use with the invention can elicit bactericidal anti-meningococcal antibodies after administration to a subject.

Cu,Zn-Superoxide Dismutase

The Cu,Zn-superoxide dismutase antigen was included in the published genome sequence for meningococcal serogroup B strain MC58 [26] as gene NMB1398 (GenBank accession number GI:7226637; SEQ ID NO: 25 herein). The sequences of Cu,Zn-superoxide dismutase from many strains have been published since then. Various immunogenic fragments of Cu,Zn-superoxide dismutase have also been reported.

Preferred Cu,Zn-superoxide dismutase antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 25.

The most useful Cu,Zn-superoxide dismutase antigens can elicit antibodies which, after administration to a subject, can bind to a meningococcal polypeptide consisting of amino acid sequence SEQ ID NO: 25. Advantageous Cu,Zn-superoxide dismutase antigens for use with the invention can elicit bactericidal anti-meningococcal antibodies after administration to a subject.

ZnuD

The ZnuD antigen was included in the published genome sequence for meningococcal serogroup B strain MC58 [26] as gene NMB0964 (GenBank accession number GI:15676857; SEQ ID NO: 29 herein). The sequences of ZnuD from many strains have been published since then e.g. see references 203 & 204.

Preferred ZnuD antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 29; and/or (b) comprising a fragment of at least 'n' consecutive amino acids of SEQ ID NO: 29, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 29.

The most useful ZnuD antigens can elicit antibodies which, after administration to a subject, can bind to a meningococcal polypeptide consisting of amino acid sequence SEQ ID NO: 29. Advantageous ZnuD antigens for use with the invention can elicit bactericidal anti-meningococcal antibodies after administration to a subject.

Meningococcal Vesicles

The invention can be used with various types of vesicle which are known for *Neisseria meningitidis*.

Reference 22 discloses the construction of vesicles from meningococcal strains modified to express six different PorA subtypes. References 205-207 report pre-clinical studies of an OMV vaccine in which fHbp (also known as GN1870) is over-expressed (and this over-expression can be combined with knockout of LpxL1 [208]). Reference 209 recently reported a clinical study of five formulations of an OMV vaccine in which PorA & FrpB are knocked-out and Hsf & TbpA are over-expressed. Reference 210 reports a native outer membrane vesicle vaccine prepared from bacteria having inactivated synX, lpxL1, and lgtA genes. All such vesicles can be used herein.

OMVs can be prepared from meningococci which over-express desired antigen(s) due to genetic modification. In addition to genetic modification(s) which cause over-expression of antigen(s) of interest, the bacteria may include one or more further modifications. For instance, the bacterium may have a knockout of one or more of lpxL1, lgtB, porA, frpB, synX, lgtA, mltA and/or lst.

The bacterium may have low endotoxin levels, achieved by knockout of enzymes involved in LPS biosynthesis [211,212].

The bacterium may be of any serotype (e.g. 1, 2a, 2b, 4, 14, 15, 16, etc.), any serosubtype, and any immunotype (e.g. L1; L2; L3; L3,3,7; L10; etc.). Vesicles can usefully be prepared from strains having one of the following subtypes: P1.2; P1.2,5; P1.4; P1.5; P1.5,2; P1.5,c; P1.5 c,10; P1.7,16; P1.7,16b; P1.7h,4; P1.9; P1.15; P1.9,15; P1.12,13; P1.13; P1.14; P1.21,16; P1.22,14.

The bacterium may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref 213] e.g. the ET-37 complex is the ST-11 complex by MLST, the ET-5 complex is ST-32 (ET-5), lineage 3 is ST-41/44, etc.

In some embodiments a bacterium may include one or more of the knockout and/or hyper-expression mutations disclosed in references 226 and 214-216. Suitable genes for modification include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [214]; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; and (d) CtrA, CtrB, CtrD, FrpB, OpA, OpC, PilC, PorB, SiaD, SynA, SynB, and/or SynC.

A bacterium may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xi) deleted cps gene complex; (xi) up-regulated NHBA; (xii) up-regulated NadA; (xiii) up-regulated NHBA and NadA; (xiv) up-regulated fHbp; (xv) down-regulated LpxL1. A truncated LOS can be one that does not include a sialyl-lacto-N-neotetraose epitope e.g. it might be a galactose-deficient LOS. The LOS may have no α chain.

If lipo-oligosaccharide (LOS) is present in a vesicle it is possible to treat the vesicle so as to link its LOS and protein components ("intra-bleb" conjugation [216]).

The vesicles may lack LOS altogether, or they may lack hexa-acylated LOS e.g. LOS in the vesicles may have a reduced number of secondary acyl chains per LOS molecule [217]. For example, the vesicles may from a strain which has a lpxL1 deletion or mutation which results in production of a penta-acylated LOS [206,210]. LOS in a strain may lack a lacto-N-neotetraose epitope e.g. it may be a lst and/or lgtB knockout strain [209]. LOS may lack at least one wild-type primary O-linked fatty acid [218]. LOS having. The LOS may have no α chain. The LOS may comprise GlcNAc-Hep$_2$phosphoethanolamine-KDO$_2$-Lipid A [219].

As a result of up-regulation mentioned above, vesicles prepared from modified meningococci contain higher levels of the up-regulated antigen(s). The increase in expression in the vesicles (measured relative to a corresponding wild-type strain) is usefully at least 10%, measured in mass of the relevant antigen per unit mass of vesicle, and is more usefully at least 20%, 30%, 40%, 50%, 75%, 100% or more.

Suitable recombinant modifications which can be used to cause up-regulation of an antigen include, but are not limited to: (i) promoter replacement; (ii) gene addition; (iii) gene replacement; or (iv) repressor knockout. In promoter replacement, the promoter which controls expression of the antigen's gene in a bacterium is replaced with a promoter which provides higher levels of expression. For instance, the gene might be placed under the control of a promoter from a housekeeping metabolic gene. In other embodiments, the antigen's gene is placed under the control of a constitutive or inducible promoter. Similarly, the gene can be modified to ensure that its expression is not subject to phase variation. Methods for reducing or eliminating phase variability of gene expression in meningococcus are disclosed in reference 220. These methods include promoter replacement, or the removal or replacement of a DNA motif which is responsible for a gene's phase variability. In gene addition, a bacterium which already expresses the antigen receives a second copy of the relevant gene. This second copy can be integrated into the bacterial chromosome or can be on an episomal element such as a plasmid. The second copy can have a stronger promoter than the existing copy. The gene can be placed under the control of a constitutive or inducible promoter. The effect of the gene addition is to increase the amount of expressed antigen. In gene replacement, gene addition occurs but is accompanied by deletion of the existing copy of the gene. For instance, this approach was used in reference 207, where a bacterium's endogenous chromosomal fHbp gene was deleted and replaced by a plasmid-encoded copy (see also reference 221). Expression from the replacement copy is higher than from the previous copy, thus leading to up-regulation. In repressor knockout, a protein which represses expression of an antigen of interest is knocked out. Thus the repression does not occur and the antigen of interest can be expressed at a higher level. Promoters for up-regulated genes can advantageously include a CREN [222].

A modified strain will generally be isogenic with its parent strain, except for a genetic modification. As a result of the modification, expression of the antigen of interest in the modified strain is higher (under the same conditions) than in the parent strain. A typical modification will be to place a gene under the control of a promoter with which it is not found in nature and/or to knockout a gene which encodes a repressor.

In embodiments where NHBA is up-regulated, various approaches can be used. For convenience, the approach already reported in reference 181 can be used i.e. introduction of a NHBA gene under the control of an IPTG-inducible promoter. By this approach the level of expression of NHBA can be proportional to the concentration of IPTG added to a culture. The promoter may include a CREN.

In embodiments where NadA is up-regulated, various approaches can be used. One useful approach involves deletion of the gene encoding NadR (NMB1843), which is a transcriptional repressor protein [223] which down-regulates or represses the NadA-encoding gene in all strains tested. Knockout of NadR results in high-level constitutive expression of NadA. An alternative approach to achieve NadA up-regulation is to add 4-hydroxyphenylacetic to the culture medium. A further approach is to introduce a NadA gene under the control of an IPTG-inducible promoter.

Up-regulation of NhhA is already reported in references 209 and 224. Up-regulation of TbpA is already reported in references 209, 224 and 225. Up-regulation of HmbR is already reported in reference 196. Up-regulation of TbpB is already reported in reference 225. Up-regulation of NspA is already reported in reference 226, in combination with porA and cps knockout. Up-regulation of Cu,Zn-superoxide dismutase is already reported in reference 225. Up-regulation of fHbp is already reported in references 205-207 & 221, and by a different approach (expressing a constitutively-active mutant FNR) in references 227 & 228.

In some embodiments each of NHBA, NadA and fHbp are up-regulated. These three antigens are components of the "universal vaccine" disclosed in reference 8 or "4CMenB" [229,230]. In one embodiment, expression of NHBA is controlled by a strong promoter, NadR is knocked out, and the strain expresses a constitutively active mutant FNR. In another embodiment, expression of NHBA is controlled by a strong promoter, expression of fHbp is controlled by a strong promoter, and NadR is knocked out. The bacterium can also be a bacterium which does not express an active MltA (GNA33), such that it spontaneously releases vesicles which contain NHBA, NadA and fHbp. Ideally, the bacterium does not express a native LPS e.g. it has a mutant or knockout of LpxL1.

The vesicles may include one, more than one, or (preferably) zero PorA serosubtypes. Modification of meningococcus to provide multi-PorA OMVs is known e.g. from references 22 and 23. Conversely, modification to remove PorA is also known e.g. from reference 209.

The vesicles may be free from one of both of PorA and FrpB. Preferred vesicles are PorA-free.

The invention may be used with mixtures of vesicles from different strains. For instance, reference 24 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. Reference 25 also discloses useful combinations of different vesicles. A combination of vesicles from strains in each of the L2 and L3 immunotypes may be used in some embodiments.

Another useful combination of vesicles is disclosed in references 231 & 232. A trivalent mixture of this type can include vesicles prepared from each of: (a) a first strain which over-expresses NadA; (b) a second strain which over-expresses a fHbp sequence from variant 1 i.e. a first fHbp polypeptide sequence as defined above; and (c) a third strain which over-expresses a fHbp sequence from variant 2 i.e. a second fHbp polypeptide sequence as defined above. These strains can also have other modifications e.g. knockout of synX and LpxL1, as disclosed in ref 231.

MODES FOR CARRYING OUT THE INVENTION

An immunogen combination was prepared, containing the following components:

| | Immunogen | Amount (per 0.5ml) |
|---|---|---|
| T | Tetanus toxoid | 5 Lf |
| D | Diphtheria toxoid | 2 Lf |
| aP | Pertussis toxoid, PT-9 K/129 G | 4 µg |
| | FHA | 4 µg |
| | Pertactin | 8 µg |
| MenB | NHBA (SEQ ID NO: 4) | 50 µg |
| | NadA (SEQ ID NO: 6) | 50 µg |
| | fHbp (SEQ ID NO: 19) | 50 µg |

For comparison purposes, an equivalent combination was prepared but without the MenB proteins. These two immunogen combinations are referred to as "TdaP-MenB" and "TdaP".

These two combinations were adjuvanted with:
(a) aluminium hydroxide, 1 mg/dose ("Al—H")
(b) aluminium hydroxide, 1 mg/dose, with 100 µg adsorbed 'K2' TLR7 agonist
(c) aluminium hydroxide, 1 mg/dose, with 100 µg adsorbed synthetic MPL TLR4 agonist
(d) MF59 squalene-containing oil-in-water emulsion.

All antigens were adsorbed to the Al—H in compositions (a) to (c) for both TdaP and TdaP-MenB, although pertactin was not fully adsorbed in compositions which include the MenB immunogens.

In addition to these four pairs of adjuvanted compositions, a further pair was unadjuvanted. This gave 10 compositions in total, (C1) to (C10):

| | No adjuvant | Al-H | Al-H/K2 | Al-H/MPL | MF59 |
|---|---|---|---|---|---|
| TdaP | C1 | C2 | C3 | C4 | C5 |
| TdaP-MenB | C6 | C7 | C8 | C9 | C10 |

Furthermore, for comparison the BOOSTRIX™ product was also tested ("C11"), which contains (per 0.5 ml) 2.5Lf of diphtheria toxoid, 5Lf tetanus toxoid, and 18.5 µg acellular pertussis antigens (a mixture of purified PT, FHA and p69 pertactin), adjuvanted with a mixture of aluminium phosphate and hydroxide salts. Finally, an immunogen-free negative control of buffer alone was also prepared ("C12").

Figure 1A:
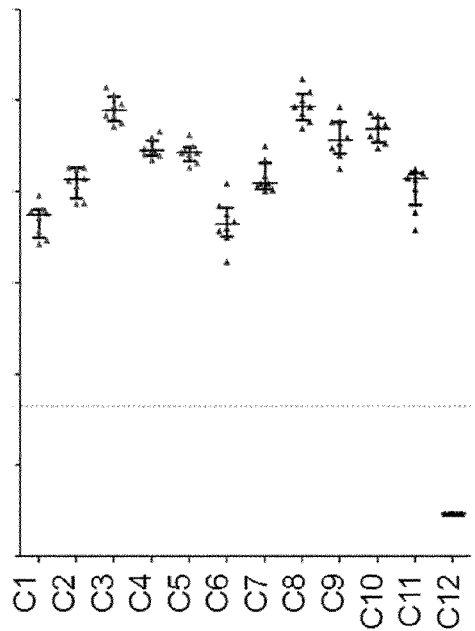
FIGS. 1 to 8 show serum total IgG responses against: (1) tetanus toxoid; (2) diphtheria toxoid; (3) pertussis toxoid; (4) pertactin; (5) FHA; (6) NadA; (7) NHBA; and (8) fHbp. Where a Figure includes panels (A) and (B), the data in (A) are at day 35 whereas the data in (B) are at day 49. The y-axis scale in all cases is 0.01 to 10,000.
Figure 1B:
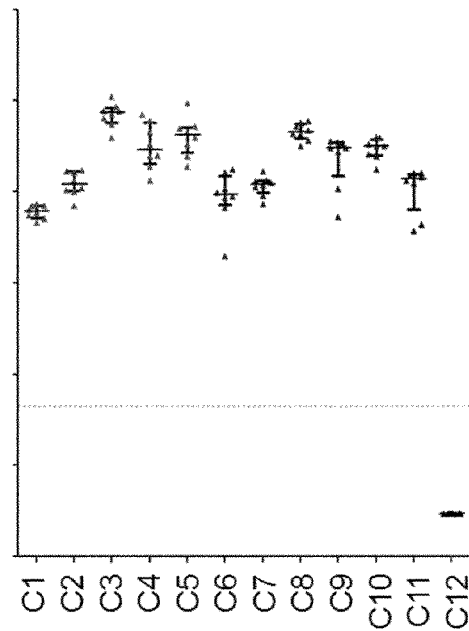
Figure 2A:
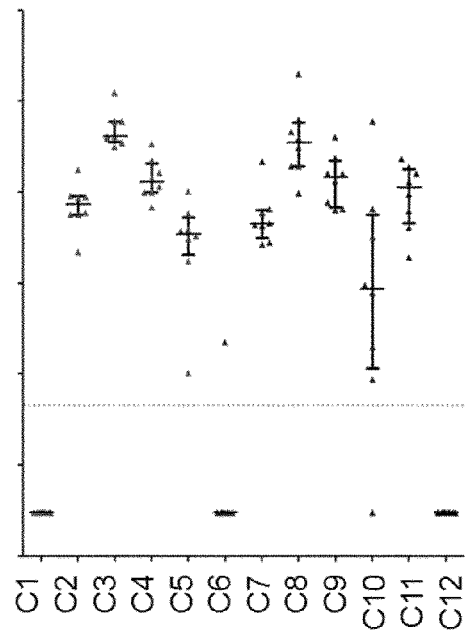
Figure 2B:
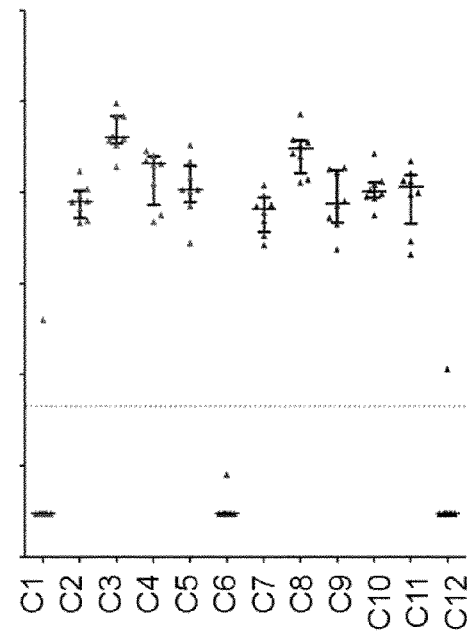
Figure 3A:
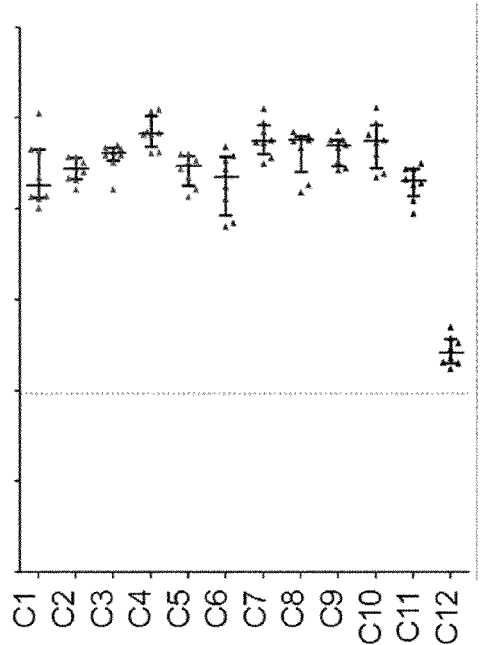
Figure 3B:
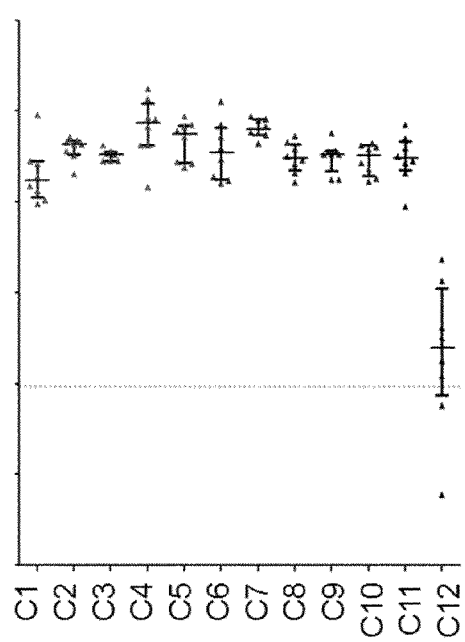
Figure 4A:
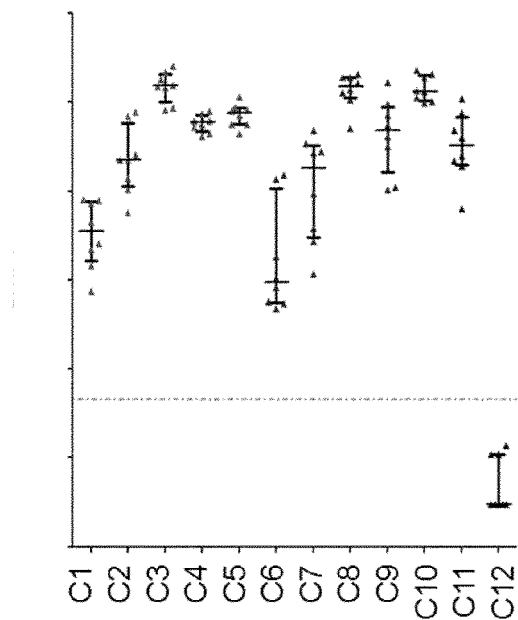
Figure 4B:
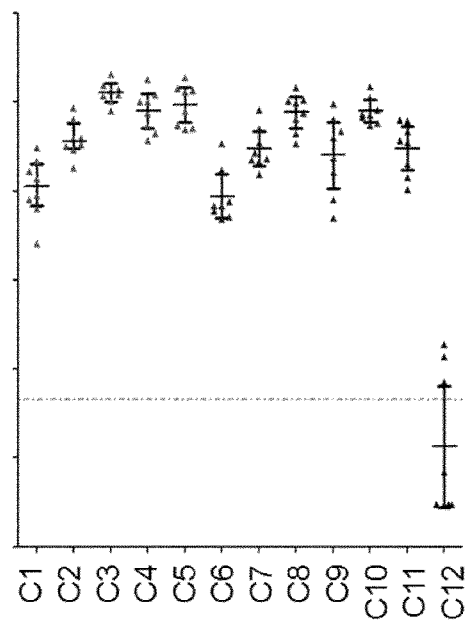
Figure 5A:
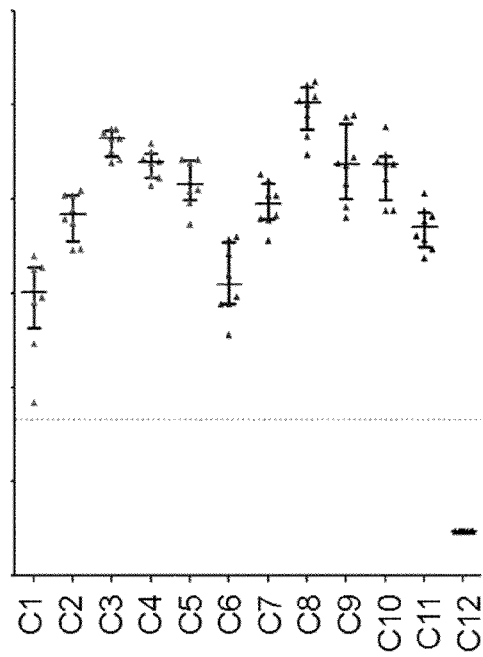
Figure 5B:
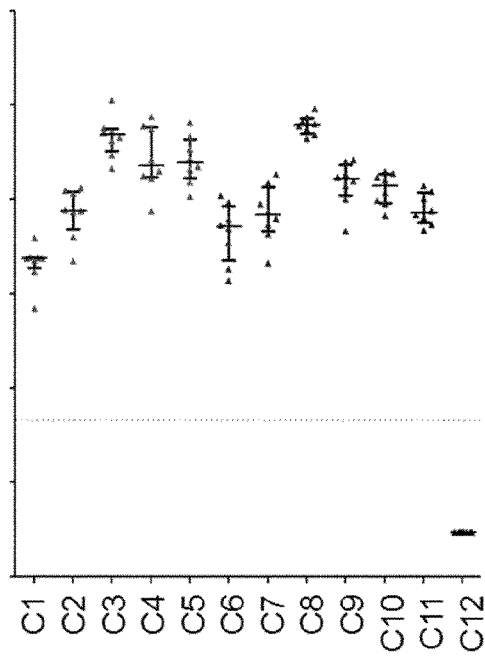
Figure 6:
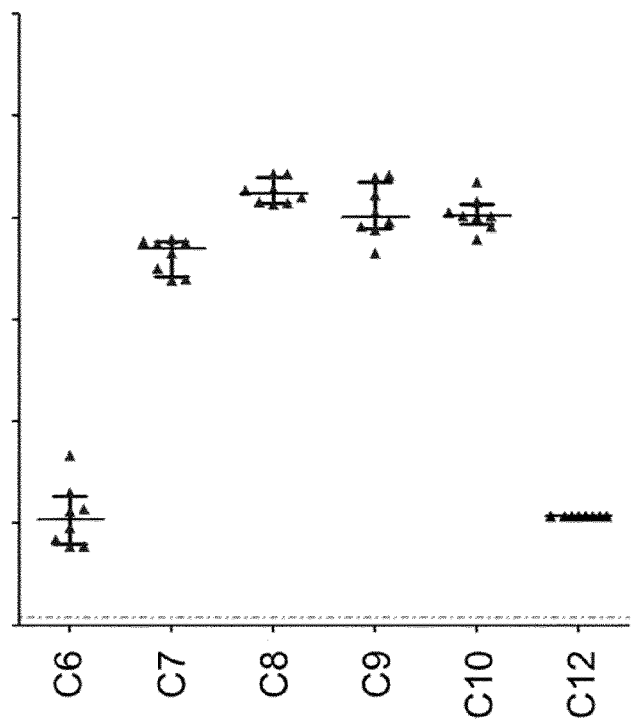
Figure 7:
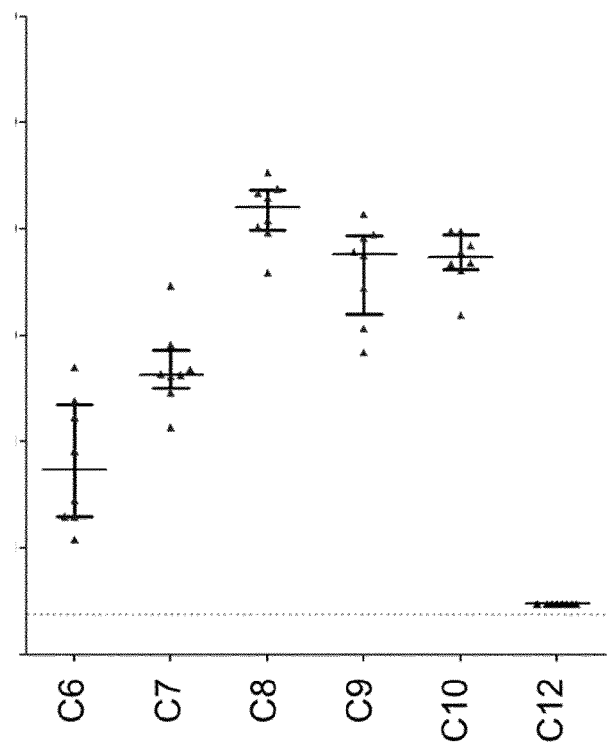
Figure 8:
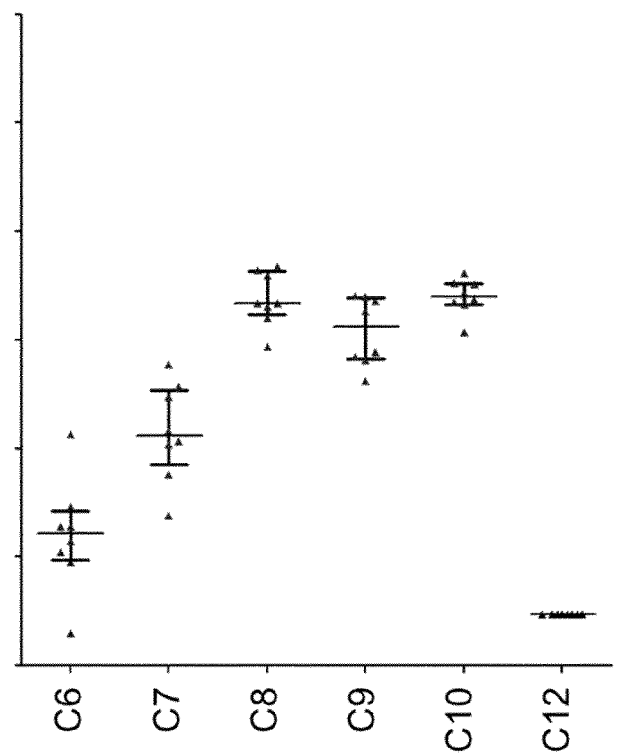

These 12 compositions were administered to female Balb/C mice (6 weeks old) at 100 µl intramuscular doses (2×50 µl) on days 0, 21 and 35. Sera were tested 2 weeks after each dose and assessed for specific IgG responses against each of the 8 immunogens (except that only C6-C10 & C12 were tested for responses against the 3 MenB immunogens). These titers are shown in FIGS. 1-8. FIGS. 1-5 show data for days 35 (1A to 5A) and 49 (1B to 5B), whereas FIGS. 6-8 show data only for day 35.

The data show that the MenB antigens have no negative impact on IgG responses against the diphtheria, tetanus and acellular pertussis antigens after 2 or 3 doses. Furthermore, the inclusion of a TLR agonist with the Al—H adjuvant improved IgG responses against all antigens. The emulsion adjuvant also gave better results than Al—H alone. In all cases however, the adjuvants did not have a large impact on anti-PT responses.

The second dose of vaccine (day 21) led to an increase of IgG response against all antigens, but the third dose (day 35)

did not provide a further significant increase. Thus the studied adjuvants provide a more rapid response to the re-injected antigens, which can be very useful in booster situations.

Thus the mixture of D, T, aP and MenB antigens offers a new and effective combination vaccine.

It will be understood that the invention has been described by way of example only and modifications may be made whilst remaining within the scope and spirit of the invention.

REFERENCES

[1] *Vaccines*. (eds. Plotkin & Orenstein). 4th edition, 2004, ISBN: 0-7216-9688-0.
[2] Insel (1995) *Ann N Y Acad Sci.* 754:35-47.
[3] André (1999) *Vaccine* 17:1620-1627.
[4] Gizurarson (1998) *BioDrugs* 9:443-453.
[5] European Commission COST/STD initiative (1996) *Vaccine* 14:691-700.
[6] Skibinski et al. (2011) *J Global Infect Dis* 3:63-70.
[7] Bai et al. (2011) *Expert Opin Biol Ther.* 11:969-85.
[8] Giuliani et al. (2006) *PNAS USA* 103:10834-9.
[9] Marsh et al. (2011) *Vaccine* 29:6049-58.
[10] Sheldon et al. (2012) *Hum Vaccin Immunother* 8(7).
[11] WO02/09643.
[12] Katial et al. (2002) *Infect. Immun.* 70:702-707.
[13] U.S. Pat. No. 6,180,111.
[14] WO01/34642.
[15] WO2006/046143.
[16] WO2004/019977.
[17] European patent 0011243.
[18] Fredriksen et al. (1991) *NIPH Ann.* 14(2):67-80.
[19] WO01/91788.
[20] WO2005/004908.
[21] WO2011/036562.
[22] Claassen et al. (1996) *Vaccine* 14:1001-8.
[23] de Kleijn et al. (2000) *Vaccine* 18:1456-66.
[24] WO03/105890.
[25] WO2006/024946
[26] Tettelin et al. (2000) *Science* 287:1809-1815.
[27] Module 1 of WHO's *The immunological basis for immunization series* (Galazka)
[28] Lyng (1990) *Biologicals* 18:11-17
[29] NIBSC code: 69/017
[30] NIBSC code: DIFT
[31] Sesardic et al. (2001) *Biologicals* 29:107-22
[32] NIBSC code: 98/560
[33] NIBSC code: TEFT
[34] Sesardic et al. (2002) *Biologicals* 30:49-68
[35] NIBSC code: 98/552
[36] Rappuoli et al. (1991) *TIBTECH* 9:232-238.
[37] Nencioni et al. (1991) *Infect Immun.* 59(2): 625-30.
[38] Denoël et al. (2002) *Vaccine* 20:2551-5.
[39] Ramsay et al. (2001) *Lancet* 357(9251):195-196.
[40] Lindberg (1999) *Vaccine* 17 Suppl 2:S28-36.
[41] Buttery & Moxon (2000) *J R Coll Physicians Lond* 34:163-168.
[42] Ahmad & Chapnick (1999) *Infect Dis Clin North Am* 13:113-133, vii.
[43] Goldblatt (1998) *J. Med. Microbiol.* 47:563-567.
[44] European patent 0477508.
[45] U.S. Pat. No. 5,306,492.
[46] WO98/42721.
[47] *Conjugate Vaccines* (eds. Cruse et al.) ISBN 3805549326, particularly vol. 10:48-114.
[48] Hermanson (1996) *Bioconjugate Techniques* ISBN: 0123423368 or 012342335X.
[49] WO96/40242.
[50] Vanlandschoot et al. (2005) *J Gen Virol* 86:323-31.
[51] WO2007/054820.
[52] WO03/066094.
[53] Liao et al. (2012) *J Infect Dis.* 205:237-43.
[54] Verdijk et al. (2011) *Expert Rev Vaccines.* 10:635-44.
[55] Module 6 of WHO's *The immunological basis for immunization series* (Robertson)
[56] *W.H.O. Tech. Rep. Ser.* 594:51, 1976.
[57] WO03/080678.
[58] Glode et al. (1979) *J Infect Dis* 139:52-56
[59] WO94/05325; U.S. Pat. No. 5,425,946.
[60] Arakere & Frasch (1991) *Infect. Immun.* 59:4349-4356.
[61] Michon et al. (2000) *Dev. Biol.* 103:151-160.
[62] Rubinstein & Stein (1998) *J. Immunol.* 141:4357-4362.
[63] WO2005/033148
[64] WO2005/000347.
[65] WO02/058737.
[66] WO03/007985.
[67] WO2007/000314.
[68] WO2007/000322.
[69] *WHO Technical Report Series* No. 927, 2005. Pages 64-98.
[70] US-2008/0102498.
[71] US-2006/0228381.
[72] US-2007/0231340.
[73] US-2007/0184072.
[74] US-2006/0228380.
[75] WO2008/143709.
[76] *Research Disclosure*, 453077 (January 2002)
[77] EP-A-0378881.
[78] EP-A-0427347.
[79] WO93/17712
[80] WO94/03208.
[81] WO98/58668.
[82] EP-A-0471177.
[83] WO91/01146
[84] Falugi et al. (2001) *Eur J Immunol* 31:3816-3824.
[85] Baraldo et al. (2004) *Infect Immun* 72(8):4884-7.
[86] EP-A-0594610.
[87] Ruan et al. (1990) *J Immunol* 145:3379-3384.
[88] WO00/56360.
[89] Kuo et al. (1995) *Infect Immun* 63:2706-13.
[90] Michon et al. (1998) *Vaccine.* 16:1732-41.
[91] WO02/091998.
[92] WO01/72337
[93] WO00/61761.
[94] WO00/33882
[95] WO2007/071707
[96] Bethell G. S. et al., *J. Biol. Chem.*, 1979, 254, 2572-4
[97] Hearn M. T. W., *J. Chromatogr.*, 1981, 218, 509-18
[98] WO2007/000343.
[99] *Mol. Immunol.*, 1985, 22, 907-919
[100] EP-A-0208375
[101] WO00/10599
[102] Geyer et al., Med. Microbiol. Immunol, 165: 171-288 (1979).
[103] U.S. Pat. No. 4,057,685.
[104] U.S. Pat. Nos. 4,673,574; 4,761,283; 4,808,700.
[105] U.S. Pat. No. 4,459,286.
[106] U.S. Pat. No. 5,204,098
[107] U.S. Pat. No. 4,965,338
[108] U.S. Pat. No. 4,663,160.
[109] US-2007/0184071.
[110] Jodar et al. (2003) *Vaccine* 21:3265-72.
[111] WO2011/067669.
[112] WO2011/067672.

[113] WO2011/067673.
[114] WO2008/056263.
[115] WO2011/154442.
[116] WO2011/154443.
[117] WO2011/154444.
[118] WO90/14837.
[119] Podda & Del Giudice (2003) *Expert Rev Vaccines* 2:197-203.
[120] Podda (2001) *Vaccine* 19: 2673-2680.
[121] WO2008/043774.
[122] WO2005/097181.
[123] WO95/11700.
[124] US-2007/014805.
[125] WO2007/080308.
[126] WO2010/023551
[127] Brito et al. (2011) *Vaccine* 29:6262-6268.
[128] U.S. Pat. No. 8,092,813.
[129] WO2011/141819.
[130] U.S. Pat. No. 6,630,161.
[131] *Vaccine Design: The Subunit and Adjuvant Approach* (eds. Powell & Newman) Plenum Press 1995 (ISBN O-306-44867-X).
[132] *Vaccine Adjuvants: Preparation Methods and Research Protocols* (Volume 42 of *Methods in Molecular Medicine* series). ISBN: 1-59259-083-7. Ed. O'Hagan.
[133] Clausi et al. (2008) *J Pharm Sci DOI* 10.1002/jps.21390.
[134] Rosenberg et al. (2010) *J Immunol* 184:136.20.
[135] U.S. Pat. No. 4,666,886.
[136] WO2009/118296.
[137] WO2008/005555.
[138] WO2009/111337.
[139] WO2009/067081.
[140] WO2007/040840.
[141] WO2010/014913.
[142] WO2012/031140.
[143] WO2011/119759.
[144] Steinhagen et al. (2011) *Vaccine* 29:3341-55.
[145] GB-A-2220211.
[146] Myers et al. (1990) pages 145-156 of *Cellular and molecular aspects of endotoxin reactions*.
[147] Ulrich (2000) Chapter 16 (pages 273-282) of reference 132.
[148] Johnson et al. (1999) *J Med Chem* 42:4640-9.
[149] Baldrick et al. (2002) *Regulatory Toxicol Pharmacol* 35:398-413.
[150] Coler et al. (2011) *PLoS ONE* 6(1):e16333.
[151] Johnson et al. (1999) *Bioorg Med Chem Lett* 9:2273-2278.
[152] Evans et al. (2003) *Expert Rev Vaccines* 2:219-229.
[153] Bazin et al. (2006) *Tetrahedron Lett* 47:2087-92.
[154] Wong et al. (2003) *J Clin Pharmacol* 43(7):735-42.
[155] US2005/0215517.
[156] WO03/011223.
[157] WO2007/053455.
[158] Garçon et al. (2007) *Expert Rev Vaccines* 6:723-39.
[159] WO 94/21292.
[160] WO2011/027222.
[161] WO2007/034917.
[162] WO2007/034173.
[163] WO2008/114817.
[164] US2009-0105212.
[165] US2009-0118263.
[166] US2009-0143400.
[167] US2009-0192153.
[168] WO2007/093901.
[169] WO2009/019553.
[170] US2009/0221631.
[171] WO2008/004948.
[172] WO2008/135791.
[173] US2009/0099216.
[174] US2009/0202484.
[175] WO2008/101867.
[176] WO2010/077613.
[177] US2010/0143301.
[178] Nony et al. (2001) *Vaccine* 27:3645-51.
[179] WO01/41800.
[180] PCT/IB2012/050989
[181] Serruto et al. (2010) *PNAS USA* 107:3770-5.
[182] WO00/66741.
[183] WO99/57280.
[184] WO2004/032958.
[185] Masignani et al. (2003) *J Exp Med* 197:789-799.
[186] Welsch et al. (2004) *J Immunol* 172:5605-15.
[187] WO03/063766.
[188] Fletcher et al. (2004) *Infect Immun* 72:2088-2100.
[189] Zhu et al. (2005) *Infect Immun* 73(10):6838-45.
[190] Cantini et al. (2006) *J. Biol. Chem.* 281:7220-7227
[191] WO2004/048404
[192] WO2009/104097.
[193] WO2011/024072.
[194] Giuliani et al. (2006) *PNAS USA* 103:10834-9.
[195] U.S. Pat. No. 5,698,438.
[196] WO2010/070453.
[197] Perkins-Balding et al. (2003) *Microbiology* 149:3423-35.
[198] Martin et al. (1997) *J Exp Med* 185(7):1173-83.
[199] WO96/29412.
[200] WO01/55182.
[201] WO01/38350.
[202] WO00/23595.
[203] WO2010/025964.
[204] WO2011/110655.
[205] Koeberling et al. (2007) *Vaccine* 25:1912-20.
[206] Koeberling et al. (2008) *J Infect Dis* 198:262-70.
[207] Hou et al. (2005) *J Infect Dis* 192:580-90.
[208] WO2009/038889.
[209] Bonvehi et al. (2010) *Clin Vacc Immunol* 17:1460-6.
[210] Zollinger et al. (2010) *Vaccine* 28:5057-67.
[211] WO99/10497.
[212] Steeghs et al. (2001) *The EMBO Journal* 20:6937-6945.
[213] Maiden et al. (1998) *PNAS USA* 95:3140-3145.
[214] WO01/09350.
[215] WO02/062378.
[216] WO2004/014417.
[217] WO00/26384.
[218] U.S. Pat. No. 6,531,131
[219] U.S. Pat. No. 6,645,503
[220] WO2004/015099.
[221] WO2006/081259.
[222] Deghmane et al. (2003) *Infect Immun* 71:2897-901.
[223] Schielke et al. (2009) *Mol Microbiol* 72:1054-67.
[224] WO2004/014418.
[225] WO00/25811.
[226] WO02/09746.
[227] Oriente et al. (2010) *J Bacteriol* 192:691-701.
[228] WO2011/039631.
[229] Donnelly et al. (2010) *PNAS USA* 107:19490-5.
[230] Kimura et al. (2010) *Clin Vaccine Immunol.* 2010 PMID: 21177912.
[231] Pinto et al. (2011) *Vaccine* 29:7752-58.
[232] Moran et al. (2012) *Clin Vaccine Immunol* 19:659-665.

The invention claimed is:

1. An immunogenic composition, comprising: (a) a recombinant or purified serogroup B meningococcus immunogen, wherein the serogroup B meningococcus immunogen comprises a meningococcal factor H binding protein (fHbp) or a polypeptide having at least 85% sequence identity to SEQ ID NO: 4 or SEQ ID NO: 19; (b) a diphtheria toxoid, a tetanus toxoid, and a pertussis toxoid, wherein the tetanus toxoid is present in an excess relative to diphtheria toxoid as measured in Lf units; and (c) an adjuvant, wherein the adjuvant comprises an oil-in-water emulsion.

2. The composition of claim 1, further comprising in component (a) a Neisserial Heparin Binding Antigen (NHBA) protein or a polypeptide having at least 85% sequence identity to SEQ ID NO: 5 and a Neisserial adhesin A (NadA) protein or a polypeptide having at least 85% sequence identity to SEQ ID NO: 6.

3. The composition of claim 1, wherein the fHbp protein or the polypeptide is located in a meningococcal vesicle.

4. A method of raising an immune response in a mammalian subject, comprising the step of administering an effective amount of the composition of claim 1 to the subject.

5. An immunogenic composition, comprising: (a) a recombinant or purified serogroup B meningococcus immunogen, wherein the serogroup B meningococcus immunogen comprises a meningococcal fHbp protein or a polypeptide having at least 85% sequence identity to SEQ ID NO: 4 or SEQ ID NO: 19; (b) a diphtheria toxoid, a tetanus toxoid, and a pertussis toxoid, wherein the tetanus toxoid is present in an excess relative to diphtheria toxoid as measured in Lf units; and (c) an adjuvant, wherein the adjuvant comprises an aluminium salt and a TLR agonist wherein the TLR agonist is adsorbed to the aluminium salt.

6. The composition of claim 5, wherein the adjuvant further comprises an oil-in-water emulsion.

7. The composition of claim 5, further comprising in component (a) a NHBA protein or a polypeptide having at least 85% sequence identity to SEQ ID NO: 5 and a NadA protein or a polypeptide having at least 85% sequence identity to SEQ ID NO: 6.

8. The composition of claim 5, wherein the fHbp protein or the polypeptide having at least 85% sequence identity to SEQ ID NO: 4 or SEQ ID NO: 19 is located in a meningococcal vesicle.

9. The composition of claim 5, wherein the TLR agonist is a TLR4 agonist, a TLR7 agonist, or a combination thereof.

10. The composition of claim 9, wherein the TLR agonist is a TLR7 agonist.

11. The composition of claim 10, wherein the TLR7 agonist is 3-(5-amino-2-(2-methyl-4-(2-(2-(2-phosphonoethoxy)ethoxy)ethoxy)phenethyl)benzo[f]-[1,7]naphthyridin-8-yl)propanoic acid, or a salt thereof.

* * * * *

SEQUENCE LISTING

<160> NUMBER OF SEQ ID NOS: 29

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln

```
                65                  70                  75                  80
        Leu Ile Thr Leu Glu Ser Gly Glu Phe Gln Ile Tyr Lys Gln Asp His
                        85                  90                  95

Ser Ala Val Ala Leu Gln Ile Glu Lys Ile Asn Asn Pro Asp Lys
                    100                 105                 110

Ile Asp Ser Leu Ile Asn Gln Arg Ser Phe Leu Val Ser Gly Leu Gly
                115                 120                 125

Gly Glu His Thr Ala Phe Asn Gln Leu Pro Asp Gly Lys Ala Glu Tyr
            130                 135                 140

His Gly Lys Ala Phe Ser Ser Asp Asp Ala Gly Lys Leu Thr Tyr
        145                 150                 155                 160

Thr Ile Asp Phe Ala Ala Lys Gln Gly His Gly Lys Ile Glu His Leu
                        165                 170                 175

Lys Thr Pro Glu Gln Asn Val Glu Leu Ala Ala Ala Glu Leu Lys Ala
                    180                 185                 190

Asp Glu Lys Ser His Ala Val Ile Leu Gly Asp Thr Arg Tyr Gly Ser
                195                 200                 205

Glu Glu Lys Gly Thr Tyr His Leu Ala Leu Phe Gly Asp Arg Ala Gln
            210                 215                 220

Glu Ile Ala Gly Ser Ala Thr Val Lys Ile Gly Glu Lys Val His Glu
        225                 230                 235                 240

Ile Gly Ile Ala Gly Lys Gln
                        245

<210> SEQ ID NO 3
<211> LENGTH: 250
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
        1               5                   10                  15

Leu Asp His Lys Asp Lys Gly Leu Lys Ser Leu Thr Leu Glu Asp Ser
                        20                  25                  30

Ile Pro Gln Asn Gly Thr Leu Thr Leu Ser Ala Gln Gly Ala Glu Lys
                    35                  40                  45

Thr Phe Lys Ala Gly Asp Lys Asp Asn Ser Leu Asn Thr Gly Lys Leu
                50                  55                  60

Lys Asn Asp Lys Ile Ser Arg Phe Asp Phe Val Gln Lys Ile Glu Val
        65                  70                  75                  80

Asp Gly Gln Thr Ile Thr Leu Ala Ser Gly Glu Phe Gln Ile Tyr Lys
                        85                  90                  95

Gln Asn His Ser Ala Val Val Ala Leu Gln Ile Glu Lys Ile Asn Asn
                    100                 105                 110

Pro Asp Lys Thr Asp Ser Leu Ile Asn Gln Arg Ser Phe Leu Val Ser
                115                 120                 125

Gly Leu Gly Gly Glu His Thr Ala Phe Asn Gln Leu Pro Gly Gly Lys
            130                 135                 140

Ala Glu Tyr His Gly Lys Ala Phe Ser Ser Asp Asp Pro Asn Gly Arg
        145                 150                 155                 160

Leu His Tyr Ser Ile Asp Phe Thr Lys Lys Gln Gly Tyr Gly Arg Ile
                        165                 170                 175

Glu His Leu Lys Thr Leu Glu Gln Asn Val Glu Leu Ala Ala Ala Glu
                    180                 185                 190
```

```
Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
            210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
            245                 250

<210> SEQ ID NO 4
<211> LENGTH: 644
<212> TYPE: PRT
<213> ORGANISM: Artificial Sequence
<220> FEATURE:
<223> OTHER INFORMATION: Hybrid protein

<400> SEQUENCE: 4

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300
```

```
Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln
```

<210> SEQ ID NO 5
<211> LENGTH: 434
<212> TYPE: PRT
<213> ORGANISM: Artificial Sequence
<220> FEATURE:
<223> OTHER INFORMATION: Hybrid protein

<400> SEQUENCE: 5

```
Met Val Ser Ala Val Ile Gly Ser Ala Ala Gly Ala Lys Ser Ala
1               5                   10                  15

Val Asp Arg Arg Thr Thr Gly Ala Gln Thr Asp Asp Asn Val Met Ala
```

```
                    20                  25                  30
Leu Arg Ile Glu Thr Thr Ala Arg Ser Tyr Leu Arg Gln Asn Asn Gln
            35                  40                  45
Thr Lys Gly Tyr Thr Pro Gln Ile Ser Val Val Gly Tyr Asp Arg His
        50                  55                  60
Leu Leu Leu Leu Gly Gln Val Ala Thr Glu Gly Lys Gln Phe Val
65                  70                  75                  80
Gly Gln Ile Ala Arg Ser Glu Gln Ala Glu Gly Val Tyr Asn Tyr
                85                  90                  95
Ile Thr Val Ala Ser Leu Pro Arg Thr Ala Gly Asp Ile Ala Gly Asp
            100                 105                 110
Thr Trp Asn Thr Ser Lys Val Arg Ala Thr Leu Leu Gly Ile Ser Pro
        115                 120                 125
Ala Thr Arg Ala Arg Val Lys Ile Val Thr Tyr Gly Asn Val Thr Tyr
        130                 135                 140
Val Met Gly Ile Leu Thr Pro Glu Gln Ala Gln Ile Thr Gln Lys
145                 150                 155                 160
Val Ser Thr Thr Val Gly Val Gln Lys Val Ile Thr Leu Tyr Gln Asn
                165                 170                 175
Tyr Val Gln Arg Gly Ser Gly Gly Gly Val Ala Ala Asp Ile Gly
            180                 185                 190
Ala Gly Leu Ala Asp Ala Leu Thr Ala Pro Leu Asp His Lys Asp Lys
        195                 200                 205
Gly Leu Gln Ser Leu Thr Leu Asp Gln Ser Val Arg Lys Asn Glu Lys
    210                 215                 220
Leu Lys Leu Ala Ala Gln Gly Ala Glu Lys Thr Tyr Gly Asn Gly Asp
225                 230                 235                 240
Ser Leu Asn Thr Gly Lys Leu Lys Asn Asp Lys Val Ser Arg Phe Asp
                245                 250                 255
Phe Ile Arg Gln Ile Glu Val Asp Gly Gln Leu Ile Thr Leu Glu Ser
            260                 265                 270
Gly Glu Phe Gln Val Tyr Lys Gln Ser His Ser Ala Leu Thr Ala Phe
        275                 280                 285
Gln Thr Glu Gln Ile Gln Asp Ser Glu His Ser Gly Lys Met Val Ala
        290                 295                 300
Lys Arg Gln Phe Arg Ile Gly Asp Ile Ala Gly Glu His Thr Ser Phe
305                 310                 315                 320
Asp Lys Leu Pro Glu Gly Gly Arg Ala Thr Tyr Arg Gly Thr Ala Phe
                325                 330                 335
Gly Ser Asp Asp Ala Gly Gly Lys Leu Thr Tyr Thr Ile Asp Phe Ala
            340                 345                 350
Ala Lys Gln Gly Asn Gly Lys Ile Glu His Leu Lys Ser Pro Glu Leu
        355                 360                 365
Asn Val Asp Leu Ala Ala Ala Asp Ile Lys Pro Asp Gly Lys Arg His
        370                 375                 380
Ala Val Ile Ser Gly Ser Val Leu Tyr Asn Gln Ala Glu Lys Gly Ser
385                 390                 395                 400
Tyr Ser Leu Gly Ile Phe Gly Gly Lys Ala Gln Glu Val Ala Gly Ser
                405                 410                 415
Ala Glu Val Lys Thr Val Asn Gly Ile Arg His Ile Gly Leu Ala Ala
            420                 425                 430
Lys Gln
```

<210> SEQ ID NO 6
<211> LENGTH: 327
<212> TYPE: PRT
<213> ORGANISM: Neisseria meningitidis

<400> SEQUENCE: 6

```
Ala Thr Asn Asp Asp Val Lys Lys Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```

<210> SEQ ID NO 7
<211> LENGTH: 792
<212> TYPE: PRT
<213> ORGANISM: Neisseria meningitidis

<400> SEQUENCE: 7

```
Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
            35                  40                  45

Ala Pro Ala Ala Val Glu Arg Val Asn Leu Asn Arg Ile Lys Gln Glu
50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Glu Ile Val Lys
            130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
            210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
            275                 280                 285

Tyr Asn Leu Thr Ala Ser Ser Trp Arg Glu Ala Asp Asp Val Asn Arg
            290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
            325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
            355                 360                 365

Asp Thr Arg Phe Lys Arg Phe Thr Leu Arg Leu Asp Ser His Pro Leu
            370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
            405                 410                 415

Arg Val Val Arg Thr Thr Ser Ser Ile Gln His Pro Val Lys Thr Thr
```

```
            420                 425                 430
Asn Tyr Gly Phe Ser Leu Ser Asp Gln Ile Gln Trp Asn Asp Val Phe
        435                 440                 445

Ser Ser Arg Ala Gly Ile Arg Tyr Asp His Thr Lys Met Thr Pro Gln
450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                485                 490                 495

Asn Gln Ala Trp Arg Val Gly Tyr Asp Ile Thr Ser Gly Tyr Arg Val
                500                 505                 510

Pro Asn Ala Ser Glu Val Tyr Phe Thr Tyr Asn His Gly Ser Gly Asn
            515                 520                 525

Trp Leu Pro Asn Pro Asn Leu Lys Ala Glu Arg Ser Thr Thr His Thr
            530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Gln Lys Leu Thr
                565                 570                 575

Thr Ser Gly Thr Pro Gly Cys Thr Glu Glu Asn Ala Tyr Tyr Gly Ile
                580                 585                 590

Cys Ser Asp Pro Tyr Lys Glu Lys Leu Asp Trp Gln Met Lys Asn Ile
                595                 600                 605

Asp Lys Ala Arg Ile Arg Gly Ile Glu Leu Thr Gly Arg Leu Asn Val
            610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
                660                 665                 670

Glu Lys Trp Gly Val Phe Ser Arg Leu Thr Tyr Leu Gly Ala Lys Lys
            675                 680                 685

Val Lys Asp Ala Gln Tyr Thr Val Tyr Glu Asn Lys Gly Trp Gly Thr
            690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
                740                 745                 750

Asp Ser Leu Arg Gly Leu Tyr Ser Tyr Ser Thr Thr Asn Ala Val Asp
                755                 760                 765

Arg Asp Gly Lys Gly Leu Asp Arg Tyr Arg Ala Pro Gly Arg Asn Tyr
770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8
```

```
Met Lys Pro Leu Gln Met Leu Pro Ile Ala Ala Leu Val Gly Ser Ile
1               5                   10                  15

Phe Gly Asn Pro Val Phe Ala Ala Asp Glu Ala Thr Glu Thr Thr
            20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
130                 135                 140

Gly Ala Asp Ser Phe Asn Thr Gly Ser Gly Ala Leu Gly Gly Val
145                 150                 155                 160

Asn Tyr Gln Thr Leu Gln Gly Arg Asp Leu Leu Pro Glu Arg Gln
            165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr Asn His His
            245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
        275                 280                 285

Tyr Asn Leu Leu Ala Ser Tyr Trp Arg Glu Ala Asp Asp Val Asn Arg
        290                 295                 300

Arg Arg Asn Thr Asn Leu Phe Tyr Glu Trp Thr Pro Glu Ser Asp Arg
305                 310                 315                 320

Leu Ser Met Val Lys Ala Asp Val Asp Tyr Gln Lys Thr Lys Val Ser
            325                 330                 335

Ala Val Asn Tyr Lys Gly Ser Phe Pro Ile Glu Asp Ser Ser Thr Leu
            340                 345                 350

Thr Arg Asn Tyr Asn Gln Lys Asp Leu Asp Glu Ile Tyr Asn Arg Ser
        355                 360                 365

Met Asp Thr Arg Phe Lys Arg Ile Thr Leu Arg Leu Asp Ser His Pro
370                 375                 380

Leu Gln Leu Gly Gly Arg His Arg Leu Ser Phe Lys Thr Phe Ala
385                 390                 395                 400

Ser Arg Arg Asp Phe Glu Asn Leu Asn Arg Asp Asp Tyr Tyr Phe Ser
            405                 410                 415

Gly Arg Val Val Arg Thr Thr Ser Ser Ile Gln His Pro Val Lys Thr
```

```
                420             425             430
Thr Asn Tyr Gly Phe Ser Leu Ser Asp Gln Ile Gln Trp Asn Asp Val
            435             440             445
Phe Ser Ser Arg Ala Gly Ile Arg Tyr Asp His Thr Lys Met Thr Pro
450             455             460
Gln Glu Leu Asn Ala Glu Cys His Ala Cys Asp Lys Thr Pro Pro Ala
465             470             475             480
Ala Asn Thr Tyr Lys Gly Trp Ser Gly Phe Val Gly Leu Ala Ala Gln
            485             490             495
Leu Asn Gln Ala Trp Arg Val Gly Tyr Asp Ile Thr Ser Gly Tyr Arg
        500             505             510
Val Pro Asn Ala Ser Glu Val Tyr Phe Thr Tyr Asn His Gly Ser Gly
        515             520             525
Asn Trp Leu Pro Asn Pro Asn Leu Lys Ala Glu Arg Thr Thr Thr His
        530             535             540
Thr Leu Ser Leu Gln Gly Arg Ser Glu Lys Gly Thr Leu Asp Ala Asn
545             550             555             560
Leu Tyr Gln Ser Asn Tyr Arg Asn Phe Leu Ser Glu Glu Gln Lys Leu
            565             570             575
Thr Thr Ser Gly Asp Val Ser Cys Thr Gln Met Asn Tyr Tyr Tyr Gly
            580             585             590
Met Cys Ser Asn Pro Tyr Ser Glu Lys Leu Glu Trp Gln Met Gln Asn
        595             600             605
Ile Asp Lys Ala Arg Ile Arg Gly Ile Glu Leu Thr Gly Arg Leu Asn
        610             615             620
Val Asp Lys Val Ala Ser Phe Val Pro Glu Gly Trp Lys Leu Phe Gly
625             630             635             640
Ser Leu Gly Tyr Ala Lys Ser Lys Leu Ser Gly Asp Asn Ser Leu Leu
            645             650             655
Ser Thr Gln Pro Leu Lys Val Ile Ala Gly Ile Asp Tyr Glu Ser Pro
            660             665             670
Ser Glu Lys Trp Gly Val Phe Ser Arg Leu Thr Tyr Leu Gly Ala Lys
            675             680             685
Lys Val Lys Asp Ala Gln Tyr Thr Val Tyr Glu Asn Lys Gly Trp Gly
        690             695             700
Thr Pro Leu Gln Lys Lys Val Lys Asp Tyr Pro Trp Leu Asn Lys Ser
705             710             715             720
Ala Tyr Val Phe Asp Met Tyr Gly Phe Tyr Lys Pro Val Lys Asn Leu
            725             730             735
Thr Leu Arg Ala Gly Val Tyr Asn Val Phe Asn Arg Lys Tyr Thr Thr
            740             745             750
Trp Asp Ser Leu Arg Gly Leu Tyr Ser Tyr Ser Thr Thr Asn Ser Val
        755             760             765
Asp Arg Asp Gly Lys Gly Leu Asp Arg Tyr Arg Ala Pro Ser Arg Asn
        770             775             780
Tyr Ala Val Ser Leu Glu Trp Lys Phe
785             790

<210> SEQ ID NO 9
<211> LENGTH: 488
<212> TYPE: PRT
<213> ORGANISM: Neisseria meningitidis

<400> SEQUENCE: 9
```

```
Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
            130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
            165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
            195                 200                 205

Asn Gly Val Leu Ile Asp Gly Pro Ser Gln Asn Ile Thr Leu Thr His
            210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
            245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
            290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
            325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
            370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
            405                 410                 415

Asp Ser Gly Asp Asp Leu His Met Gly Thr Gln Lys Phe Lys Ala Ala
```

```
                420             425             430
Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Val Ala Gly
        450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
            485

<210> SEQ ID NO 10
<211> LENGTH: 364
<212> TYPE: PRT
<213> ORGANISM: Neisseria meningitidis

<400> SEQUENCE: 10

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300
```

```
Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
            325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360
```

<210> SEQ ID NO 11
<211> LENGTH: 174
<212> TYPE: PRT
<213> ORGANISM: Neisseria meningitidis

<400> SEQUENCE: 11

```
Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170
```

<210> SEQ ID NO 12
<211> LENGTH: 591
<212> TYPE: PRT
<213> ORGANISM: Neisseria meningitidis

<400> SEQUENCE: 12

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95
```

-continued

```
Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
```

```
                515                 520                 525
Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 13
<211> LENGTH: 1457
<212> TYPE: PRT
<213> ORGANISM: Neisseria meningitidis

<400> SEQUENCE: 13

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300
```

-continued

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
            325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
            355                 360                 365

Glu Thr Ala Arg Glu Pro Val Tyr His Ala Ala Gly Gly Val Asn Ser
370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
                420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
            565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
            645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
        690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn

```
            725                 730                 735
Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
            850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg Arg Ser Leu Leu
            930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
                980                 985                 990

Gly Thr Tyr Thr Leu Ala Val Asn Asn Thr Gly Asn Glu Pro Ala Ser
                995                1000                1005

Leu Glu Gln Leu Thr Val Val Glu Gly Lys Asp Asn Lys Pro Leu Ser
            1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
                1060                1065                1070

Lys Lys Gln Ala Glu Lys Asp Asn Ala Gln Ser Leu Asp Ala Leu Ile
            1075                1080                1085

Ala Ala Gly Arg Asp Ala Val Glu Lys Thr Glu Ser Val Ala Glu Pro
            1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
            1140                1145                1150
```

-continued

```
Arg Ala Arg Arg Asp Leu Pro Gln Leu Gln Pro Gln Pro Gln
        1155                1160                1165

Pro Gln Arg Asp Leu Ile Ser Arg Tyr Ala Asn Ser Gly Leu Ser Glu
1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
        1205                1210                1215

Arg Asp Thr Lys His Tyr Arg Ser Gln Asp Phe Arg Ala Tyr Arg Gln
        1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
        1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
        1285                1290                1295

Phe Ser Ser Gly Ser Leu Ser Asp Gly Ile Gly Gly Lys Ile Arg Arg
        1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
        1365                1370                1375

Pro Ala Gln His Ile Ser Ile Thr Pro Tyr Leu Ser Leu Ser Tyr Thr
        1380                1385                1390

Asp Ala Ala Ser Gly Lys Val Arg Thr Arg Val Asn Thr Ala Val Leu
        1395                1400                1405

Ala Gln Asp Phe Gly Lys Thr Arg Ser Ala Glu Trp Gly Val Asn Ala
        1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
        1445                1450                1455

Trp

<210> SEQ ID NO 14
<211> LENGTH: 797
<212> TYPE: PRT
<213> ORGANISM: Neisseria meningitidis

<400> SEQUENCE: 14

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60
```

```
Leu Tyr Ala Thr Gly Phe Phe Asp Asp Val Arg Val Glu Thr Ala Asp
 65                  70                  75                  80

Gly Gln Leu Leu Leu Thr Val Ile Glu Arg Pro Thr Ile Gly Ser Leu
                 85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480
```

Asp Gly Val Ser Leu Gly Tyr Asp Val Tyr Gly Lys Ala Phe Asp Pro
            485                 490                 495

Arg Lys Ala Ser Thr Ser Ile Lys Gln Tyr Lys Thr Thr Thr Ala Gly
        500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
        530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
    610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
        755                 760                 765

Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795

<210> SEQ ID NO 15
<211> LENGTH: 791
<212> TYPE: PRT
<213> ORGANISM: Neisseria meningitidis

<400> SEQUENCE: 15

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

-continued

```
Met Ile Arg Asp Asn Lys Asp Leu Val Arg Tyr Ser Thr Asp Val Gly
 65                  70                  75                  80

Leu Ser Asp Ser Gly Arg His Gln Lys Gly Phe Ala Val Arg Gly Val
                 85                  90                  95

Glu Gly Asn Arg Val Gly Val Ser Ile Asp Gly Val Asn Leu Pro Asp
                100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Glu Ile Val Lys
        130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
        210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr His Ser Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
            275                 280                 285

Asn Leu Thr Ala Ser Ser Trp Arg Glu Ala Asp Asp Val Asn Arg Arg
        290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Val Asn Asn Lys Gly Ser Phe Pro Met Asp Tyr Ser Thr Trp Thr Arg
                340                 345                 350

Asn Tyr Asn Gln Lys Asp Leu Asp Glu Ile Tyr Asn Arg Ser Met Asp
            355                 360                 365

Thr Arg Phe Lys Arg Phe Thr Leu Arg Leu Asp Ser His Pro Leu Gln
        370                 375                 380

Leu Gly Gly Gly Arg His Arg Leu Ser Phe Lys Thr Phe Val Ser Arg
385                 390                 395                 400

Arg Asp Phe Glu Asn Leu Asn Arg Asp Tyr Tyr Phe Ser Gly Arg
                405                 410                 415

Val Val Arg Thr Thr Ser Ser Ile Gln His Pro Val Lys Thr Thr Asn
                420                 425                 430

Tyr Gly Phe Ser Leu Ser Asp Gln Ile Gln Trp Asn Asp Val Phe Ser
            435                 440                 445

Ser Arg Ala Gly Ile Arg Tyr Asp His Thr Lys Met Thr Pro Gln Glu
        450                 455                 460

Leu Asn Ala Glu Cys His Ala Cys Asp Lys Thr Pro Pro Ala Ala Asn
465                 470                 475                 480
```

Thr Tyr Lys Gly Trp Ser Gly Phe Val Gly Leu Ala Ala Gln Leu Asn
                485                 490                 495

Gln Ala Trp His Val Gly Tyr Asp Ile Thr Ser Gly Tyr Arg Val Pro
            500                 505                 510

Asn Ala Ser Glu Val Tyr Phe Thr Tyr Asn His Gly Ser Gly Asn Trp
        515                 520                 525

Leu Pro Asn Pro Asn Leu Lys Ala Glu Arg Ser Thr Thr His Thr Leu
    530                 535                 540

Ser Leu Gln Gly Arg Ser Glu Lys Gly Met Leu Asp Ala Asn Leu Tyr
545                 550                 555                 560

Gln Ser Asn Tyr Arg Asn Phe Leu Ser Glu Glu Gln Lys Leu Thr Thr
                565                 570                 575

Ser Gly Thr Pro Gly Cys Thr Glu Glu Asn Ala Tyr Tyr Gly Ile Cys
            580                 585                 590

Ser Asp Pro Tyr Lys Glu Lys Leu Asp Trp Gln Met Lys Asn Ile Asp
        595                 600                 605

Lys Ala Arg Ile Arg Gly Ile Glu Leu Thr Gly Arg Leu Asn Val Asp
    610                 615                 620

Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
            660                 665                 670

Lys Trp Gly Val Phe Ser Arg Leu Thr Tyr Leu Gly Ala Lys Lys Ala
        675                 680                 685

Lys Asp Ala Gln Tyr Thr Val Tyr Glu Asn Lys Gly Trp Gly Thr Pro
    690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Val Phe Asn Arg Lys Tyr Thr Thr Trp Asp
            740                 745                 750

Ser Leu Arg Gly Leu Tyr Ser Tyr Ser Thr Thr Asn Ser Val Asp Arg
        755                 760                 765

Asp Gly Lys Gly Leu Asp Arg Tyr Arg Ala Pro Ser Arg Asn Tyr Ala
    770                 775                 780

Val Ser Leu Glu Trp Lys Phe
785                 790

<210> SEQ ID NO 16
<211> LENGTH: 915
<212> TYPE: PRT
<213> ORGANISM: Neisseria meningitidis

<400> SEQUENCE: 16

Met Gln Gln Gln His Leu Phe Arg Phe Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

```
Ser Asp Thr Leu Ser Lys Glu Gln Val Leu Asn Ile Arg Asp Leu Thr
 65                  70                  75                  80

Arg Tyr Asp Pro Gly Ile Ala Val Val Glu Gln Gly Arg Gly Ala Ser
                 85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
            115                 120                 125

Gly Gly Thr Arg Thr Ala Gly Ser Ser Gly Ala Ile Asn Glu Ile Glu
            130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
            195                 200                 205

Leu Ala Gly Arg Ile Gly Gly Ala Glu Ala Leu Leu Ile His Thr Gly
            210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Asn Tyr Ala
                245                 250                 255

Tyr Phe Ile Val Lys Glu Glu Cys Lys Asn Gly Ser Tyr Glu Thr Cys
            260                 265                 270

Lys Ala Asn Pro Lys Lys Asp Val Val Gly Lys Asp Glu Arg Gln Thr
            275                 280                 285

Val Ser Thr Arg Asp Tyr Thr Gly Pro Asn Arg Phe Leu Ala Asp Pro
290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Lys Lys Gln Ala Gly Ser Leu Pro Gly Asn Gly
            355                 360                 365

Lys Tyr Ala Gly Asn His Lys Tyr Gly Gly Leu Phe Thr Asn Gly Glu
            370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
            435                 440                 445

Asp Gly Ser Asp Lys Tyr Cys Arg Pro Ser Ala Asp Lys Pro Phe Ser
            450                 455                 460

Tyr Tyr Lys Ser Asp Arg Val Ile Tyr Gly Glu Ser His Arg Leu Leu
465                 470                 475                 480
```

```
Gln Ala Ala Phe Lys Lys Ser Phe Asp Thr Ala Lys Ile Arg His Asn
                485                 490                 495
Leu Ser Val Asn Leu Gly Phe Asp Arg Phe Gly Ser Asn Leu Arg His
            500                 505                 510
Gln Asp Tyr Tyr Tyr Gln His Ala Asn Arg Ala Tyr Ser Ser Asn Thr
        515                 520                 525
Pro Pro Gln Asn Asn Gly Lys Lys Ile Ser Pro Asn Gly Ser Glu Thr
    530                 535                 540
Ser Pro Tyr Trp Val Thr Ile Gly Arg Gly Asn Val Val Thr Gly Gln
545                 550                 555                 560
Ile Cys Arg Leu Gly Asn Asn Thr Tyr Thr Asp Cys Thr Pro Arg Ser
                565                 570                 575
Ile Asn Gly Lys Ser Tyr Tyr Ala Ala Val Arg Asp Asn Val Arg Leu
            580                 585                 590
Gly Arg Trp Ala Asp Val Gly Ala Gly Leu Arg Tyr Asp Tyr Arg Ser
        595                 600                 605
Thr His Ser Asp Asp Gly Ser Val Ser Thr Gly Thr His Arg Thr Leu
    610                 615                 620
Ser Trp Asn Ala Gly Ile Val Leu Lys Pro Thr Asp Trp Leu Asp Leu
625                 630                 635                 640
Thr Tyr Arg Thr Ser Thr Gly Phe Arg Leu Pro Ser Phe Ala Glu Met
                645                 650                 655
Tyr Gly Trp Arg Ala Gly Val Gln Ser Lys Ala Val Lys Ile Asp Pro
            660                 665                 670
Glu Lys Ser Phe Asn Lys Glu Ala Gly Ile Val Phe Lys Gly Asp Phe
        675                 680                 685
Gly Asn Leu Glu Ala Ser Trp Phe Asn Asn Ala Tyr Arg Asp Leu Ile
    690                 695                 700
Val Arg Gly Tyr Glu Ala Gln Ile Lys Asp Gly Lys Glu Ala Lys
705                 710                 715                 720
Gly Asp Pro Ala Tyr Leu Asn Ala Gln Ser Ala Arg Ile Thr Gly Ile
                725                 730                 735
Asn Ile Leu Gly Lys Ile Asp Trp Asn Gly Val Trp Asp Lys Leu Pro
            740                 745                 750
Glu Gly Trp Tyr Ser Thr Phe Ala Tyr Asn Arg Val Arg Val Arg Asp
        755                 760                 765
Ile Lys Lys Arg Ala Asp Arg Thr Asp Ile Gln Ser His Leu Phe Asp
    770                 775                 780
Ala Ile Gln Pro Ser Arg Tyr Val Val Gly Leu Gly Tyr Asp Gln Pro
785                 790                 795                 800
Glu Gly Lys Trp Gly Val Asn Gly Met Leu Thr Tyr Ser Lys Ala Lys
                805                 810                 815
Glu Ile Thr Glu Leu Leu Gly Ser Arg Ala Leu Leu Asn Gly Asn Ser
            820                 825                 830
Arg Asn Thr Lys Ala Thr Ala Arg Arg Thr Arg Pro Trp Tyr Ile Val
        835                 840                 845
Asp Val Ser Gly Tyr Tyr Thr Val Lys Lys His Phe Thr Leu Arg Ala
    850                 855                 860
Gly Val Tyr Asn Leu Leu Asn Tyr Arg Tyr Val Thr Trp Glu Asn Val
865                 870                 875                 880
Arg Gln Thr Ala Gly Gly Ala Val Asn Gln His Lys Asn Val Gly Val
                885                 890                 895
Tyr Asn Arg Tyr Ala Ala Pro Gly Arg Asn Tyr Thr Phe Ser Leu Glu
```

Met Lys Phe
        915

<210> SEQ ID NO 17
<211> LENGTH: 712
<212> TYPE: PRT
<213> ORGANISM: Neisseria meningitidis

<400> SEQUENCE: 17

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
            20                  25                  30

Val Asp Thr Glu Ala Pro Arg Pro Ala Pro Lys Tyr Gln Asp Val Phe
            35                  40                  45

Ser Glu Lys Pro Gln Ala Gln Lys Asp Gln Gly Gly Tyr Gly Phe Ala
        50                  55                  60

Met Arg Leu Lys Arg Arg Asn Trp Tyr Pro Gln Ala Lys Glu Asp Glu
65                  70                  75                  80

Val Lys Leu Asp Glu Ser Asp Trp Glu Ala Thr Gly Leu Pro Asp Glu
                85                  90                  95

Pro Lys Glu Leu Pro Lys Arg Gln Lys Ser Val Ile Glu Lys Val Glu
            100                 105                 110

Thr Asp Ser Asp Asn Asn Ile Tyr Ser Ser Pro Tyr Leu Lys Pro Ser
        115                 120                 125

Asn His Gln Asn Gly Asn Thr Gly Asn Gly Ile Asn Gln Pro Lys Asn
    130                 135                 140

Gln Ala Lys Asp Tyr Glu Asn Phe Lys Tyr Val Tyr Ser Gly Trp Phe
145                 150                 155                 160

Tyr Lys His Ala Lys Arg Glu Phe Asn Leu Lys Val Glu Pro Lys Ser
                165                 170                 175

Ala Lys Asn Gly Asp Asp Gly Tyr Ile Phe Tyr His Gly Lys Glu Pro
            180                 185                 190

Ser Arg Gln Leu Pro Ala Ser Gly Lys Ile Thr Tyr Lys Gly Val Trp
        195                 200                 205

His Phe Ala Thr Asp Thr Lys Lys Gly Gln Lys Phe Arg Glu Ile Ile
    210                 215                 220

Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
                245                 250                 255

Gln Glu Gly Tyr Gly Phe Thr Ser Asn Leu Glu Val Asp Phe His Asn
            260                 265                 270

Lys Lys Leu Thr Gly Lys Leu Ile Arg Asn Asn Ala Asn Thr Asp Asn
        275                 280                 285

Asn Gln Ala Thr Thr Thr Gln Tyr Tyr Ser Leu Glu Ala Gln Val Thr
    290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Ser Leu
                325                 330                 335

Ser Gly Gly Phe Phe Gly Pro Gln Gly Glu Glu Leu Gly Phe Arg Phe
            340                 345                 350

```
Leu Ser Asp Asp Gln Lys Val Ala Val Gly Ser Ala Lys Thr Lys
        355                 360                 365

Asp Lys Pro Ala Asn Gly Asn Thr Ala Ala Ser Gly Gly Thr Asp
    370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
        435                 440                 445

Gln Ala Asn Gln Gly Thr Asn Gly Gly Thr Ala Phe Thr Arg Lys Phe
    450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
        515                 520                 525

Ala Gly Glu Ser Ser Ser Gln Ala Asp Ala Lys Thr Glu Gln Val Glu
    530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710

<210> SEQ ID NO 18
<211> LENGTH: 186
<212> TYPE: PRT
<213> ORGANISM: Neisseria meningitidis

<400> SEQUENCE: 18

Met Asn Met Lys Thr Leu Leu Ala Leu Ala Val Ser Ala Val Cys Ser
1               5                   10                  15
```

Val Gly Val Ala Gln Ala His Glu His Asn Thr Ile Pro Lys Gly Ala
            20                  25                  30

Ser Ile Glu Val Lys Val Gln Gln Leu Asp Pro Val Asn Gly Asn Lys
        35                  40                  45

Asp Val Gly Thr Val Thr Ile Thr Glu Ser Asn Tyr Gly Leu Val Phe
 50                  55                  60

Thr Pro Asp Leu Gln Gly Leu Ser Glu Gly Leu His Gly Phe His Ile
 65                  70                  75                  80

His Glu Asn Pro Ser Cys Glu Pro Lys Glu Lys Gly Lys Leu Thr
                 85                  90                  95

Ala Gly Leu Gly Ala Gly Gly His Trp Asp Pro Lys Gly Ala Lys Gln
                100                 105                 110

His Gly Tyr Pro Trp Gln Asp Asp Ala His Leu Gly Asp Leu Pro Ala
            115                 120                 125

Leu Thr Val Leu His Asp Gly Thr Ala Thr Asn Pro Val Leu Ala Pro
130                 135                 140

Arg Leu Lys His Leu Asp Asp Val Arg Gly His Ser Ile Met Ile His
145                 150                 155                 160

Thr Gly Gly Asp Asn His Ser Asp His Pro Ala Pro Leu Gly Gly Gly
                165                 170                 175

Gly Pro Arg Met Ala Cys Gly Val Ile Lys
            180                 185

<210> SEQ ID NO 19
<211> LENGTH: 686
<212> TYPE: PRT
<213> ORGANISM: Artificial Sequence
<220> FEATURE:
<223> OTHER INFORMATION: Hybrid protein

<400> SEQUENCE: 19

Met Val Ser Ala Val Ile Gly Ser Ala Ala Val Gly Ala Lys Ser Ala
 1               5                  10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
 50                  55                  60

Leu Leu Leu Leu Gly Gln Val Ala Thr Glu Gly Glu Lys Gln Phe Val
 65                  70                  75                  80

Gly Gln Ile Ala Arg Ser Glu Gln Ala Ala Glu Gly Val Tyr Asn Tyr
                 85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Arg Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

```
Ala Gly Leu Ala Asp Ala Leu Thr Ala Pro Leu Asp His Lys Asp Lys
            195                 200                 205
Gly Leu Gln Ser Leu Thr Leu Asp Gln Ser Val Arg Lys Asn Glu Lys
        210                 215                 220
Leu Lys Leu Ala Ala Gln Gly Ala Glu Lys Thr Tyr Gly Asn Gly Asp
225                 230                 235                 240
Ser Leu Asn Thr Gly Lys Leu Lys Asn Asp Lys Val Ser Arg Phe Asp
                245                 250                 255
Phe Ile Arg Gln Ile Glu Val Asp Gly Gln Leu Ile Thr Leu Glu Ser
            260                 265                 270
Gly Glu Phe Gln Val Tyr Lys Gln Ser His Ser Ala Leu Thr Ala Phe
        275                 280                 285
Gln Thr Glu Gln Ile Gln Asp Ser Glu His Ser Gly Lys Met Val Ala
        290                 295                 300
Lys Arg Gln Phe Arg Ile Gly Asp Leu Gly Gly Glu His Thr Ala Phe
305                 310                 315                 320
Asn Gln Leu Pro Asp Gly Lys Ala Glu Tyr Arg Gly Thr Ala Phe Gly
                325                 330                 335
Ser Asp Asp Ala Gly Gly Lys Leu Thr Tyr Thr Ile Asp Phe Thr Lys
            340                 345                 350
Lys Gln Gly Asn Gly Lys Ile Glu His Leu Lys Ser Pro Glu Leu Asn
        355                 360                 365
Val Glu Leu Ala Ser Ala Glu Ile Lys Ala Asp Gly Lys Ser His Ala
        370                 375                 380
Val Ile Leu Gly Asp Val Arg Tyr Gly Ser Glu Lys Gly Ser Tyr
385                 390                 395                 400
Ser Leu Gly Ile Phe Gly Gly Arg Ala Gln Glu Val Ala Gly Ser Ala
                405                 410                 415
Glu Val Lys Thr Val Asn Gly Ile Arg His Ile Gly Leu Ala Ala Lys
            420                 425                 430
Gln Gly Ser Gly Gly Gly Val Ala Ala Asp Ile Gly Ala Gly Leu
        435                 440                 445
Ala Asp Ala Leu Thr Ala Pro Leu Asp His Lys Asp Lys Gly Leu Gln
        450                 455                 460
Ser Leu Thr Leu Asp Gln Ser Val Arg Lys Asn Glu Lys Leu Lys Leu
465                 470                 475                 480
Ala Ala Gln Gly Ala Glu Lys Thr Tyr Gly Asn Gly Asp Ser Leu Asn
                485                 490                 495
Thr Gly Lys Leu Lys Asn Asp Lys Val Ser Arg Phe Asp Phe Ile Arg
            500                 505                 510
Gln Ile Glu Val Asp Gly Gln Leu Ile Thr Leu Glu Ser Gly Glu Phe
        515                 520                 525
Gln Val Tyr Lys Gln Ser His Ser Ala Leu Thr Ala Phe Gln Thr Glu
        530                 535                 540
Gln Ile Gln Asp Ser Glu His Ser Gly Lys Met Val Ala Lys Arg Gln
545                 550                 555                 560
Phe Arg Ile Gly Asp Leu Gly Gly Glu His Thr Ala Phe Asn Gln Leu
                565                 570                 575
Pro Asp Gly Lys Ala Glu Tyr Arg Gly Thr Ala Phe Gly Ser Asp Asp
            580                 585                 590
Ala Gly Gly Lys Leu Thr Tyr Thr Ile Asp Phe Thr Lys Lys Gln Gly
        595                 600                 605
```

```
Asn Gly Lys Ile Glu His Leu Lys Ser Pro Glu Leu Asn Val Glu Leu
    610             615                 620
Ala Ser Ala Glu Ile Lys Ala Asp Gly Lys Ser His Ala Val Ile Leu
625             630                 635                 640
Gly Asp Val Arg Tyr Gly Ser Glu Lys Gly Ser Tyr Ser Leu Gly
                645                 650                 655
Ile Phe Gly Gly Arg Ala Gln Glu Val Ala Gly Ser Ala Glu Val Lys
            660                 665                 670
Thr Val Asn Gly Ile Arg His Ile Gly Leu Ala Ala Lys Gln
            675                 680                 685
```

<210> SEQ ID NO 20
<211> LENGTH: 274
<212> TYPE: PRT
<213> ORGANISM: Neisseria meningitidis
<400> SEQUENCE: 20

```
Met Asn Arg Thr Ala Phe Cys Cys Leu Ser Leu Thr Thr Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
            100                 105                 110
Gly Glu Phe Gln Val Tyr Lys Gln Ser His Ser Ala Leu Thr Ala Phe
        115                 120                 125
Gln Thr Glu Gln Ile Gln Asp Ser Glu His Ser Gly Lys Met Val Ala
    130                 135                 140
Lys Arg Gln Phe Arg Ile Gly Asp Ile Ala Gly Glu His Thr Ser Phe
145                 150                 155                 160
Asp Lys Leu Pro Glu Gly Gly Arg Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly Asn Gly Lys Ile Glu His Leu Lys Ser Pro Glu Leu
        195                 200                 205
Asn Val Asp Leu Ala Ala Asp Ile Lys Pro Asp Gly Lys Arg His
    210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                245                 250                 255
Ala Glu Val Lys Thr Val Asn Gly Ile Arg His Ile Gly Leu Ala Ala
            260                 265                 270
Lys Gln
```

<210> SEQ ID NO 21
<211> LENGTH: 273

<212> TYPE: PRT
<213> ORGANISM: Neisseria meningitidis

<400> SEQUENCE: 21

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
                180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
                260                 265                 270

Gln
```

<210> SEQ ID NO 22
<211> LENGTH: 281
<212> TYPE: PRT
<213> ORGANISM: Neisseria meningitidis

<400> SEQUENCE: 22

```
Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Val
            20                  25                  30

Ala Ala Asp Ile Gly Thr Gly Leu Ala Asp Ala Leu Thr Ala Pro Leu
            35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
```

```
                65                  70                  75                  80
        Phe Lys Ala Gly Asp Lys Asp Asn Ser Leu Asn Thr Gly Lys Leu Lys
                        85                  90                  95

Asn Asp Lys Ile Ser Arg Phe Asp Phe Val Gln Lys Ile Glu Val Asp
                        100                 105                 110

Gly Gln Thr Ile Thr Leu Ala Ser Gly Glu Phe Gln Ile Tyr Lys Gln
                        115                 120                 125

Asn His Ser Ala Val Ala Leu Gln Ile Glu Lys Ile Asn Asn Pro
                    130                 135                 140

Asp Lys Thr Asp Ser Leu Ile Asn Gln Arg Ser Phe Leu Val Ser Gly
        145                 150                 155                 160

Leu Gly Gly Glu His Thr Ala Phe Asn Gln Leu Pro Gly Gly Lys Ala
                            165                 170                 175

Glu Tyr His Gly Lys Ala Phe Ser Asp Asp Pro Asn Gly Arg Leu
                    180                 185                 190

His Tyr Ser Ile Asp Phe Thr Lys Lys Gln Gly Tyr Gly Arg Ile Glu
                    195                 200                 205

His Leu Lys Thr Leu Glu Gln Asn Val Glu Leu Ala Ala Ala Glu Leu
                    210                 215                 220

Lys Ala Asp Glu Lys Ser His Ala Val Ile Leu Gly Asp Thr Arg Tyr
        225                 230                 235                 240

Gly Ser Glu Glu Lys Gly Thr Tyr His Leu Ala Leu Phe Gly Asp Arg
                            245                 250                 255

Ala Gln Glu Ile Ala Gly Ser Ala Thr Val Lys Ile Gly Glu Lys Val
                        260                 265                 270

His Glu Ile Gly Ile Ala Gly Lys Gln
                    275                 280

<210> SEQ ID NO 23
<211> LENGTH: 248
<212> TYPE: PRT
<213> ORGANISM: Neisseria meningitidis

<400> SEQUENCE: 23

Val Thr Ala Asp Ile Gly Thr Gly Leu Ala Asp Ala Leu Thr Ala Pro
        1               5                   10                  15

Leu Asp His Lys Asp Lys Gly Leu Lys Ser Leu Thr Leu Glu Asp Ser
                        20                  25                  30

Ile Ser Gln Asn Gly Thr Leu Thr Leu Ser Ala Gln Gly Ala Glu Lys
                    35                  40                  45

Thr Tyr Gly Asn Gly Asp Ser Leu Asn Thr Gly Lys Leu Lys Asn Asp
            50                  55                  60

Lys Val Ser Arg Phe Asp Phe Ile Arg Gln Ile Glu Val Asp Gly Gln
        65                  70                  75                  80

Leu Ile Thr Leu Glu Ser Gly Glu Phe Gln Val Tyr Lys Gln Ser His
                        85                  90                  95

Ser Ala Leu Thr Ala Leu Gln Thr Glu Gln Gln Asp Pro Glu His
                        100                 105                 110

Ser Glu Lys Met Val Ala Lys Arg Arg Phe Arg Ile Gly Asp Ile Ala
                    115                 120                 125

Gly Glu His Thr Ser Phe Asp Lys Leu Pro Lys Asp Val Met Ala Thr
                130                 135                 140

Tyr Arg Gly Thr Ala Phe Gly Ser Asp Asp Ala Gly Gly Lys Leu Thr
        145                 150                 155                 160
```

```
Tyr Thr Ile Asp Phe Ala Ala Lys Gln Gly His Gly Lys Ile Glu His
                165                 170                 175

Leu Lys Ser Pro Glu Leu Asn Val Asp Leu Ala Val Ala Tyr Ile Lys
            180                 185                 190

Pro Asp Glu Lys His His Ala Val Ile Ser Gly Ser Val Leu Tyr Asn
        195                 200                 205

Gln Asp Glu Lys Gly Ser Tyr Ser Leu Gly Ile Phe Gly Glu Lys Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln
                245

<210> SEQ ID NO 24
<211> LENGTH: 260
<212> TYPE: PRT
<213> ORGANISM: Neisseria meningitidis

<400> SEQUENCE: 24

Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
    115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
    195                 200                 205

His His Ala Val Ile Ser Gly Ser Val Leu Tyr Asn Gln Asp Glu Lys
210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260

<210> SEQ ID NO 25
```

```
<211> LENGTH: 250
<212> TYPE: PRT
<213> ORGANISM: Neisseria meningitidis

<400> SEQUENCE: 25
```

| | | | | | | | | | | | | | | |
|---|---|---|---|---|---|---|---|---|---|---|---|---|---|---|
| Val | Ala | Ala | Asp | Ile | Gly | Thr | Gly | Leu | Ala | Asp | Ala | Leu | Thr | Ala | Pro |
| 1 | | | | 5 | | | | | 10 | | | | | 15 | |
| Leu | Asp | His | Lys | Asp | Lys | Gly | Leu | Lys | Ser | Leu | Thr | Leu | Glu | Asp | Ser |
| | | | 20 | | | | | 25 | | | | | 30 | | |
| Ile | Ser | Gln | Asn | Gly | Thr | Leu | Thr | Leu | Ser | Ala | Gln | Gly | Ala | Glu | Lys |
| | | | 35 | | | | | 40 | | | | | 45 | | |
| Thr | Phe | Lys | Val | Gly | Asp | Lys | Asp | Asn | Ser | Leu | Asn | Thr | Gly | Lys | Leu |
| | 50 | | | | | 55 | | | | | 60 | | | | |
| Lys | Asn | Asp | Lys | Ile | Ser | Arg | Phe | Asp | Phe | Val | Gln | Lys | Ile | Glu | Val |
| 65 | | | | | 70 | | | | | 75 | | | | | 80 |
| Asp | Gly | Gln | Thr | Ile | Thr | Leu | Ala | Ser | Gly | Glu | Phe | Gln | Ile | Tyr | Lys |
| | | | | 85 | | | | | 90 | | | | | 95 | |
| Gln | Asp | His | Ser | Ala | Val | Val | Ala | Leu | Gln | Ile | Glu | Lys | Ile | Asn | Asn |
| | | | 100 | | | | | 105 | | | | | 110 | | |
| Pro | Asp | Lys | Ile | Asp | Ser | Leu | Ile | Asn | Gln | Arg | Ser | Phe | Leu | Val | Ser |
| | | | 115 | | | | | 120 | | | | | 125 | | |
| Gly | Leu | Gly | Gly | Glu | His | Thr | Ala | Phe | Asn | Gln | Leu | Pro | Ser | Gly | Lys |
| | 130 | | | | | 135 | | | | | 140 | | | | |
| Ala | Glu | Tyr | His | Gly | Lys | Ala | Phe | Ser | Ser | Asp | Asp | Ala | Gly | Gly | Lys |
| 145 | | | | | 150 | | | | | 155 | | | | | 160 |
| Leu | Thr | Tyr | Thr | Ile | Asp | Phe | Ala | Ala | Lys | Gln | Gly | His | Gly | Lys | Ile |
| | | | | 165 | | | | | 170 | | | | | 175 | |
| Glu | His | Leu | Lys | Thr | Pro | Glu | Gln | Asn | Val | Glu | Leu | Ala | Ser | Ala | Glu |
| | | | 180 | | | | | 185 | | | | | 190 | | |
| Leu | Lys | Ala | Asp | Glu | Lys | Ser | His | Ala | Val | Ile | Leu | Gly | Asp | Thr | Arg |
| | | | 195 | | | | | 200 | | | | | 205 | | |
| Tyr | Gly | Ser | Glu | Glu | Lys | Gly | Thr | Tyr | His | Leu | Ala | Leu | Phe | Gly | Asp |
| | 210 | | | | | 215 | | | | | 220 | | | | |
| Arg | Ala | Gln | Glu | Ile | Ala | Gly | Ser | Ala | Thr | Val | Lys | Ile | Arg | Glu | Lys |
| 225 | | | | | 230 | | | | | 235 | | | | | 240 |
| Val | His | Glu | Ile | Gly | Ile | Ala | Gly | Lys | Gln | | | | | | |
| | | | | 245 | | | | | 250 | | | | | | |

```
<210> SEQ ID NO 26
<211> LENGTH: 261
<212> TYPE: PRT
<213> ORGANISM: Neisseria meningitidis

<400> SEQUENCE: 26
```

| | | | | | | | | | | | | | | |
|---|---|---|---|---|---|---|---|---|---|---|---|---|---|---|
| Cys | Ser | Ser | Gly | Ser | Gly | Ser | Gly | Gly | Gly | Val | Ala | Ala | Asp | Ile |
| 1 | | | | 5 | | | | | 10 | | | | | 15 |
| Gly | Thr | Gly | Leu | Ala | Asp | Ala | Leu | Thr | Ala | Pro | Leu | Asp | His | Lys | Asp |
| | | | 20 | | | | | 25 | | | | | 30 | | |
| Lys | Gly | Leu | Lys | Ser | Leu | Thr | Leu | Glu | Asp | Ser | Ile | Ser | Gln | Asn | Gly |
| | | | 35 | | | | | 40 | | | | | 45 | | |
| Thr | Leu | Thr | Leu | Ser | Ala | Gln | Gly | Ala | Glu | Lys | Thr | Phe | Lys | Val | Gly |
| | 50 | | | | | 55 | | | | | 60 | | | | |
| Asp | Lys | Asp | Asn | Ser | Leu | Asn | Thr | Gly | Lys | Leu | Lys | Asn | Asp | Lys | Ile |
| 65 | | | | | 70 | | | | | 75 | | | | | 80 |
| Ser | Arg | Phe | Asp | Phe | Val | Gln | Lys | Ile | Glu | Val | Asp | Gly | Gln | Thr | Ile |
| | | | | 85 | | | | | 90 | | | | | 95 | |

```
Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
            115                 120                 125

Ser Leu Ile Asn Gln Arg Ser Phe Leu Val Ser Gly Leu Gly Gly Glu
            130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
                180                 185                 190

Pro Glu Gln Asn Val Glu Leu Ala Ser Ala Glu Leu Lys Ala Asp Glu
                195                 200                 205

Lys Ser His Ala Val Ile Leu Gly Asp Thr Arg Tyr Gly Ser Glu Glu
            210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 27
<211> LENGTH: 776
<212> TYPE: PRT
<213> ORGANISM: Artificial Sequence
<220> FEATURE:
<223> OTHER INFORMATION: Hybrid protein

<400> SEQUENCE: 27

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
            115                 120                 125

Ile Asn Gln Arg Ser Phe Leu Val Ser Gly Leu Gly Gly Glu His Thr
        130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190
```

```
Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Pro Asp Ser Asp Arg Leu Gln Gln Arg Arg
            260                 265                 270

Val Ala Ala Asp Ile Gly Thr Gly Leu Ala Asp Ala Leu Thr Ala Pro
        275                 280                 285

Leu Asp His Lys Asp Lys Gly Leu Lys Ser Leu Thr Leu Glu Asp Ser
    290                 295                 300

Ile Pro Gln Asn Gly Thr Leu Thr Leu Ser Ala Gln Gly Ala Glu Lys
305                 310                 315                 320

Thr Phe Lys Ala Gly Asp Lys Asp Asn Ser Leu Asn Thr Gly Lys Leu
                325                 330                 335

Lys Asn Asp Lys Ile Ser Arg Phe Asp Phe Val Gln Lys Ile Glu Val
            340                 345                 350

Asp Gly Gln Thr Ile Thr Leu Ala Ser Gly Glu Phe Gln Ile Tyr Lys
        355                 360                 365

Gln Asn His Ser Ala Val Val Ala Leu Gln Ile Glu Lys Ile Asn Asn
    370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                405                 410                 415

Ala Glu Tyr His Gly Lys Ala Phe Ser Ser Asp Asp Pro Asn Gly Arg
            420                 425                 430

Leu His Tyr Ser Ile Asp Phe Thr Lys Lys Gln Gly Tyr Gly Arg Ile
        435                 440                 445

Glu His Leu Lys Thr Leu Glu Gln Asn Val Glu Leu Ala Ala Ala Glu
    450                 455                 460

Leu Lys Ala Asp Glu Lys Ser His Ala Val Ile Leu Gly Asp Thr Arg
465                 470                 475                 480

Tyr Gly Ser Glu Glu Lys Gly Thr Tyr His Leu Ala Leu Phe Gly Asp
                485                 490                 495

Arg Ala Gln Glu Ile Ala Gly Ser Ala Thr Val Lys Ile Gly Glu Lys
            500                 505                 510

Val His Glu Ile Gly Ile Ala Gly Lys Gln Gly Ser Gly Gly Gly Gly
        515                 520                 525

Val Ala Ala Asp Ile Gly Ala Gly Leu Ala Asp Ala Leu Thr Ala Pro
530                 535                 540

Leu Asp His Lys Asp Lys Gly Leu Gln Ser Leu Thr Leu Asp Gln Ser
545                 550                 555                 560

Val Arg Lys Asn Glu Lys Leu Lys Leu Ala Ala Gln Gly Ala Glu Lys
                565                 570                 575

Thr Tyr Gly Asn Gly Asp Ser Leu Asn Thr Gly Lys Leu Lys Asn Asp
            580                 585                 590

Lys Val Ser Arg Phe Asp Phe Ile Arg Gln Ile Glu Val Asp Gly Gln
        595                 600                 605
```

```
Leu Ile Thr Leu Glu Ser Gly Glu Phe Gln Val Tyr Lys Gln Ser His
            610                 615                 620

Ser Ala Leu Thr Ala Phe Gln Thr Glu Gln Ile Gln Asp Ser Glu His
625                 630                 635                 640

Ser Gly Lys Met Val Ala Lys Arg Gln Phe Arg Ile Gly Asp Ile Ala
                645                 650                 655

Gly Glu His Thr Ser Phe Asp Lys Leu Pro Glu Gly Gly Arg Ala Thr
            660                 665                 670

Tyr Arg Gly Thr Ala Phe Gly Ser Asp Asp Ala Gly Gly Lys Leu Thr
                675                 680                 685

Tyr Thr Ile Asp Phe Ala Ala Lys Gln Gly Asn Gly Lys Ile Glu His
            690                 695                 700

Leu Lys Ser Pro Glu Leu Asn Val Asp Leu Ala Ala Ala Asp Ile Lys
705                 710                 715                 720

Pro Asp Gly Lys Arg His Ala Val Ile Ser Gly Ser Val Leu Tyr Asn
                725                 730                 735

Gln Ala Glu Lys Gly Ser Tyr Ser Leu Gly Ile Phe Gly Gly Lys Ala
            740                 745                 750

Gln Glu Val Ala Gly Ser Ala Glu Val Lys Thr Val Asn Gly Ile Arg
                755                 760                 765

His Ile Gly Leu Ala Ala Lys Gln
            770                 775

<210> SEQ ID NO 28
<211> LENGTH: 247
<212> TYPE: PRT
<213> ORGANISM: Artificial Sequence
<220> FEATURE:
<223> OTHER INFORMATION: Modified fHbp sequence

<400> SEQUENCE: 28

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Leu Gly
            115                 120                 125

Gly Glu His Thr Ala Phe Asn Gln Leu Pro Asp Gly Lys Ala Glu Tyr
        130                 135                 140

Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
                165                 170                 175

Lys Ser Pro Glu Leu Asn Val Glu Leu Ala Ser Ala Glu Ile Lys Ala
                180                 185                 190
```

```
Asp Gly Lys Ser His Ala Val Ile Leu Gly Asp Val Arg Tyr Gly Ser
            195                 200                 205

Glu Glu Lys Gly Ser Tyr Ser Leu Gly Ile Phe Gly Gly Arg Ala Gln
        210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 29
<211> LENGTH: 758
<212> TYPE: PRT
<213> ORGANISM: Neisseria meningitidis

<400> SEQUENCE: 29

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285

Gln Leu Tyr Pro His Leu Leu Thr Glu Glu Asp Ile Asp Tyr Asp Asn
    290                 295                 300

Pro Gly Leu Ser Cys Gly Phe His Asp Asp Asn Ala His Ala His
305                 310                 315                 320
```

```
Thr His Ser Gly Arg Pro Trp Ile Asp Leu Arg Asn Lys Arg Tyr Glu
            325                 330                 335

Leu Arg Ala Glu Trp Lys Gln Pro Phe Pro Gly Phe Glu Ala Leu Arg
            340                 345                 350

Val His Leu Asn Arg Asn Asp Tyr Arg His Asp Glu Lys Ala Gly Asp
            355                 360                 365

Ala Val Glu Asn Phe Phe Asn Asn Gln Thr Gln Asn Ala Arg Ile Glu
    370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
            435                 440                 445

Arg Val Glu Lys Gln Lys Ala Ser Ile Gln Tyr Asp Lys Ala Leu Ile
    450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
            515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Asp Ser Glu Met Lys Leu
            580                 585                 590

Val Arg Tyr Asn Gln Ser Gly Ala Asp Phe Tyr Gly Ala Glu Gly Glu
            595                 600                 605

Ile Tyr Phe Lys Pro Thr Pro Arg Tyr Arg Ile Gly Val Ser Gly Asp
    610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Phe His Leu Lys Ala Ser Leu
            660                 665                 670

Thr Asp Arg Ile Asp Ala Asn Leu Asp Tyr Tyr Arg Val Phe Ala Gln
            675                 680                 685

Asn Lys Leu Ala Arg Tyr Glu Thr Arg Thr Pro Gly His His Met Leu
    690                 695                 700
```

```
Asn Leu Gly Ala Asn Tyr Arg Arg Asn Thr Arg Tyr Gly Glu Trp Asn
705             710                 715                 720

Trp Tyr Val Lys Ala Asp Asn Leu Leu Asn Gln Ser Val Tyr Ala His
            725                 730                 735

Ser Ser Phe Leu Ser Asp Thr Pro Gln Met Gly Arg Ser Phe Thr Gly
            740                 745                 750

Gly Val Asn Val Lys Phe
            755
```